US008815255B2

(12) United States Patent
Beck et al.

(10) Patent No.: US 8,815,255 B2
(45) Date of Patent: *Aug. 26, 2014

(54) USE OF *MYCOPLASMA BOVIS* ANTIGEN

(75) Inventors: Michael Beck, St. Joseph, MO (US); Phillip Wayne Hayes, Maurice, IA (US); Jeffrey P. Knittel, Parkville, MO (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 84 days.

This patent is subject to a terminal disclaimer.

(21) Appl. No.: 13/056,501

(22) PCT Filed: Oct. 22, 2009

(86) PCT No.: PCT/US2009/061610
§ 371 (c)(1),
(2), (4) Date: Jun. 6, 2011

(87) PCT Pub. No.: WO2010/051210
PCT Pub. Date: May 6, 2010

(65) Prior Publication Data
US 2012/0093854 A1    Apr. 19, 2012

Related U.S. Application Data

(60) Provisional application No. 61/110,286, filed on Oct. 31, 2008.

(51) Int. Cl.
| *A61K 39/00* | (2006.01) |
| *A61K 39/02* | (2006.01) |
| *A61K 39/04* | (2006.01) |
| *A61K 45/00* | (2006.01) |
| *A61K 47/00* | (2006.01) |

(52) U.S. Cl.
USPC ..... 424/264.1; 424/1.57; 424/93.1; 424/93.2; 424/93.4; 424/150.1; 424/168.1; 424/184.1; 424/200.1; 424/203.1; 424/234.1; 424/248.1; 424/278.1

(58) Field of Classification Search
None
See application file for complete search history.

(56) References Cited

U.S. PATENT DOCUMENTS

| 6,548,069 B2 | 4/2003 | Hymas et al. |
| 7,429,389 B2 | 9/2008 | Leonard et al. |

(Continued)

FOREIGN PATENT DOCUMENTS

| WO | 9902670 A1 | 1/1999 |
| WO | 9964604 A2 | 12/1999 |

(Continued)

OTHER PUBLICATIONS

Thorns et al., (Research in Vet. Science, 1980. vol. 29:328-332).*

(Continued)

*Primary Examiner* — Ja'na Hines
(74) *Attorney, Agent, or Firm* — Michael P. Morris; Joyce L. Morrison

(57) ABSTRACT

The present invention relates to combination vaccines and/or the combined use of immunogenic compositions for the treatment and/or prophylaxis of cattle against microbiological infections, wherein the infections are caused by *M. bovis* and at least one further cattle relevant pathogen. The combination vaccine as described herein comprises at least one *M. bovis* antigen, preferably the attenuated, avirulent *M. bovis* as provided herewith and one or more further immunologically active components effective for the treatment and/or prophylaxis of infections caused by a further pathogen of cattle.

15 Claims, 3 Drawing Sheets

Frequency of Culture Recovery from Nasal, Tonsil and Lung Samples (Days 0, 14, 28, 35 and Post)

(56) References Cited

U.S. PATENT DOCUMENTS

| | | | |
|---|---|---|---|
| 2002/0150593 A1* | 10/2002 | Hymas et al. | 424/201.1 |
| 2003/0064079 A1 | 4/2003 | Goudie et al. | |
| 2003/0147914 A1* | 8/2003 | Keich et al. | 424/201.1 |
| 2003/0180219 A1 | 9/2003 | Keich et al. | |
| 2005/0053627 A1 | 3/2005 | Leonard et al. | |
| 2007/0077260 A1* | 4/2007 | Leonard et al. | 424/264.1 |
| 2008/0069842 A9 | 3/2008 | Leonard et al. | |
| 2008/0193463 A1 | 8/2008 | Frey et al. | |
| 2008/0226671 A1 | 9/2008 | Leonard et al. | |
| 2009/0068231 A1 | 3/2009 | Kumar et al. | |
| 2009/0130148 A1 | 5/2009 | Beck et al. | |
| 2010/0272759 A1 | 10/2010 | Beck et al. | |
| 2011/0059437 A1 | 3/2011 | Beck | |
| 2012/0093854 A1 | 4/2012 | Beck et al. | |

FOREIGN PATENT DOCUMENTS

| | | | |
|---|---|---|---|
| WO | 0134189 A2 | 5/2001 | |
| WO | 03004051 A2 | 1/2003 | |
| WO | 03004052 A1 | 1/2003 | |
| WO | 03017755 A2 | 3/2003 | |
| WO | 2005111201 A1 | 11/2005 | |
| WO | 2008030619 A2 | 3/2008 | |
| WO | 2009036241 A1 | 3/2009 | |
| WO | 2009058833 A2 | 5/2009 | |
| WO | 2010002537 A1 | 1/2010 | |
| WO | 2010051210 A1 | 5/2010 | |
| WO | 2010124154 A1 | 10/2010 | |

OTHER PUBLICATIONS

Mostowy et al., (Vaccine 2003. vol. 21. Issue 27-30: 4270-4274).*
Alberti et al., "Molecular and antigenic characterization of a *Mycoplasma bovis* strain causing an outbreak of infectious keratoconjunctivitis". 2006, Journal of Veterinary Diagnostic Investigation, vol. 18, pp. 41-51.
Angen et al., "Respiratory disease in calves: Microbiological investigations on trans-tracheally aspirated bronchoalveolar fluid and acute phase protein response". 2009, Veterinary Microbiology, vol. 137, pp. 165-171.
Boddie et al., "Germicidal Activities of Representatives of Five Different Teat Dip Classes Against Three Bovine *Mycoplasma* Species Using a Modified Excised Teat Model". 2002, Journal of Dairy Science, vol. 85, pp. 1909-1912.
Boothby et al., "Immune Responses to *Mycoplasma bovis* Vaccination and Experimental Infection in the Bovine Mammary Gland". 1988, Canadian Journal of Veterinary Research, vol. 52, pp. 355-359.
Brank et al., "Development of a Recombinant Antigen for Antibody-Based Diagnosis of *Mycoplasma bovis* Infection in Cattle". Nov. 1999, Clinical and Diagnostic Laboratory Immunology, vol. 6, No. 6, pp. 861-867.
Bush et al., "Characterization of a lympho-inhibitory peptide produced by *Mycoplasma bovis*". 2004, Biochemical and Biophysical Research Communications, vol. 315, pp. 336-341.
Butler et al., "Pasteurization of Discard *Mycoplasma* Mastitic Milk Used to Feed Calves: Thermal Effects on Various *Mycoplasma*". 2000, Journal of Dairy Science, vol. 83, pp. 2285-2288.
Byrne et al., "*Mycoplasma bovis* arthritis as a sequel to respiratory disease in bought-in weanling cattle in the Republic of Ireland". Oct. 2001, Irish Veterinary Journal, vol. 54(10), pp. 516-519.
Cai et al., "Development of a real-time PCR for detection of *Mycoplasma bovis* in bovine milk and lung samples". 2005, Journal of Veterinary Diagnostic Investigation, vol. 17, pp. 537-545.
Caswell et al., "*Mycoplasma bovis* pneumonia in cattle". 2008, Animal Health Research Reviews, vol. 8(2), pp. 161-186.
Chima et al., "Immunoprophylaxis of Experimental *Mycoplasma bovis* Arthritis in Calves. Protective Efficacy of Live Organisms and Formalinized Vaccines". 1980, Veterinary Microbiology, vol. 5, pp. 113-122.
Devriese et al., "Antibiotic Susceptibility Testing of *Mycoplasma bovis* using Tween 80 Hydrolysis as an Indicator of Growth". 1991, Journal of Veterinary Medicine B, vol. 38, pp. 781-783.

Duarte et al., "Otitis in Cattle, an Aetiological Review". 2004, Journal of Veterinary Medicine B, vol. 51, pp. 1-7.
Gagea et al., "Diseases and pathogens associated with mortality in Ontario beef feedlots". 2006, Journal of Veterinary Diagnostic Investigation, vol. 18, pp. 18-28.
Gagea et al., "Naturally occurring *Mycoplasma bovis*-associated pneumonia and polyarthritis in feedlot beef calves". 2006, Journal of Veterinary Diagnostic Investigation, vol. 18, pp. 29-40.
Geary et al., "Inflammatory Toxin from *Mycoplasma bovis*: Isolation and Characterization". May 1981, Science, vol. 212, pp. 1032-1033.
Ghadersohi et al., "Development of a monoclonal blocking ELISA for the detection of antibody to *Mycoplasma bovis* in dairy cattle and comparison to detection by PCR". 2005, Veterinary Immunology and immunopathology, vol. 104, pp. 183-193.
Gourlay et al., "Experimental pneumonia in conventionally reared and gnotobiotic calves by dual infection with *Mycoplasma bovis* and *Pasteurella haemolytica*". 1985, Research in Veterinary Science, vol. 28, pp. 377-382.
Hannan et al., "Comparative Susceptibilities of Various Animal-Pathogenic Mycoplasmas to Fluoroquinolones". 1997, Antimicrobial Agents and Chemotherapy, vol. 41, No. 9, pp. 2037-2040.
Hannan, P., "Guidelines and recommendations for antimicrobial minimum inhibitory concentration (MIC) testing against veterinary *Mycoplasma* species". 2000, Veterinary Research, vol. 31, pp. 373-395.
Howard et al., Comparative Pathogenicity of *Mycoplasma bovis* and *Mycoplasma dispar* for the Respiratory Tract of Calves. 1987, Israel Journal of Medical Sciences, vol. 23, pp. 621-624.
International Search Report for PCT/US2009/061610 mailed Jan. 15, 2010. (10-0116-PCT).
Khan et al., "Biochemical characterisation of some non fermenting, non arginine hydrolysing mycoplasmas of ruminants". 2005, Veterinary Microbiology, vol. 109, pp. 129-134.
Khodakaram-Tafti et al., "Immunohistopathological Findings in the Lungs of Calves Naturally Infected with *Mycoplasma bovis*". 2004, Journal of Veterinary Medicine A, vol. 51, pp. 10-14.
Krysak, D., "Chronic pneumonia and polyarthritis syndrome in a feedlot calf". Oct. 2006, Canadian Veterinary Journal, vol. 47, pp. 1019-1022.
Lin et al., "A rapid chromogenic microtitre assay of arginine aminopeptidase activity in *Mycoplasma* strains". 2006, Systematic and Applied Microbiology, vol. 29, pp. 589-592.
Lysnyansky et al., "Juxtaposition of an Active Promoter to vsp Genes via Site-Specific DNA Inversions Generates Antigenic Variation in *Mycoplasma bovis*". Oct. 2001, Journal of Bacteriology, vol. 183, No. 19, pp. 5698-5708.
Lysnyansky et al., "Molecular characterization of the *Mycoplasma bovis* p68 gene, encoding a basic membrane protein with homology to P48 of *Mycoplasma agalactiae*". 2008, FEMS Microbiology Letters, vol. 279, pp. 234-242.
Madoff et al., "Isolation of *Mycoplasma bovis* from a Patient with Systemic Illness". Jun. 1979, Journal of Clinical Microbiology, vol. 9, No. 6, pp. 709-711.
Maunsell et al., "*Mycoplasa bovis* Infections in Young Calves". 2009, Vet Clin Food Anim, vol. 25, pp. 139-177.
Miles et al., "Insertion sequence profiling of UK *Mycoplasma bovis* field isolates". 2005, Veterinary Microbiology, vol. 107, pp. 301-306.
Mostowy et al., "The in vitro evolution of BCG vaccines". 2003, Vaccine, vol. 21, pp. 4270-4274.
Nicholas et al., "An experimental vaccine for calf pneumonia caused by *Mycoplasma bovis*: clinical, cultural, serological and pathological findings". 2002, Vaccine, vol. 20, pp. 3569-3575.
Nicholas et al., "Mycoplasmas in Adult Cattle: Bugs Worth Bothering with?". 2005, British Cattle Veterinary Association, vol. 13, Part 2, pp. 167-170.
Nicholas et al., "Vaccines for *Mycoplasma* Diseases in Animals and Man". 2009, Journal of Comparative Pathology, vol. 140, pp. 85-96.
Pfuetzner et al., "*Mycoplasma bovis* as an agent of mastitis, pneumonia, arthritis and genital disorders in cattle". 1996, Rev. sci. tech. Off. int. Epiz., vol. 15(4), pp. 1477-1494.
Razin et al., "Molecular Biology and Pathogenicity of Mycoplasmas". Dec. 1998, Microbiology and Molecular Biology Reviews, vol. 62, No. 4, pp. 1094-1156.

(56) References Cited

OTHER PUBLICATIONS

Rodriguez et al., "Immunohistochemical Characterization of Lung Lesions Induced Experimentally by *Mycoplasma agalactiae* and *Mycoplasma bovis* in Goats". 2000, Journal of Comparative Pathology, vol. 123, pp. 285-293.

Rosenbusch et al., "In vitro antimicrobial inhibition profiles of *Mycoplasma bovis* isolates recovered from various regions of the United States from 2002 to 2003". 2005, Journal of Veterinary Diagnostic Investigation, vol. 17, pp. 436-441.

Rosengarten et al. "Antigen Heterogeneity among Isolates of *Mycoplasma bovis* is Generated by High-Frequency Variation of Diverse Membrane Surface Proteins". Nov. 1994, Infection and Immunity, vol. 62, No. 11, pp. 5066-5074.

Sachse et al., "Comparison of *Mycoplasma bovis* Strains Based on SDS-PAGE and Immunoblot Protein Patterns". 1992, Journal of Veterinary Medicine B, vol. 39, pp. 246-252.

Stalheim et al., "Naturally Occurring and Experimentally Induced Mycoplasmal Arthritis of Cattle". Sep. 1975, Journal of Clinical Microbiology, vol. 2, No. 3, pp. 165-168.

Tenk et al., "Detection of *Mycoplasma bovis* with an Improved PCR Assay". 2006, Acta Veterinaria Hungarica, vol. 54(4), pp. 427-435.

Thomas et al., "Adherence of *Mycoplasma bovis* to bovine bronchial epithelial cells". 2003, Microbial Pathogenesis, vol. 34, pp. 141-148.

Thomas et al., "Adherence to various host cell lines of *Mycoplasma bovis* strains differing in pathogenic and cultural features". 2003, Veterinary Microbiology, vol. 91, pp. 101-113.

Thomas et al., "The p40 adhesin pseudogene of *Mycoplasma bovis*". 2004, Veterinary Microbiology, vol. 104, pp. 213-217.

Thorns, et al., "Effect of Serial Passages Through Liquid Medium on the Virulence of *Mycoplasma-bovis* for the Mouse Mammary Gland", Research in Veterinary Science, vol. 29, No. 3, 1980 pp. 328-332.

Vicca et al., "In Vitro Susceptibilities of *Mycoplasma hyopneumoniae* Field Isolates". Nov. 2004, Antimicrobial Agents and Chemotherapy, vol. 48, No. 11, pp. 4470-4472.

Written Opinion of the International Searching Authority for PCT/US2009/061610 mailed Jan. 15, 2010. (10-0116-PCT).

Zhang et al., "Attenuated *Mycoplasma bovis* strains provide protection against avirulent infection in calves". Vaccine, 2014, 8 pages. [Accessed at: http://dx.doi.org/10.1016/j.vaccine.2013.12.004].

\* cited by examiner

Frequency of Culture Recovery from Nasal, Tonsil and Lung Samples

(Days 0, 14, 28, 35 and Post)

Frequency of PCR Detection from Nasal, Tonsil and Lung Samples

(Days 0, 14, 28, 35 and Post)

Group 1=Vaccine / High Respiratory Challenge; 2=Vaccine / Low Respiratory Challenge; 3=No Vaccine / High Respiratory Challenge; 4=No Vaccine / Low Respiratory Challenge

Figure 3:

**Average Group Score for *M. bovis* specific Antibodies from Serum Samples**

(Days 0, 14, 28, 35 and 42)

Group 1=Vaccine / High Volume Respiratory Challenge; 2=Vaccine /Low Respiratory Challenge; 3=No Vaccine / High Volume Respiratory Challenge; 4=No Vaccine / Low Respiratory Challenge

Figure 4:

Comparison of Serology for Live Vac I, II, III and No Vaccine Group (SQ+IN only)

Comparison of Serology for Live Vac I using Various Routes of Administration

SEQUENCE LISTING

<160> NUMBER OF SEQ ID NOS: 8

<210> SEQ ID NO 1
<211> LENGTH: 21
<212> TYPE: DNA
<213> ORGANISM: Mycoplasma bovis

<400> SEQUENCE: 1
ccgcaagtta acttgtggtg c                                          21

<210> SEQ ID NO 2
<211> LENGTH: 24
<212> TYPE: DNA
<213> ORGANISM: Mycoplasma bovis

<400> SEQUENCE: 2
ggccattttc ttgtcagaac cacc                                       24

<210> SEQ ID NO 3
<211> LENGTH: 29
<212> TYPE: DNA
<213> ORGANISM: Mycoplasma bovis

```
<400> SEQUENCE: 3
gcttttactc tggtactaga tggtcttgg                                    29

<210> SEQ ID NO 4
<211> LENGTH: 30
<212> TYPE: DNA
<213> ORGANISM: Mycoplasma bovis

<400> SEQUENCE: 4
gtggcgttct tgacaataga acaattagtg                                   30

<210> SEQ ID NO 5
<211> LENGTH: 26
<212> TYPE: DNA
<213> ORGANISM: Mycoplasma bovis

<400> SEQUENCE: 5
gatgttcttc attgtctttt gcatcg                                       26

<210> SEQ ID NO 6
<211> LENGTH: 23
<212> TYPE: DNA
<213> ORGANISM: Mycoplasma bovis

<400> SEQUENCE: 6
cgacgagtta caagaaagtt ggc                                          23

<210> SEQ ID NO 7
<211> LENGTH: 29
<212> TYPE: DNA
<213> ORGANISM: Mycoplasma bovis

<400> SEQUENCE: 7
gaaacaccta tcccagtagg tacaagatc                                    29

<210> SEQ ID NO 8
<211> LENGTH: 33
<212> TYPE: DNA
<213> ORGANISM: Mycoplasma bovis

<400> SEQUENCE: 8
gtctacattg ttcaaaatgc gacattttgt ata                               33
```

USE OF *MYCOPLASMA BOVIS* ANTIGEN

SEQUENCE LISTING

This application contains a sequence listing in paper format and in computer readable format, the teachings and content of which are hereby incorporated by reference. The sequence listing is identical to that incorporated in WO2008/030619.

BACKGROUND

*Mycoplasma bovis* (*M. bovis*) is considered to be one of the more pathogenic species of *Mycoplasma* and causes significant economic losses worldwide. *Mycoplasmas* cause severe clinical signs in cattle of all ages. *M. bovis* is the most frequent *Mycoplasma* pathogen found to cause pneumonia, mastitis, and arthritis in cattle and its etiological role has also been associated with otitis, keratoconjunctivitis, synovitis, and reproductive disorders in cows and bulls. In general, *Mycoplasmas* are difficult to treat since they lack a cell wall or membrane, which tends to make them resistant to several classes of commonly used broad-spectrum antibiotic treatments. *Mycoplasmas* differ from viruses in that *Mycoplasmas* are larger than most viruses and damage tissue cells by attaching to the surface of cells and destroying them, rather than by entering the cells. Animals infected with *M. bovis* have depressed immune responses and can exhibit signs of *M. bovis* infection such as fever, depression, anorexia, labored breathing, nasal and ocular discharge, coughing, sneezing, gasping, grunting, lameness and swollen joints, mastitis, middle ear infections, abortions, recumbence and death. The organism persists in unsanitary, warm, moist environments. *Mycoplasmas* can survive in milk, and even seem to thrive in the presence of large numbers of leukocytes, which are produced in response to the infection.

There are several references available in the art disclosing *M. bovis* vaccines. U.S. Pat. No. 6,548,069 discloses a vaccine composition that incorporates a whole cell inactivated bacterin containing at least two killed *M. bovis* strains. Other references available disclose passaging an *M. bovis* strain less than 10 times to prepare an inactivated vaccine, but do not describe attenuation of an infectious or pathogenic *M. bovis* strain through serial passaging or any such attenuated live *M. bovis* strain as the essence of an avirulent live culture vaccine.

The prior art is deficient in that killed *M. bovis* is not as effective or efficient in lessening the severity of clinical symptoms associated with a *Mycoplasma bovis* infection. Even passage at a low level does not produce a *Mycoplasma* vaccine with high efficacy such that clinical symptoms are greatly reduced. The few low passage, inactivated, *M. bovis* vaccines that are available do not show a large reduction in the severity of clinical symptoms. Additionally, the U.S. Pat. No. 6,548,069 strongly teaches away from the idea of a high passage, attenuated strain of *M. bovis* being used in an immunogenic or vaccine composition by teaching:

"Because a *Mycoplasma* isolate may rapidly alter its antigens in culture, high passage strains of greater than about 50 passages may lose infectivity and elicit a poorer immune response when used in a bacterin of the present invention. Therefore, it is preferable to employ freshly isolated strains or cultured strains that are still virulent; that is, strains that have retained the ability to be infectious in the host animal. While no critical number of generations is known to exist, the present invention preferably starts with a *Mycoplasma* strain which has been passed no more than about ten, and preferably only about five or less times before mass scale production. By using strains with fewer generations in culture, it is believed that the antigens retain their natural state and thus will elicit a protective immune response against the infectious microorganism."

Bovine viral diarrhea virus (BVDV) type 1 (BVDV-1) and type 2 (BVDV-2) cause bovine viral diarrhea (BVD) and mucosal disease (MD) in cattle (Baker, 1987; Moennig and Plagemann, 1992; Thiel et al., 1996). The division of BVDV into 2 serotypes is based on significant differences at the level of genomic sequences (summarized in Heinz et al., 2000) which are also obvious from limited cross neutralizing antibody reactions (Ridpath et al. 1994). Inactivation of the RNase activity residing within the $E^{rns}$ results in an attenuated apathogenic BVDV which can be used as a modified live vaccine (WO 99/64604, the content of which is entirely incorporated by reference). The international patent application WO2005/111201 (the content of which is entirely incorporated by reference) provides a further generation of an attenuated BVDV suitable for MLV vaccines, which comprises a multiple modified BVDV having at least one mutation in the coding sequence for glycoprotein $E^{rns}$ and at least another mutation in the coding sequence for $N^{pro}$, wherein said mutation in the coding sequence for glycoprotein $E^{rns}$ leads to inactivation of RNase activity residing in $E^{rns}$ and/or said mutation in the coding sequence for $N^{pro}$ leads to inactivation of said $N^{pro}$. Furthermore, various conventional attenuated BVDV viruses are known in the art, which are also suitable candidates for vaccine development.

Parainfluenza-3 virus (PI-3) is an RNA virus classified in the paramyxovirus family. Infections caused by PI-3 are common in cattle. Although PI-3 is capable of causing disease, it is usually associated with mild to subclinical infections. The most important role of PI-3 is to serve as an initiator that can lead to the development of secondary bacterial pneumonia. Clinical signs include pyrexia, cough, serous nasal and lacrimal discharge, increased respiratory rate, and increased breath sounds. The severity of clinical signs worsen with the onset of bacterial pneumonia. Fatalities from uncomplicated PI-3 pneumonia are rare. Lesions include cranioventral lung consolidation, bronchiolitis, and alveolitis with marked congestion and haemorrhage. Inclusion bodies may be identified. Most fatal cases will also have a concurrent bacterial bronchopneumonia.

Bovine Respiratory Syncytial Virus (BRSV) is an RNA virus classified as a pneumovirus in the paramyxovirus family. In addition to cattle, sheep and goats can also be infected by respiratory syncytial viruses. This virus was named for its characteristic cytopathic effect—the formation of syncytial cells. BRSV is distributed worldwide, and the virus is indigenous in the cattle population. BRSV infections associated with respiratory disease occur predominantly in young beef and dairy cattle. Passively derived immunity does not appear to prevent BRSV infections but will reduce the severity of disease. Initial exposures to the virus are associated with severe respiratory disease; subsequent exposures result in mild to subclinical disease. BRSV appears to be an important virus in the bovine respiratory disease complex because of its frequency of occurrence, predilection for the lower respiratory tract, and its ability to predispose the respiratory tract to secondary bacterial infection. In outbreaks, morbidity tends to be high, and case fatality can be 0-20%. Signs include increased rectal temperature 40-42° C., depression, decreased feed intake, increased respiratory rate, cough, and nasal and lacrimal discharge. Generally, respiratory signs predominate. Dyspnea may become pronounced in the later stages of the disease. Subcutaneous emphysema is sometimes reported. Secondary bacterial pneumonia is a frequent occurrence. A biphasic disease pattern has been described but is not consistent. Gross lesions include a diffuse interstitial pneumonia with subpleural and interstitial emphysema along with interstitial edema. These lesions are similar to and must be differentiated from other causes of interstitial pneumonia. Histologic examination reveals syncytial cells in bronchiolar epithelium and lung parenchyma, intracytoplasmic inclusion bodies, proliferation and/or degeneration of bronchiolar epithelium, alveolar epithelialization, edema, and hyaline membrane formation.

Bovine Herpesvirus (BHV-1) is associated with several diseases and symptoms in cattle: Infectious bovine rhinotracheitis (IBR), infectious pustular vulvovaginitis (IPV), balanoposthitis, conjunctivitis, abortion, encephalomyelitis, and mastitis. Only a single serotype of BHV-1 is recognized; however, three subtypes of BHV-1 have been described on the basis of endonuclease cleavage patterns of viral DNA. These types are referred to as BHV-1.1 (respiratory subtype), BHV-1.2 (genital subtype), and BHV-1.3 (encephalitic subtype). Recently, BHV-1.3 has been reclassified as a distinct herpesvirus designated BHV-5. BHV-1 infections are widespread in the cattle population. In feedlot cattle, the respiratory form is most common. The viral infection alone is not life-threatening but predisposes cattle to secondary bacterial pneumonia, which may result in death. In breeding cattle, abortion or genital infections are more common. Genital infections can occur in bulls (infectious pustular balanoposthitis) and cows (IPV) within 1-3 days of mating or close contact with an infected animal. Transmission can occur in the absence of visible lesions and through artificial insemination with semen from subclinically infected bulls. Cattle with latent BHV-1 infections generally show no clinical signs when the virus is reactivated, but they do serve as a source of infection for other susceptible animals and thus perpetuate the disease. The incubation period for the respiratory and genital forms is 2-6 days. In the respiratory form, clinical signs range from mild to severe, depending on the presence of secondary bacterial pneumonia. Clinical signs include pyrexia, anorexia, coughing, excessive salivation, nasal discharge that progresses from serous to mucopurulent, conjunctivitis with lacrimal discharge, inflamed nares (hence the common name "red nose"), and dyspnea if the larynx becomes occluded with purulent material. Pustules may develop on the nasal mucosa and later form diphtheritic plaques. Conjunctivitis with corneal opacity may develop as the only manifestation of BHV-1 infection. In the absence of bacterial pneumonia, recovery generally occurs 4-5 days after the onset of clinical signs. Abortions may occur concurrently with respiratory disease but can also occur up to 100 days after infection. Abortions can occur regardless of the severity of disease in the dam. Abortions generally occur during the second half of pregnancy, but early embryonic death may also occur. The first signs of genital infections in cows are frequent urination, elevation of the tailhead, and a mild vaginal discharge. The vulva is swollen, and small papules, then erosions and ulcers, are present on the mucosal surface. If secondary bacterial infections do not occur, animals recover in 10-14 days. If bacterial infection occurs, there may be inflammation of the uterus and transient infertility, with purulent vaginal discharge for several weeks. In bulls, similar lesions occur on the penis and prepuce. BHV-1 infection can be severe in young calves and cause a generalized disease. Pyrexia, ocular and nasal discharges, respiratory distress, diarrhea, incoordination, and eventually convulsions and death may occur in a short period after generalized viral infection. IBR is rarely fatal in cattle unless complicated by bacterial pneumonia. In uncomplicated IBR infections, most lesions are restricted to the upper respiratory tract and trachea. Petechial to ecchymotic hemorrhages may be found in the mucous membranes of the nasal cavity and the paranasal sinuses. Focal areas of necrosis develop in the nose, pharynx, larynx, and trachea. The lesions may coalesce to form plaques. The sinuses are often filled with a serous or serofibrinous exudate. As the disease progresses, the pharynx becomes covered with a serofibrinous exudate, and bloodtinged fluid may be found in the trachea. The pharyngeal and pulmonary lymph nodes may be acutely swollen and hemorrhagic. The tracheitis may extend into the bronchi and bronchioles; when this occurs, epithelium is sloughed in the airways. The viral lesions are often masked by secondary bacterial infections. In young animals with generalized BHV-1 infection, erosions and ulcers overlaid with debris may be found in the nose, esophagus, and forestomachs. In addition, white foci may be found in the liver, kidney, spleen, and lymph nodes. Aborted fetuses may have pale, focal, necrotic lesions in all tissues, but which are especially visible in the liver.

A number of other Bovine Respiratory Viruses have been identified as being involved in BRD. Bovine herpesvirus-4 has been implicated in several diseases, including BRD. Bovine adenovirus has been associated with a wide spectrum of diseases, with bovine adenovirus type 3 being the serotype most often associated with BRD. Two serotypes of bovine rhinovirus have been recognized to cause respiratory tract infections in cattle. Other viruses reported to be associated with BRD include bovine reovirus, enterovirus, and coronavirus. These viruses have a role similar to the other viruses previously discussed in that, in combination with other stressors, they can serve as initiators of bacterial pneumonia. Bovine coronavirus is also commonly associated with diarrhea in calves. It replicates in the epithelium of the upper respiratory tract and in the enterocytes of the intestine, where it produces similar lesions to rotavirus but also infects the epithelial cells of the large intestine to produce atrophy of the colonic ridges. Vaccines are not available for prevention of these viral respiratory diseases.

Bovine rotavirus is the most common viral cause of diarrhea in calves. Group A and B rotavirus are involved, but group A is the most prevalent and clinically important and contains several serotypes of differing virulence. Rotavirus replicates in the mature absorptive and enzyme-producing enterocytes on the villi of the small intestine, leading to rupture and sloughing of the enterocytes with release of virus to infect adjacent cells. Rotavirus does not infect the immature cells of the crypts. With virulent strains of rotavirus, the loss of enterocytes exceeds the ability of the intestinal crypts to replace them; hence, villous height is reduced, with a consequent decrease in intestinal absorptive surface area and intestinal digestive enzyme activity.

Other viruses, including Breda virus, a calici-like virus, Adenovirus, Astrovirus and Parvovirus, have been demonstrated in the feces of calves with diarrhea and can produce diarrhea in calves experimentally. However, these agents can also be demonstrated in the feces of healthy calves. The importance of these agents in the syndrome of neonatal diarrhea has yet to be determined. *Mannheimia haemolytica* (formerly *Pasteurella haemolytica*) biotype A, serotype 1 is the bacterium most frequently isolated from the lungs of cattle with BRD. Although less frequently cultured than *M. haemolytica, Pasteurella multocida* is also an important cause of bacterial pneumonia. When pulmonary abscessation occurs, generally in association with chronic pneumonia, *Actinomyces (Arcanobacterium) pyogenes* is frequently isolated. Under normal conditions, *M. haemolytica* generally remains confined to the upper respiratory tract, in particular the tonsillar crypts, and is difficult to culture from healthy cattle. After stress or viral infection, the replication rate of *M. haemolytica* in the upper respiratory tract increases rapidly, as does the likelihood of culturing the bacterium. The increased bacterial growth rate and colonization of the lungs may be due to suppression of the host's defense mechanism related to environmental stressors or viral infections. It is during this log phase of growth that virulence factors are elaborated by *M. haemolytica*, such as an exotoxin that has been referred to as leukotoxin. The interaction between the virulence factors of the bacteria and host defenses results in tissue damage and development of pneumonia. Clinical signs of bacterial pneumonia are often preceded by signs of viral infection of the respiratory tract. With the onset of bacterial pneumonia, the severity of clinical signs increases and are characterized by depression and toxemia. There will be pyrexia (40-41° C.); serous to mucopurulent nasal discharge; moist cough; and a rapid, shallow respiratory rate. Auscultation of the cranioventral lung field reveals increased bronchial sounds, crackles, and wheezes. In severe cases, pleurisy may develop, which is characterized by an irregular breathing pattern and grunting on expiration. The animal will become unthrifty in appearance if the pneumonia becomes chronic, which is usually associated with the formation of pulmonary abscesses. *M. haemolytica* causes a severe, acute fibrinous pneumonia or fibrinonecrotic pneumonia. The pneumonia has a bronchopneumonic pattern. Grossly, there is extensive reddish black to greyish brown cranioventral regions of consolidation with gelatinous thickening of interlobular septa and fibrinous pleuritis. There are extensive thromboses, foci of lung necrosis, and limited evidence of bronchitis and bronchiolitis. *P. multocida* is associated with a less fulminating fibrinous to fibrinopurulent bronchopneumonia. In contrast to *M. haemolytica*, *P. multocida* is associated with only small amounts of fibrin exudation, some thromboses, limited lung necrosis, and suppurative bronchitis and bronchiolitis.

*Haemophilus somnus* (recently reclassified as *Histophilus somni*) is being increasingly recognized as an important pathogen in BRD; these bacteria are normal inhabitants of the nasopharynx of cattle. *H. somnus* infection of the lungs results in purulent bronchopneumonia that may be followed by septicemia and infection of multiple organs. Occasionally, *H. somnus* is associated with extensive pleuritis. *H. somnus* can cause an acute, usually fatal, septicemic disease that can involve the nervous, musculoskeletal, circulatory, and respiratory systems, either singly or together. The reproductive system is often affected but usually without the other systems being clinically involved. The disease may be characterized by fever, severe depression, ataxia, weakness, blindness, coma, and death within several hours to several days. It occurs sporadically in individual beef and dairy cattle and is found nearly worldwide. *H. somnus* is a gram-negative, nonmotile, nonsporeforming, pleomorphic coccobacillus that requires an enriched medium and a microaerophilic atmosphere for culture. It appears to be identical to *Histophilus ovis* and *Haemophilus agni*, etiologic agents of ovine septicemia, mastitis, and epididymitis; however, transmission of *H. somnus* between sheep and cattle has not been demonstrated. Pathogenic and nonpathogenic strains have been differentiated by intracisternal inoculation of young calves with organisms from various sources. Pathogenic and nonpathogenic strains of *H. somnus* are carried in the sheath and prepuce of males, the vagina of female cattle, and in the nasal passages of both sexes. The organism may colonize the respiratory tract, presumably after inhalation, and is frequently found in urine. Prevalence of the organism in cattle is probably high because high titers of specific antibodies are found in a large proportion of tested cattle. Several disease syndromes caused by *H. somnus* have been recognized, including thrombomeningoencephalitis, fibrinopurulent bronchopneumonia, fibrinous pleuritis, and polyarthritis. Myocardial and skeletal muscle necroses occur. Suppurative vaginitis, cervicitis, and endometritis have been documented in cows infected experimentally and naturally after breeding, and the organism is a cause of sporadic abortion. Strains of *H. somnus* that cause disease adhere to the endothelium of vessels, resulting in contraction, exposure of collagen, platelet adhesion, and thrombosis. TME results when this occurs in the brain and associated membranes, after invasion of the organism into the bloodstream of susceptible cattle. Strains may adhere to endothelium in vessels of the pleura, myocardium, synovium, or a variety of other tissues and produce inflammation in those sites (e.g., infections of the larynx and middle ear have been recorded). The susceptibility of individual animals and variations in the preference of strains of the organism for vessels in different tissues may be important in the development of the form of disease, but the mechanisms involved are incompletely understood. Reproductive problems may not necessarily be preceded by bacteremia, but the pathogenesis is poorly defined. A fever as high as 42° C. is often the first sign of disease; however, this usually falls to normal or subnormal within hours. Other findings are determined by the system(s) involved and may include rapid respiration, stiffness, knuckling at the fetlocks, severe depression, ataxia, paralysis, and opisthotonos, followed by coma and death within several hours. Affected animals may be blind, and retinal hemorrhages with grey foci of retinal necrosis are sometimes seen. Signs such as hypersensitivity, convulsions, excitement, nystagmus, and circling occur inconsistently and may be related to the regions of the CNS affected in the course of disease development. Occasionally, animals are found dead, indicating a rapidly fatal course. A marked change in the total and differential WBC count is common; leukopenia and neutropenia occur in severe, usually acute, fatal disease, while neutrophilia may be present in less severe disease. In TME, the total cell count of the CSF is markedly increased, and neutrophils predominate. During septicemia, the organism can be recovered from blood, synovial fluid, CSF, brain, kidneys, urine, and a variety of other organs. The lesions are characterized by vascular thrombosis and infarction of the surrounding tissue. Randomly distributed red to brown foci of necrosis with hemorrhage on the surface and cut sections of the brain and spinal cord, retina, skeletal muscle, myocardium, kidney, intestine, and spleen are characteristic. A fibrinopurulent meningitis with cloudy CSF may sometimes be seen on the surface of the brain and spinal cord, and a polyserositis, especially of joints and pleura, may occur. An acute fibrinous bronchopneumonia with tissue necrosis may develop after airborne infections.

Except for *M. bovis*, the exact role of *mycoplasmas* and *ureaplasmas* in BRD requires better definition. *Mycoplasmas* can be recovered from the respiratory tract of nonpneumonic calves, but the frequency of isolation is greater in those with respiratory tract disease. The *mycoplasmas* commonly recovered from the lungs of pneumonic calves include *Mycoplasma dispar, Ureaplasma* spp. Experimental infections usually result in unapparent to mild signs of respiratory disease. This does not preclude a synergistic role for *mycoplasmas* in conjunction with viruses and bacteria in BRD. Lesions described include peribronchial and peribronchiolar lymphoid cuffing and alveolitis. Culture of these organisms requires special media and conditions and may take up to a week for growth of the organisms.

Chlamydiae have been identified in various parts of the world as a cause of enzootic pneumonia in calves. The causative agent is *Chlamydia psittaci*. Some respiratory isolates from calves have properties of immunotypes 1 and 6 and are similar to strains recovered from intestinal infections and abortions of cattle and sheep. Immunotype 6 has been recovered from pneumonic lungs of calves and pigs. Thus, the GI tract must be considered as an important site in the pathogenesis of chlamydial infections and as a natural reservoir and source of the organisms. Chlamydial pneumonia has affected calves under a whole range of conditions, including dairy farms. A synergism between *Chlamydia* and *P. haemolytica* has been demonstrated experimentally. Calves with chlamydial pneumonia are usually febrile, lethargic, and dyspneic, and have a serous and later mucopurulent nasal discharge and a dry hacking cough. Calves of weanling age are affected most frequently, but older cattle may also show signs of infection. The acute pulmonary lesion is a bronchointerstitial pneumonia. The anteroventral parts of the lungs are affected but, in severe cases, entire lobes can be involved. The dry cough is attributed to tracheitis. Microscopic changes in the lungs include suppurative bronchitis and alveolitis progressing to type II pneumocyte hyperplasia and interstitial thickening.

Bovine genital campylobacteriosis is a venereal disease of cattle characterized primarily by early embryonic death, infertility, a protracted calving season, and occasionally, abortion. Distribution is probably worldwide. The cause is the motile, gram-negative, curved or spiral, polar flagellated bacterium *Campylobacter fetus venerealis* or *Campylobacter fetus fetus*. For many years, it was thought that *C. fetus fetus* (formerly *C. fetus intestinalis*) was generally an intestinal organism, only occasionally caused abortion in cattle, and was not a cause of infertility. However, it has been shown that *C. fetus fetus* can also be a significant cause of the classic infertility syndrome usually attributed to *Campylobacter fetus venerealis*. There are several strains of *C. fetus fetus*, and the only way to determine if a strain is a cause of infertility is to test that possibility in a group of heifers. *Campylobacter* spp are very labile and are destroyed quickly by heating, drying, and exposure to the atmosphere. Unless cultured quickly after collection from the animal and grown under microaerophilic or anaerobic conditions, campylobacters will not grow. *Campylobacter fetus* is transmitted venereally and also by contaminated instruments, bedding, or by artificial insemination using contaminated semen. Individual bulls vary in their susceptibility to infection because some become permanent carriers, while others appear to be resistant to infection. Bulls can also transmit the infection mechanically for several hours after copulating with an infected cow. In cows, the duration of the carrier state is also variable; some clear the infection rapidly, while others can carry *C. fetus* for ≥2 yr. IgA antibodies are shed in cervical mucus in significant amounts in ~50% of cows for several months after infection and are useful diagnostically. Although most of the genital tract may be free of infection when a cow eventually conceives, the vagina may remain chronically infected, even through pregnancy. Cows are systemically normal, but there is are variable degrees of mucopurulent endometritis that causes early embryonic death, prolonged luteal phases, irregular estrous cycles, repeat breeding and, as a result, protracted calving periods. Observed abortions are not common. In herds not managed intensively, disease may be noticed only when pregnancy examinations reveal low or marginally low pregnancy rates but, more importantly, great variations in gestation lengths, especially when the disease has recently been introduced to the herd. In subsequent years, infertility is usually confined to replacement heifers and a few susceptible cows. Bulls are asymptomatic and produce normal semen.

Leptospirosis is a contagious disease of animals, including man, caused by various immunologically distinct leptospiral serovars, most of which are regarded as subgroups of *Leptospira interrogans*. Infections may be asymptomatic or cause various signs, including fever, icterus, hemoglobinuria, renal failure, infertility, abortion, and death. After acute infection, leptospires frequently localize in the kidneys or reproductive organs and are shed in the urine, sometimes in large numbers for months or years. Because the organisms survive in surface waters for extended periods, the disease is often waterborne. In the U.S. the disease is primarily due to the serovars *Leptospira hardjo, Leptospira interrogans* serovar *hardjo* (*hardjo Prajitno*), *L. borgpetersenii* serovar *hardjo* (*hardjo Bovis*), *Leptospira pomona*, and *Leptospira grippotyphosa*. However, *Leptospira canicola* and *Leptospira icterohaemorrhagiae* serovars also have been isolated. Calves may have fever, anorexia, and dyspnea, and in *Leptospira pomona* infections, icterus, hemoglobinuria, and anemia. Body temperature may rise suddenly to 40.5-41° C. Hemoglobinuria rarely lasts longer than 48-72 hrs. Icterus clears rapidly and is followed by anemia. The RBC's begin to increase in number by 4-5 days and return to normal 7-10 days later. However, *Leptospira hardjo* infections usually do not cause hemolytic anemia, which makes diagnosis more difficult. Morbidity and mortality are higher in calves than in adult cattle. In older cattle, signs vary greatly and diagnosis is more difficult. Enzootic *Leptospira hardjo* infections, which usually result in abnormal milk, are more obvious in dairy than in beef cattle. Signs usually are restricted to lowered milk and calf production; a hemolytic crisis does not occur. The milk is thick, yellow, and blood-tinged; it may contain clots, although there is little evidence of mammary inflammation. Milk production returns to normal in 10-14 days, even in the absence of treatment. Abortion and stillbirths, which are common in *Leptospira pomona* infections and sporadic in *Leptospira hardjo* infections, generally occur 3-10 weeks after initial infection. The abortions are more common during the third trimester. An abortion storm in a breeding herd is often the first indication that leptospirosis exists, because the mild initial signs often pass unnoticed. In endemically infected herds, abortions occur mostly in younger animals and are sporadic, rather than being manifested as abortion storms. Calves reared by previously infected cows are protected by colostral antibodies for up to 6 months. The calves generally have an antibody titer similar to that of their dams. In the acute form, anemia, icterus, hemoglobinuria, and submucosal hemorrhages are prominent. The kidneys are swollen, with multifocal petechial and ecchymotic hemorrhages that become pale with time. The liver may be swollen, with minute areas of focal necrosis. Petechiae in other organs are seen in fulminating cases; however, in the more prevalent *Leptospira hardjo* infections, the lesions are primarily restricted to the kidneys.

Brucellosis is caused by bacteria of the genus *Brucella* and is characterized by abortion, retained placenta, and to a lesser extent, orchitis and infection of the accessory sex glands in males. The disease in cattle, water buffalo, and bison is caused almost exclusively by *Brucella abortus*; however, *Brucella suis* or *Brucella melitensis* is occasionally implicated in some cattle herds. *Brucella suis* does not appear to be contagious from cow to cow. *Brucella abortus* Infection spreads rapidly and causes many abortions in unvaccinated herds. Typically, in a herd in which disease is endemic, an infected cow aborts only once after exposure; subsequent gestations and lactations appear normal. After exposure, many cattle become bacteremic for a short period and develop agglutinins and other antibodies; others resist infection, and a small percentage of infected cows recover. A positive serum agglutination test usually precedes abortion or a normal parturition but may be delayed in ~15% of animals. The incubation period may be variable and is related to the stage of gestation at the time of exposure. Organisms are shed in milk and uterine discharges, and the cow may become temporarily sterile. Bacteria may be found in the uterus during pregnancy, uterine involution, and infrequently, for a prolonged time in the nongravid uterus. Shedding from the vagina largely disappears with reduction of the fluids after parturition. Some infected cows that aborted previously shed brucellae from the uterus at subsequent normal parturitions. Organisms are shed in milk for a variable length of time—in most cattle for life. Natural transmission occurs by ingestion of organisms, which are present in large numbers in aborted fetuses, fetal membranes, and uterine discharges. Cattle may ingest contaminated feed and water, or lick contaminated genitals of other animals. Venereal transmission by infected bulls to susceptible cows appears to be rare. Transmission may occur by artificial insemination when *Brucella*-contaminated semen is deposited in the uterus but, reportedly, not when deposited in the midcervix. Brucellae may enter the body through mucous membranes, conjunctivae, wounds, or even intact skin. Mechanical vectors (eg, other animals, including man) may spread infection. Brucellae have been recovered from fetuses and from manure that has remained in a cool environment for >2 mo. Exposure to direct sunlight kills the organisms within a few hours. Abortion is the most obvious manifestation. Infections may also cause stillborn or weak calves, retained placentas, and reduced milk yield. Usually, general health is not impaired in uncomplicated abortions. Seminal vesicles, ampullae, testicles, and epididymides may be infected in bulls; therefore, organisms are in the semen. Agglutinins may be demonstrated in seminal plasma from infected bulls. Testicular abscesses may occur. Long-standing infections may result in arthritic joints in some cattle.

Clostridia are relatively large, anaerobic, spore-forming, rod-shaped organisms. The spores are oval, sometimes spherical, and are central, subterminal, or terminal in position. The vegetative forms of clostridia in tissue fluids of infected animals occur singly, in pairs, or rarely in chains. Differentiation of the various pathogenic and related species is based on cultural characteristics, spore shape and position, biochemical reactions, and the antigenic specificity of toxins or surface antigens. The natural habitats of the organisms are the soil and intestinal tract of animals, including man. Pathogenic strains may be acquired by susceptible animals either by wound contamination or by ingestion. Diseases thus produced are a constant threat to successful livestock production in many parts of the world.

*Clostridium haemolyticum* is a soil-borne organism that may be found naturally in the GI tract of cattle. It can survive for long periods in contaminated soil or in bones from carcasses of animals that had been infected. After ingestion, latent spores ultimately become lodged in the liver. The incubation period is extremely variable, and the onset depends on the presence of a locus of anaerobiosis in the liver. Such a nidus for germination is most often caused by fluke infection, much less often by high nitrate content of the diet, accidental liver puncture, liver biopsy, or any other cause of localized necrosis. When conditions for anaerobiosis are favorable, the spores germinate, and the resulting vegetative cells multiply and produce β toxin (phospholipase C), which causes intravascular hemolysis and its sequelae, including hemolytic anemia and hemoglobinuria. Cattle may be found dead without premonitory signs. Usually, there is a sudden onset of severe depression, fever, abdominal pain, dyspnea, dysentery, and hemoglobinuria. Anemia and jaundice are present in varying degrees. Edema of the brisket may occur. Hgb and RBC levels are quite low. The duration of clinical signs varies from ~12 hr in pregnant cows to ~3-4 days in other cattle. The mortality in untreated animals is ~95%. Some cattle suffer from subclinical attacks of the disease and thereafter act as immune carriers. Dehydration, anemia, and sometimes subcutaneous edema are present. There is bloody fluid in the abdominal and thoracic cavities. The lungs are not grossly affected, and the trachea contains bloody froth with hemorrhages in the mucosa. The small intestine and occasionally the large intestine are hemorrhagic; their contents often contain free or clotted blood. An anemic infarct in the liver is virtually pathognomonic; it is slightly elevated, lighter in color than the surrounding tissue, and outlined by a bluish red zone of congestion. The kidneys are dark, friable, and usually studded with petechiae. The bladder contains purplish red urine. After death, rigor mortis sets in more rapidly than usual.

*Clostridium chauvoei* occurs naturally in the intestinal tract of animals. It probably can remain viable in the soil for many years, although it does not actively grow there. Contaminated pasture appears to be a source of organisms. Outbreaks of blackleg have occurred in cattle on farms in which recent excavations have occurred, which suggests that disturbance of soil may activate latent spores. The organisms probably are ingested, pass through the wall of the GI tract, and after gaining access to the bloodstream, deposited in muscle and other tissues. In cattle, blackleg infection is endogenous, in contrast to malignant edema. Lesions develop without any history of wounds, although bruising or excessive exercise may precipitate some cases. Commonly, the animals that contract blackleg are of the beef breeds, in excellent health, gaining weight, and usually the best animals of their group. Outbreaks occur in which a few new cases are found each day for several days. Most cases occur in cattle from 6 months to 2 years old, but thrifty calves as young as 6 weeks and cattle as old as 10-12 years may be affected. The disease usually occurs in summer and fall and is uncommon during the winter. In sheep, the disease is not restricted to the young, and most cases follow some form of injury such as shearing cuts, docking, crutching, or castration. Usually, onset is sudden and a few cattle may be found dead without premonitory signs. Acute lameness and marked depression are common. Initially, there is a fever but, by the time clinical signs are obvious, the temperature may be normal or subnormal. Characteristic edematous and crepitant swellings develop in the hip, shoulder, chest, back, neck, or elsewhere. At first, the swelling is small, hot, and painful. As the disease rapidly progresses, the swelling enlarges, there is crepitation on palpation, and the skin becomes cold and insensitive as the blood supply to the area diminishes. General signs include prostration and tremors. Death occurs in 12-48 hrs. In some cattle, the lesions are restricted to the myocardium and the diaphragm, with no reliable ante mortem evidence of the localized lesion.

*Clostridium novyi* has been suspected but not yet confirmed as a cause of sudden death in cattle and pigs fed high-level grain diets, and in which pre-existing lesions of the liver were not detectable. The lethal and necrotizing toxins (primarily α toxin) damage hepatic parenchyma, thereby permitting the bacteria to multiply and produce a lethal amount of toxin. Usually, death is sudden with no well-defined signs. Affected animals tend to lag behind the flock, assume sternal recumbency, and die within a few hours. Most cases occur in the summer and early fall when liver fluke infection is at its height. The disease is most prevalent in 1- to 4-year-old sheep and is limited to animals infected with liver flukes. Differentiation from acute fascioliasis may be difficult, but peracute deaths of animals that show typical lesions on necropsy should arouse suspicion of infectious necrotic hepatitis. The most characteristic lesions are the greyish yellow necrotic foci in the liver that often follow the migratory tracks of the young flukes. Other common findings are an enlarged pericardial sac filled with straw-colored fluid, and excess fluid in the peritoneal and thoracic cavities. Usually, there is extensive rupture of the capillaries in the subcutaneous tissue, which causes the adjacent skin to turn black (hence the common name, black disease).

*Clostridium septicum* is found in soil and intestinal contents of animals (including man) throughout the world. Infection ordinarily occurs through contamination of wounds containing devitalized tissue, soil, or some other tissue-debilitant. Wounds caused by accident, castration, docking, unsanitary vaccination, and parturition may become infected. General signs, such as anorexia, intoxication, and high fever, as well as local lesions, develop within a few hours to a few days after predisposing injury. The local lesions are soft swellings that pit on pressure and extend rapidly because of the formation of large quantities of exudate that infiltrates the subcutaneous and intramuscular connective tissue of the affected areas. The muscle in such areas is dark brown to black. Accumulations of gas are uncommon. Severe edema of the head of rams occurs after infection of wounds inflicted by fighting. Malignant edema associated with lacerations of the vulva at parturition is characterized by marked edema of the vulva, severe toxemia, and death in 24-48 hours. Similarity to blackleg is marked, and differentiation made on necropsy is unreliable; laboratory confirmation is the only certain procedure. Horses and pigs are susceptible to malignant edema but not to blackleg.

Infectious disease caused by *Clostridium sordellii* is also manifested as malignant edema in cattle, and also characterized by a nongaseous, nonhemorrhagic, edematous swelling of the head, face, and neck of young rams. This infection is initiated in young rams by their continual butting of one another. The bruised and battered subcutaneous tissues provide conditions suitable for growth of pathogenic clostridia, and the breaks in the skin offer an opportunity for their entrance Infection with *C. perfringens* types A, B and C causes severe enteritis, dysentery, toxemia, and high mortality in young calves. Types B and C both produce the highly necrotizing and lethal β toxin that is responsible for the severe intestinal damage. This toxin is sensitive to proteolytic enzymes, and disease is associated with inhibition of proteolysis in the intestine. Sow colostrum, which contains a trypsin inhibitor, has been suggested as a factor in the susceptibility of young piglets. Type C also causes enterotoxemia in adult cattle. In calves, there is acute diarrhea, dysentery, abdominal pain, convulsions, and opisthotonos. Death may occur in a few hours, but less severe cases survive for a few days, and recovery over a period of several days is possible. Hemorrhagic enteritis with ulceration of the mucosa is the major lesion in all species. Grossly, the affected portion of the intestine is deep blue-purple and appears at first glance to be an infarction associated with mesenteric torsion. Smears of intestinal contents can be examined for large numbers of gram-positive, rod-shaped bacteria, and filtrates made for detection of toxin and subsequent identification by neutralization with specific antiserum.

This classic enterotoxemia caused by *C. perfringens* type D rarely occurs in cattle. It is worldwide in distribution and may occur in animals of any age. The disease has been suspected in well-nourished beef calves nursing high-producing cows grazing lush pasture and in sudden death syndrome in feedlot cattle; however, supportive laboratory evidence in the latter is lacking. Acutely affected calves not found dead show mania, convulsions, blindness, and death in a few hours. Subacutely affected calves are stuporous for a few days and may recover.

Tetanus toxemia is caused by a specific neurotoxin produced by *Clostridium tetani* in necrotic tissue. Almost all mammals are susceptible to this disease. Although tetanus is worldwide in distribution, there are some areas, such as the northern Rocky Mountain section of the USA, where the organism is rarely found in the soil and where tetanus is almost unknown. In general, the occurrence of *C. tetani* in the soil and the incidence of tetanus in man and horses is higher in the warmer parts of the various continents. *Clostridium tetani*, an anaerobe with terminal, spherical spores, is found in soil and intestinal tracts. In most cases, it is introduced into the tissues through wounds, particularly deep puncture wounds, which provide a suitable anaerobic environment.

Infection with *Salmonella* spp can produce diarrhea in animals of all ages, especially those that are stressed, closely stocked, or exposed to a heavily contaminated feed or water supply. Salmonellosis is caused by many species of salmonellae and characterized clinically by one or more of three major syndromes—septicemia, acute enteritis, and chronic enteritis. The incidence has increased with the intensification of livestock production. Young calves usually develop the septicemic form. Adult cattle develop acute enteritis. Chronic enteritis may develop occasionally in cattle. Pregnant animals may abort. In older animals, the disease is manifested by dysentery and toxemia, and mortality can be significant. While many other *Salmonella* spp may cause disease, the more relevant in cattle are *S. typhimurium*, *S. dublin*, and *S. newport*. Although their resulting clinical patterns are not distinct, different species of salmonellae tend to differ in their epidemiology. Plasmid profile and drug-resistance patterns are sometimes useful markers for epidemiologic studies. Feces of infected animals can contaminate feed and water, milk, fresh and processed meats from abattoirs, plant and animal products used as fertilizers or feedstuffs, pasture and rangeland, and many inert materials. The organisms may survive for months in wet, warm areas such as in feeder pig barns or in water dugouts but survive less than 1 week in composted cattle manure. Rodents and wild birds also are sources of infection. The prevalence of infection varies among species and countries and is much higher than the incidence of clinical disease, which is commonly precipitated by stressful situations such as sudden deprivation of feed, transportation, drought, crowding, parturition, and the administration of some drugs.

Further relevant gastro-intestinal pathogens are *Escherichia coli*, *Cryptosporidium parvum* and *Mycobacterium avium paratuberculosis*. *Escherichia coli* infection causes severe intestinal disease in young animals characterized as neonatal diarrhea, post weaning diarrhea, edema disease, and/or septicemia depending upon the virulence factors present in the strain causing the infection. Calves infected with pathogenic *E. coli* can develop severe diarrhea causing fatal dehydration, or fatal septicemic infections. Paratuberculosis is a chronic contagious enteritis characterized by persistent and progressive diarrhea, weight loss, debilitation, and eventually death. It affects cattle, sheep, goats, llamas, camels, farmed deer, and other domestic, exotic, and wild ruminants. It has also been recognized in wild rabbits; horses and pigs can be infected experimentally. Distribution is worldwide.

There are conflicting data on the involvement of the organism in Crohn's disease, a chronic enteritis in people. Animals with paratuberculosis should be considered as potential zoonotic risks until the situation is clarified. The causative organism is *Mycobacterium avium paratuberculosis*, formerly known as *M. paratuberculosis* or *M. johnei*. Occasionally, other *M. avium* subspecies are isolated from cases. The organism is quite resistant and can survive on pasture for more than 1 year, but sunlight, alkaline soils, and drying reduce its survival rate. It is shed in large numbers in feces of infected animals, and infection is acquired by ingestion of contaminated feed and water. Introduction of the disease into a clean herd is usually by subclinically infected carriers. Infection is acquired early in life, but clinical signs rarely develop in cattle <2 years old. Resistance increases with age, and cattle first exposed as adults are unlikely to become infected. Most calves are infected soon after birth either by nursing udders contaminated with feces from infected animals or by being housed in contaminated pens. The organism can also be present in colostrum and milk of infected cows, and intrauterine infections have also been described. After ingestion, the bacteria infect macrophages in the mucosa of the lower small intestine and in associated lymph nodes. Most animals will eliminate infection by an early cell-mediated immune response that encourages microbicidal activity in macrophages. In susceptible animals, the organisms multiply and provoke a chronic enteritis that leads to clinical disease. This may take months to years to develop and is usually paralleled by a decline in cell-mediated immunity and a rise in ineffective serum antibody. However, fecal shedding begins before clinical signs are apparent. *Mycobacterium avium paratuberculosis* can be isolated from feces, mesenteric and ileocecal lymph nodes, thickened intestinal walls, and less frequently the udder and the reproductive tracts of both sexes.

Cryptosporidiosis is an enterocolitis of cosmopolitan distribution caused by the coccidian parasite *Cryptosporidium parvum*. It is not host-specific and is common in young ruminants, particularly calves; it is also found in man and pigs and is rare in dogs, cats, and horses. Other cryptosporidia cause disease in reptiles and birds. The disease in calves, characterized by weight loss and watery diarrhea, is clinically indistinguishable from many other causes of calf diarrhea. *Cryptosporidium parvum* is a minute protozoan that is transmitted by the fecal-oral route. Oocysts are sporulated (four sporozoites) when shed in the feces and, therefore, are immediately infective. The mean incubation period is ~4 days. Calves 1-3 weeks old seem to be most susceptible. Signs such as anorexia, weight loss, diarrhea, and tenesmus, resemble those caused by several other intestinal pathogens; however, infections without signs do occur. Uncomplicated cryptosporidiosis is seldom fatal. Disease can be severe in immunocompromised individuals. If severe disease in calves is seen, other disease agents or concurrent infections should be ruled out. Although *C. parvum* can infect virtually the entire intestinal tract, the distal small intestine usually is affected most severely. Infection in horses is limited to the small intestine. Gross lesions may consist of hyperemic intestinal mucosa and yellowish intestinal contents. Microscopically, mild to severe villous atrophy with spherical organisms in the brush border is evident. Unlike *Eimeria* and *Isospora* spp, which are intracellular parasites, *C. parvum* is intramembranous and resides within the brush border of the intestinal epithelial cells.

Inflammation of the mammary gland (mastitis) is almost always due to the effects of infection by bacterial or mycotic pathogens. Mastitis may be associated with infection by many other organisms, including *Streptococcus uberis, Streptococcus dysgalactiae, Streptococcus agalactiae, Staphylococcus aureus, Escherichia coli, Klebsiella* spp. *Pseudomonas aeruginosa, Actinomyces pyogenes, Mycoplasma* spp, *Nocardia asteroides, Serratia, Mycobacterium* spp, *Clostridium perfringens, Pasteurella* spp, yeasts, and *Prototheca* spp.

Dermatomycoses (Dermatophytosis) in animals are anthropozoonotic diseases of the skin and related tissue. Clinical symptoms are characterized by loss of hair in the affected area, hyperemia, scaling and asbestos-like scabs. Inflammation is often accompanied by suppuration. Dermatomycoses are often also characterized by localized infection of the skin. Dermatomycoses in animals carry a substantial socioeconomic impact. Diseased animals required prolonged treatment and can spread infection to both animals and humans. Dermatophytosis are caused by mycosis infections of *Trichophyton* spp. or *Microsporum* spp. Most relevant causes for cattle are *Trichophyton verrucosum, Trichophyton mentagrophytes* or *Trichophyton sarkisovii*.

An infection of the lower respiratory tract, usually resulting in bronchitis or pneumonia, can be caused by any of several parasitic nematodes, including *Dictyocaulus viviparus* in cattle. This lungworm belongs to the superfamily Trichostrongyloidea and has direct life cycles. The cattle lungworm is common in northwest Europe and is the cause of severe outbreaks of "husk" or "hoose" in young grazing cattle. Because *D. viviparus* infection in cattle is the most economically important, it has been most investigated and many of the observations from it are applicable to the other species. Clinical disease usually develops on first exposure to sufficient infective larvae. In cattle, this usually occurs during their first season at pasture; however, an increase in the number of older cattle affected has been reported. Signs of lungworm infection range from moderate coughing with slightly increased respiratory rates to severe persistent coughing and respiratory distress and even failure. Reduced weight-gains, reduced milk yields, and weight loss accompany many infections in cattle. Patent subclinical infections can occur in all species. The most consistent signs in cattle are tachypnea and coughing.

Trichomoniasis is a venereal protozoal disease of cattle characterized primarily by early fetal death and infertility, resulting in extended calving intervals. Distribution is probably worldwide. The causative protozoan, *Trichomonas (Tritrichomonas) foetus*, is pyriform and ordinarily 10-15×5-10 μm, but there is considerable pleomorphism. It may become spherical when cultured in artificial media. At its anterior end, there are three flagella about the same length as the body of the parasite. An undulating membrane extends the length of the body and is bordered by a marginal filament that continues beyond the membrane as a posterior flagellum. Although *T. foetus* can survive the process used for freezing semen, it is killed by drying or high temperatures. *Trichomonas foetus* is found in the genital tracts of cattle. When cows are bred naturally by an infected bull, 30-90% become infected, suggesting that strain differences exist. Variation in breed susceptibility to trichomoniasis may also exist. Bulls of all ages can remain infected indefinitely but this is less likely in younger males. By contrast, most cows are free of infection within 3 months after breeding. However, immunity is not long lasting and reinfection does occur. Transmission can also occur when the semen from infected bulls is used for artificial insemination. The most common sign is infertility caused by embryonic death. This results in repeat breeding and a prolonged calving season. Fetal death and abortions can also occur but are not as common as losses earlier in gestation. *Trichomonas foetus* has been found in vaginal cultures taken as late as 8 months of gestation and, apparently, live calves can be born to infected dams. Pyometra occasionally develops after breeding.

*Neospora caninum* is an obligate intracellular protozoan parasite that has been confused previously with *Toxoplasma gondii*. Only asexual stages are known, and they resemble *T. gondii*. The complete life cycle of *N. caninum* is unknown, but it can be transmitted transplacentally in dogs, cattle, goats, sheep, and cats, and subsequent offspring may be affected. Tachyzoites are 5-7×1-5 μm, depending on the stage of division. They divide by endodyogeny. Tachyzoites are found in myocytes, neural cells, dermal cells, macrophages, and other cells. Tissue cysts up to 100 μm in diameter are found in neural cells; the cyst wall is amorphous and up to 4 μm thick. Cysts have no septa and enclose slender 7×1.5 μm bradyzoites. In dairy cattle, *N. caninum* is a major cause of abortion in many countries, particularly in the USA. Calves may be aborted, stillborn, born underweight, weak, or paralyzed, or they may become paralyzed within 4 weeks of birth. Non-suppurative encephalitis is the main lesion in aborted fetal tissues. Abortion can occur throughout gestation, and some cows may abort again; dams of these calves are clinically normal.

Babesiosis is caused by intraerythrocytic protozoan parasites of the genus *Babesia*. A wide range of domestic and wild animals and occasionally man is affected by the disease, which is transmitted by ticks and has a worldwide distribution. Two important species in cattle—*Babesia bigemina* and *Babesia bovis*—are widespread in tropical and subtropical areas and are the focus of this discussion. In endemic areas, two features are important in determining the risk of clinical disease: 1) calves have a degree of immunity (related both to colostral-derived antibodies and to age) that persists for ~6 months, and 2) animals that recover from *Babesia* infections are immune for life. Thus, at high levels of tick transmission, all newborn calves will become infected with *Babesia* by 6 mos. of age, show few if any clinical signs, and subsequently be immune. This situation of endemic stability can be upset by either a natural (eg, climatic) or artificial (eg, acaricide treatment) reduction in tick numbers to levels where tick transmission of *Babesia* to calves is insufficient to ensure all are infected during this critical early period. Other circumstances that can lead to clinical outbreaks include the introduction of susceptible cattle to endemic areas and the incursion of *Babesia*-infected ticks into previously tick-free areas. Strain variation in immunity has been demonstrated but is probably not of significance in the field. The acute disease generally runs a course of ~1 week. The first sign is fever (frequently 41° C. or higher), which persists throughout, and is accompanied later by inappetence, increased respiratory rate, muscle tremors, anemia, jaundice, and loss of weight with hemoglobinemia and hemoglobinuria in the final stages. CNS involvement due to sludging of parasitized erythrocytes in brain capillaries occurs frequently with *B. bovis* infection. Either constipation or diarrhea may be present. Pregnant cows often abort. With virulent strains of *B. bovis*, a hypotensive shock syndrome, combined with generalized non-specific inflammation, coagulation disturbances, and erythrocytic stasis in capillaries, contribute to the pathogenesis. With most strains of *B. bigemina*, the pathogenic effects relate more directly to erythrocyte destruction. Animals that recover from the acute disease remain infected for a number of years with *B. bovis* and for a few months in the case of *B. bigemina*. No signs are apparent during this carrier state. Lesions include an enlarged and friable spleen; a swollen liver with an enlarged gallbladder containing thick granular bile; congested, dark-colored kidneys; and generalized anemia and jaundice. The urine is often, but not invariably, red. Other organs, including the brain and heart, may show congestion or petechial hemorrhages. The susceptibility of cattle breeds to *Babesia* infections varies; for example, Brahman cattle are more resistant to *B. bovis* infection than are British breeds.

What is needed in the art is an immunogenic composition effective for eliciting an immunological response against *M. bovis* and at least one further cattle relevant pathogen. What is further needed is an immunogenic composition effective for lessening the severity of or reducing the incidence of signs of microbiological infections of cattle, caused by *M. bovis* and one or more other cattle relevant pathogen(s). What is still further needed is a vaccine effective for reducing or eliminating the incidence of signs of microbiological infections of cattle caused by *M. bovis* and one or more cattle relevant pathogen(s). What is still further needed is a method of treatment and/or prophylaxis of infections of cattle caused by *M. bovis* and one or more further cattle relevant pathogen(s) comprising a co-administration of *M. bovis* antigen and an immunologically active component of one or more cattle relevant pathogen(s). The co-administration may occur by the administration of two or more immunogenic compositions, each comprising one or more of the cattle relevant antigens including the *M. bovis* antigen, or by administration of a fixed-dose immunogenic composition comprising all the cattle relevant antigens, including the *M. bovis* antigen.

SUMMARY OF THE INVENTION

The present invention relates to combination vaccines and/or the combined use of immunogenic compositions for the treatment and/or prophylaxis of cattle against microbiological infections, wherein the infections are caused by *M. bovis* and at least one further cattle relevant pathogen. The combination vaccine as described herein comprises at least one *M. bovis* antigen, preferably the attenuated, avirulent *M. bovis* as provided herewith and one further immunologically active component effective for the treatment and/or prophylaxis of infections caused by a further pathogen of cattle. The combined use or the method of co-administration of two or more antigens of pathogens affecting cattle comprises administering a first immunogenic composition comprising a *M. bovis* antigen, preferably the attenuated, avirulent *M. bovis*, as provided herewith, and at least one further immunologically active component effective for the treatment and/or prophylaxis of infections caused by a further pathogen of cattle.

According to a further aspect, the present invention relates to a combination vaccine and/or the combined use of immunogenic compositions for the treatment and/or prophylaxis of cattle against infections of the respiratory and/or reproductive system. The combination vaccine comprises the attenuated, avirulent *M. bovis* as described herein and at least one further immunologically active component effective for the treatment and/or prophylaxis of infections caused by Bovine Viral Diarrhea virus (BVDV), Bovine Herpes virus (BHV), Bovine Respiratory Syncytial Virus (BRSV), Parainfluenza Virus (PI-3), *Campylobacter fetus*, *Leptospira canicola*, *Leptospira grippotyphosa*, *Leptospira borgpetersenii*, *Leptospira prajitno*, *Leptospira icterohaemmorrhagiae*, *Leptospira hardjo*, *Leptospira bovis*, *Leptospira interrogans* and/or *Leptospira ponoma*. The combined use or the method of co-administration of two or more antigens of pathogens affecting cattle comprises administering a first immunogenic composition comprising a *M. bovis* antigen, preferably the attenuated, avirulent *M. bovis* as provided herewith and at least one further immunologically active component effective for the treatment and/or prophylaxis of infections caused by Bovine Viral Diarrhea virus (BVDV), Bovine Herpes virus (BHV), Bovine Respiratory Syncytial Virus (BRSV), Parainfluenza Virus (PI-3), *Campylobacter fetus, Leptospira canicola, Leptospira grippotyphosa, Leptospira borgpetersenii, Leptospira prajitno, Leptospira icterohaemmorrhagiae, Leptospira hardjo, Leptospira bovis, Leptospira interrogans* and/or *Leptospira ponoma*.

According to a further aspect, the present invention relates to a combination vaccine and/or the combined use of immunogenic compositions for the treatment and/or prophylaxis of cattle against infections of the respiratory and/or reproductive system caused by *M. bovis*, BVDV, PI-3, BRSV, IBR and/or BHV, wherein said vaccine comprises at least one *M. bovis* antigen, preferably the attenuated, avirulent *M. bovis* as described herein, and at least one further immunologically active component effective for the treatment and/or prophylaxis of infections caused by BVDV, PI-3, BRSV IBR and/or BHV.

BRIEF DESCRIPTION OF THE FIGURES

FIG. 3: Average Group Score for *M. bovis* specific Antibodies from Serum Samples (Days 0, 14, 28, 35 and 42)

FIG. 4: Comparison of Serology for Live Vac I, II, III and No Vaccine Group (SQ+IN only)

DETAILED DESCRIPTION OF THE INVENTION

*M. bovis* Antigen

Figure 1:
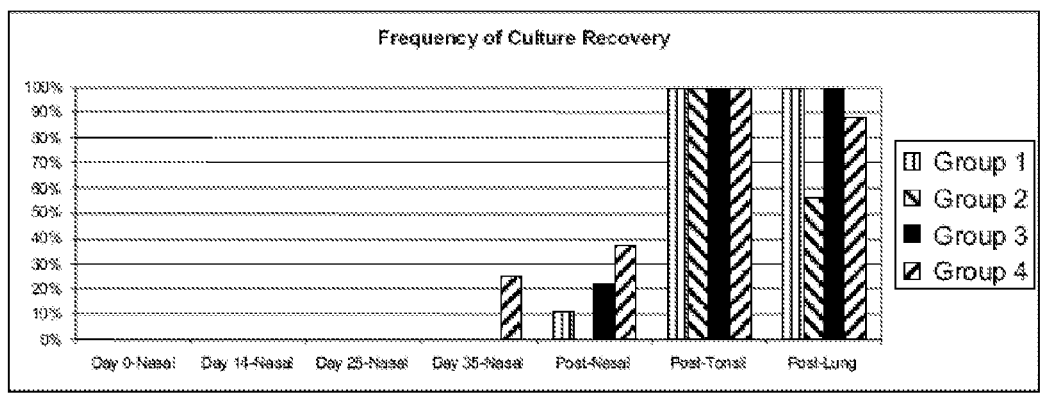
FIG. 1: Frequency of Culture Recovery from Nasal, Tonsil and Lung Samples (Days 0, 14, 28, 35 and Post)

The immunogenic compositions or vaccines of the present invention overcomes the problems present in the prior art by providing avirulent and attenuated strains of *M. bovis*, preferably high passaged, capable of being combined with a pharmaceutically or veterinarily acceptable carrier and at least one further immunologically active component effective for the treatment and/or prophylaxis of infections caused by a relevant cattle pathogen other than *M. bovis*. Any of those immunogenic compositions or vaccines can be used as an immunogenic composition/vaccine with improved efficacy such that signs of *M. bovis* infection and/or the *M. bovis* infection itself and/or incidence or severity, are reduced in comparison with infection by wild-type *M. bovis* strains, preferably as well as in comparison to currently available vaccines. In other words, calves given a vaccine in accordance with the present invention are at a lower risk of developing signs of *M. bovis* infection, and any clinical signs that result would be less severe or prevalent than in animals not receiving any vaccine, but were infected with *M. bovis* or received a vaccine not in accordance with the present invention. The composition of the present invention provided surprising results in that strains of *M. bovis*, preferably high passaged strains of *M. bovis* were attenuated, live, and more highly effective as components of an immunogenic composition.

The invention disclosed herein provides for avirulent and attenuated strains or isolates of *M. bovis*, preferably high passaged attenuated and avirulent strains of *M. bovis* that elicit or provoke an immune response when administered to an animal. Advantageously, the immune response protects the animals receiving the administration of the composition of the present invention such that individual animals are a lower risk of developing signs of *M. bovis* infection, and such signs would be less severe or prevalent than in animals not receiving the composition or in animals receiving a vaccine or composition not made in accordance with the present invention.

For the purposes of the present invention, the terms "isolate" and "strain" are used interchangeably and those differences between individual strains or isolates can be detected using DNA fingerprinting (i.e. different strains or isolates will have differing fingerprints), preferably by using the method as described in WO 2008-030619.

In one embodiment, the immunogenic composition disclosed herein comprises a high passage strain of *M. bovis*. Preferably, said *M. bovis* strain is attenuated and avirulent. The immunogenic composition of the present invention produces an immune response against *M. bovis* infection in cattle. The immunogenic response to *M. bovis* infection generated or induced by administration of the immunogenic composition greatly reduces the severity of or incidence of signs of *M. bovis* infection. In another embodiment, a method of stimulating a rapid and long lasting serological humoral immune response, and consequently disease protection, using the immunogenic composition provided herewith in calves is disclosed. In yet another embodiment, a method of immunizing calves against *M. bovis* infection by administering the immunogenic composition of the present invention in an effective amount is disclosed. The immunogenic or vaccine composition of the present invention, when administered to calves subsequently challenged with a wild-type strain of *M. bovis*, exhibited a decrease in signs of *M. bovis* infection including a decrease in clinical symptoms, lung pathology, lameness, and joint pathology normally associated with *M. bovis* infection. Specifically, a reduction in lung pathology and an appreciable reduction in joint clinical symptoms and associated lameness were observed in the vaccinated group. In another embodiment of the present invention, a method for reducing signs of *M. bovis* infection is disclosed, preferably by administering any of the attenuated, avirulent *M. bovis* bacteria according to the invention and/or disclosed in the present patent applications. The reduction of signs of *M. bovis* infection is achieved by administration of the immunogenic composition of the present invention.

The attenuated and avirulent *M. bovis* high passage strains as provided herewith are preferably passaged more than 10, preferably at least 20, still more preferably at least 30, even more preferably at least 40, still more preferably, at least 50, even more preferably at least 55, still more preferably at least 60, even more preferably at least 70, still more preferably, at least 80, even more preferably at least 90, still more preferably at least 95, even more preferably at least 100, still more preferably at least 102 times, and most preferably at least 106 times, preferably in vitro. Three representative *M. bovis* strains are provided, which include *M. bovis* strain 052823A106, deposited with the ATCC in Manassas, Va. on Oct. 16, 2007 under the terms of the Budapest Treaty and designated as PTA-8694; *M. bovis* strain 05249A102, also deposited with the ATCC in Manassas, Va. on Oct. 16, 2007 under the terms of the Budapest Treaty and designated as PTA-8696; and *M. bovis* strain 0519021B106, also deposited with the ATCC in Manassas, Va. on Oct. 16, 2007 and designated as PTA-8695. Each of these strains prior to passaging are pathogenic, but after passaging each of these strains as described above, and particularly after passaging more than 100 times, the resultant passaged strains were attenuated, avirulent, and produced an immune response in an animal receiving an administration of the immunogenic composition of the strain. In a preferred embodiment of the present invention, the immunogenic compositions comprise one of the three high passage, attenuated strains of *M. bovis* provided herewith.

According to another aspect, the present invention provides immunogenic compositions as described herein, comprising any of the attenuated *M. bovis* bacteria strains deposited with the ATCC under accession numbers PTA-8694; PTA-8695; or PTA-8696, or any attenuated descendant *M. bovis* bacterium strain of any of the foregoing deposited *M. bovis* bacteria strains. More preferably, the present invention provides those immunogenic compositions comprising any of the attenuated *M. bovis* bacteria strains deposited with the ATCC under accession numbers PTA-8694; PTA-8695; or PTA-8696. Moreover, the present invention also relates to the veterinary use of any of those specific an attenuated *M. bovis* strains as described herein, e.g. for the reduction of the severity and/or incidence of clinical symptoms of *M. bovis* infection after laboratory or natural challenge with a pathogenic strain or wild-type strain of *M. bovis*.

According to another aspect, the present invention also relates the use of an attenuated *M. bovis* bacteria having the same characteristics as the *M. bovis* bacteria strains deposited with the ATCC under accession numbers PTA-8694; PTA-8695; or PTA-8696 in any of the immunogenic compositions as provided herewith. The term "having the same characteristics as the *M. bovis* bacteria strains deposited with the ATCC under accession numbers PTA-8694; PTA-8695; or PTA-8696" means that such a bacterium strain is attenuated, is capable of inducing a humoral immune response in a calf within 14 days after administration of one avirulent live culture dose of 2.1E9 CFU via the subcutaneous or intranasal route to a calf. When given at the dose via the route that induces a humoral immune response in a calf within 14 days after administration, the immunogenic composition does not cause clinical signs normally caused by an infection with a pathogenic *M. bovis* wild-type strain. As a reference method, the humoral immune response may be determined by the BIOVET *M. bovis* ELISA-Kit using the protocol provided with the test kit. Preferably, each of the strains above induces a humoral immune response within 14 days after administration of one dose of 2.1 E9 CFU via the subcutaneous or intranasal route to a calf, that has a relative ELISA score in the BIOVET *M. bovis* ELISA-Kit using the protocol provided with the test kit of at least 1.75 when expressed as Optical Density (O.D.) readings.

In another aspect, the invention is a method for the treatment or prophylaxis, including a lessening of the incidence of wild type infection in a herd or reduction in the severity of clinical signs, of *M. bovis* infection associated with wild type *M. bovis* infected animals. Additionally, administration of the vaccine in accordance with the present invention reduces the number of animals in a herd that become infected with *M. bovis*. Such a method generally involves the administration of an effective amount of an *M. bovis* strain, attenuated through the methods disclosed above, to a subject or herd of subjects in need of or that could benefit from such a treatment. Preferably, clinical symptoms are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, and most preferably by at least 95% in comparison to animals that are either not vaccinated or vaccinated with an *M. bovis* immunogenic composition that was available prior to the present invention but subsequently infected by wild-type *M. bovis*.

Combination Partners

As described above, the present invention relates to combination vaccines and/or the combined use of immunogenic compositions for the treatment and/or prophylaxis of cattle against microbiological infections, wherein the infections are caused by *M. bovis* and at least one further relevant cattle pathogen. The combination vaccine as described herein comprises at least one *M. bovis* antigen, preferably the attenuated, avirulent *M. bovis* as provided herewith and one or more further immunologically active components effective for the treatment and/or prophylaxis of infections caused by one or more further relevant pathogen of cattle. The combined use or the method of co-administration of two or more antigens of pathogens affecting cattle comprises administering a first immunogenic composition comprising *M. bovis* antigen, preferably the attenuated, avirulent *M. bovis* as provided herewith and at least one further immunologically active component effective for the treatment and/or prophylaxis of infections caused by a further relevant pathogen of cattle.

Relevant cattle pathogens other than *M. bovis* include those listed in the background section above but are not limited to: i) pathogens of viral origin such as Bovine viral diarrhea virus (BVDV) type 1 (BVDV-1) and type 2 (BVDV-2), Parainfluenza-3 Virus (PI-3), Infectious Bovine Rhinotracheitis virus (IBR) Bovine Respiratory Syncytial Virus (BRSV), Bovine Herpesvirus (BHV), Bovine Rotavirus (BRV), Bovine Enterovirus (BEV), Bovine Coronavirus (BCV), Bovine Rabies (BR), Bovine Parvovirus (BPV), and Adenovirus and Astrovirus; ii) pathogens of bacterial origin, such as *Mannheimia haemolytica* (formerly *Pasteurella haemolytica*), *Pasteurella multocida*, *Haemophilus somnus* (*Histophilus ovis* and *Haemophilus agni*), *Actinomyces* (*Corynebacterium*), *Actinomyces pyogenes*, *Chlamydia psittaci*, *Campylobacter fetus venerealis* and *Campylobacter fetus fetus* (formerly *C. fetus intestinalis*), *Leptospira interrogans*, *Leptospira pomona*, and *Leptospira grippotyphosa*, *Leptospira canicola*, *Leptospira grippotyphosa*, *Leptospira hardjo* (*Leptospira hardjoprajitno* and *Leptospira hardjo-bovis*), *Brucella abortus*, *Brucella suis* and *Brucella melitensis*, *Eschericia coli*, *Listeria monocytogenes*, *Chlamydia psittaci*, *Clostridium chauvoei*, *Clostridium septicum*, *Clostridium haemolyticum*, *Clostridium novyi*, *Clostridium sordellii*, *Clostridium perfringens*, *Clostridium tetani*, *Moraxella bovis*, *Klebsiella* spp, *Klebsiella pneumoniae*, *Salmonella typhimurium; Salmonella newport*, *Mycobacterium avium paratuberculosis*, *Staphylococcus aureus*, *Streptococcus dysgalactiae*, *Mycoplasma dispar*, and *Ureaplasma* spp., and *Streptococcus uberis* iii) pathogens of other origin, such as *Tritrichomonas foetus*, *Trichophyton verrucosum*, *Trichophyton mentagrophytes*, *Trichophyton sarkisovii*, *Neospora caninum* (formerly *Toxoplasma gondii*), *Cryptsporidium parvum*, *Cryptosporidium hominis*, *Babesia bigemina* and *Babesia bovis*, and *Dictyocaulus viviparous* (Lungworm disease).

The combined use or the method of co-administration of two or more antigens of pathogens affecting cattle comprises administering a first immunogenic composition comprising *M. bovis* antigen, preferably the attenuated, avirulent *M. bovis* as provided herewith and at least one further immunologically active component effective for the treatment and/or prophylaxis of infections caused by a further pathogen of cattle, wherein said further pathogen of cattle is selected from the group consisting of: i) pathogens of viral origin such as Bovine viral diarrhea virus (BVDV) type 1 (BVDV-1) and type 2 (BVDV-2), Parainfluenza-3 Virus (PI-3), Infectious Bovine Rhinotracheitis virus (IBR), Bovine Respiratory Syncytial Virus (BRSV), Bovine Herpesvirus (BHV), Bovine Rotavirus (BRV), Bovine Enterovirus (BEV), Bovine Coronavirus (BCV), Bovine Rabies (BR), Bovine Parvovirus (BPV), and Adenovirus and Astrovirus; ii) pathogens of bacterial origin, such as *Mannheimia haemolytica* (formerly *Pasteurella haemolytica*), *Pasteurella multocida, Haemophilus somnus* (*Histophilus ovis* and *Haemophilus agni*), *Actinomyces* (*Corynebacterium*), *Actinomyces pyogenes, Chlamydia psittaci, Campylobacter fetus venerealis* and *Campylobacter fetus fetus* (formerly *C. fetus intestinalis*), *Leptospira interrogans, Leptospira pomona*, and *Leptospira grippotyphosa, Leptospira canicola, Leptospira grippotyphosa, Leptospira hardjo* (*Leptospira hardjoprajitno* and *Leptospira hardjobovis*), *Brucella abortus, Brucella suis* and *Brucella melitensis, Escherichia coli, Listeria monocytogenes, Chlamydia psittaci, Clostridium chauvoei, Clostridium septicum, Clostridium haemolyticum, Clostridium novyi, Clostridium sordellii, Clostridium perfringens, Clostridium tetani, Moraxella bovis, Klebsiella* spp, *Klebsiella pneumoniae, Salmonella typhimurium; Salmonella newport, Mycobacterium avium paratuberculosis, Staphylococcus aureus, Streptococcus dysgalactiae, Mycoplasma dispar*, and *Ureaplasma* spp., and *Streptococcus uberis* and iii) pathogens of other origin, such as *Tritrichomonas foetus, Trichophyton verrucosum, Trichophyton mentagrophytes, Trichophyton sarkisovii, Neospora caninum* (formerly *Toxoplasma gondii*), *Cryptsporidium parvum, Cryptsporidium hominis, Babesia bigemina* and *Babesia bovis*, and *Dictyocaulus viviparous* (Lungworm disease) or any other pathogen listed in the background section or known to be pathogenic in cattle.

The present invention relates to combination vaccines and/or the combined use of immunogenic compositions for the treatment and/or prophylaxis of cattle against microbiological infections, wherein the infections are caused by *M. bovis* and at least one further cattle relevant pathogen, wherein said vaccine or combined use comprises or makes use of an *M. bovis* antigen, preferably the avirulent, attenuated *M. bovis*, as described herein, and a further immunologically active component effective for the treatment and/or prophylaxis of infections caused by Bovine viral diarrhea virus (BVDV) type 1 (BVDV-1) and type 2 (BVDV-2), Parainfluenza-3 Virus (PI-3), Infectious Bovine Rhinotracheitis virus (IBR) Bovine Respiratory Syncytial Virus (BRSV), Bovine Herpesvirus (BHV), Bovine Rotavirus (BRV), Bovine Enterovirus (BEV), Bovine Coronavirus (BCV), Bovine Rabies (BR), Bovine Parvovirus (BPV), Adenovirus Astrovirus, *Mannheimia haemolytica* (formerly *Pasteurella haemolytica*), *Pasteurella multocida, Haemophilus somnus* (*Histophilus ovis* and *Haemophilus agni*), *Actinomyces* (*Corynebacterium*), *Actinomyces pyogenes, Chlamydia psittaci, Campylobacter fetus venerealis* and *Campylobacter fetus fetus* (formerly *C. fetus intestinalis*), *Leptospira interrogans, Leptospira pomona*, and *Leptospira grippotyphosa, Leptospira canicola, Leptospira grippotyphosa, Leptospira hardjo* (*Leptospira hardjoprajitno* and *Leptospira hardjo-bovis*), *Brucella abortus, Brucella suis* and *Brucella melitensis, Escherichia coli, Listeria monocytogenes, Chlamydia psittaci, Clostridium chauvoei, Clostridium septicum, Clostridium haemolyticum, Clostridium novyi, Clostridium sordellii, Clostridium perfringens, Clostridium tetani, Moraxella bovis, Klebsiella* spp, *Klebsiella pneumoniae, Salmonella typhimurium; Salmonella newport, Mycobacterium avium paratuberculosis, Cryptsporidium parvum, Cryptsporidium hominis, Staphylococcus aureus, Streptococcus dysgalactiae, Streptococcus uberis, Mycoplasma* spp, *Mycoplasma dispar*, and *Ureaplasma* spp., *Tritrichomonas foetus, Trichophyton verrucosum, Trichophyton mentagrophytes, Trichophyton sarkisovii, Neospora caninum* (formerly *Toxoplasma gondii*), *Babesia bigemina* and *Babesia bovis*, and *Dictyocaulus viviparous* (Lungworm disease) and/or any other pathogen known to be pathogenic in cattle, including the pathogens discussed in the background.

The combined use or the method of co-administration of two or more antigens of pathogens affecting cattle comprises administering a first immunogenic composition comprising *M. bovis* antigen, preferably the attenuated, avirulent *M. bovis*, as provided herewith, and at least one further immunogenic composition comprising one or more further immunologically active components effective for the treatment and/or prophylaxis of infections caused by a further pathogen of cattle, wherein said further pathogen of cattle is selected from the group consisting of: Bovine viral diarrhea virus (BVDV) type 1 (BVDV-1) and type 2 (BVDV-2), Parainfluenza-3 Virus (PI-3), Infectious Bovine Rhinotracheitis virus (IBR), Bovine Respiratory Syncytial Virus (BRSV), Bovine Herpesvirus (BHV), Bovine Rotavirus (BRV), Bovine Enterovirus (BEV), Bovine Coronavirus (BCV), Bovine Rabies (BR), Bovine Parvovirus (PPV), Adenovirus Astrovirus, *Mannheimia haemolytica* (formerly *Pasteurella haemolytica*), *Pasteurella multocida, Haemophilus somnus* (*Histophilus ovis* and *Haemophilus agni*), *Actinomyces* (*Corynebacterium*), *Actinomyces pyogenes, Chlamydia psittaci, Campylobacter fetus venerealis* and *Campylobacter fetus fetus* (formerly *C. fetus intestinalis*), *Leptospira interrogans, Leptospira pomona*, and *Leptospira grippotyphosa, Leptospira canicola, Leptospira grippotyphosa, Leptospira hardjo* (*Leptospira hardjoprajitno* and *Leptospira hardjo-bovis*), *Brucella abortus, Brucella suis* and *Brucella melitensis, Escherichia coli, Listeria monocytogenes, Chlamydia psittaci, Clostridium chauvoei, Clostridium septicum, Clostridium haemolyticum, Clostridium novyi, Clostridium sordellii, Clostridium perfringens, Clostridium tetani, Moraxella bovis, Klebsiella* spp, *Klebsiella pneumoniae, Salmonella typhimurium; Salmonella newport, Mycobacterium avium paratuberculosis, Cryptsporidium parvum, Cryptsporidium hominis, Staphylococcus aureus, Streptococcus dysgalactiae, Streptococcus uberis, Mycoplasma* spp, *Mycoplasma dispar, Mycoplasma bovis*, and *Ureaplasma* spp., *Tritrichomonas foetus, Trichophyton verrucosum, Trichophyton mentagrophytes, Trichophyton sarkisovii, Neospora caninum* (formerly *Toxoplasma gondii*), *Babesia bigemina* and *Babesia bovis*, and *Dictyocaulus viviparous* (Lungworm disease) and/or any other pathogen listed in the background section or known to be pathogenic in cattle. Preferably, the further immunogenic composition comprises an antigen of one or more of any of the cattle relevant pathogens as listed above.

According to a further embodiment, the present invention relates to a combination vaccine or the combined use of immunogenic compositions for the treatment and/or prophylaxis of cattle against infections of the respiratory and/or reproductive systems in cattle, wherein the combination vaccine or combined use comprises a *M. bovis* antigen, preferably the attenuated and avirulent *M. bovis* as described herein, and at least one further immunologically active component effective for the treatment and/or prophylaxis of infections caused by IBR [combo 001]. According to a preferred embodiment, the combination vaccine comprises *M. bovis*, preferably the attenuated and avirulent *M. bovis*, as described herein, and at least one antigen of IBR [combo 002]. According to a preferred embodiment, the IBR antigen is a live modified virus [combo 003]. According to a further embodiment, the combination vaccine of attenuated *M. bovis* and IBR contains an antibiotic, e.g. neomycin, for preservation [combo 004].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and at least one further immunologically active component effective for the treatment and/or prophylaxis of infections caused by PI-3 [combo 005]. According to a preferred embodiment, the combination vaccine comprises *M. bovis*, preferably the attenuated and avirulent *M. bovis* as described herein, and at least one antigen of PI-3 [combo 006]

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and at least one further immunologically active component effective for the treatment and/or prophylaxis of infections caused by BVDV (type 1 and/or type 2), preferably attenuated BVDV (type 1 and/or type 2) [combo 007]. According to a more preferred embodiment, the combination vaccine comprises *M. bovis*, preferably the attenuated and avirulent *M. bovis* as described herein and at least one antigen of BVDV (type 1 and/or type 2), preferably attenuated BVDV (type 1 and/or type 2) [combo 008].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and at least one further immunologically active component effective for the treatment and/or prophylaxis of infections caused by BHV [combo 009]. According to a preferred embodiment, the combination vaccine comprises *M. bovis*, preferably the attenuated and avirulent *M. bovis* as described herein, and at least one antigen of BHV [combo 010].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR and PI-3 [combo 011]. According to a preferred embodiment, the combination vaccine comprises *M. bovis*, preferably the attenuated and avirulent *M. bovis* as described herein, and at least one antigen each of IBR and PI-3 [combo 012].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR and BVDV (type 1 and/or type 2), preferably attenuated BVDV (type 1 and/or type 2) [combo 013]. According to a preferred embodiment, the combination vaccine comprises *M. bovis*, preferably the attenuated and avirulent *M. bovis* as described herein, and at least one antigen each of IBR and BVDV (type 1 and/or type 2), preferably attenuated BVDV (type 1 and/or type 2) [combo 014].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR and BHV [combo 015]. According to a preferred embodiment, the combination vaccine comprises *M. bovis*, preferably the attenuated and avirulent *M. bovis* as described herein, and at least one antigen each of IBR and BHV [combo 016].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by PI-3 and BVDV (type 1 and/or type 2), preferably attenuated BVDV (type 1 and/or type 2) [combo 017]. According to a preferred embodiment, the combination vaccine comprises *M. bovis*, preferably the attenuated and avirulent *M. bovis* as described herein, and at least one antigen each of PI-3 and BVDV (type 1 and/or type 2), preferably attenuated BVDV (type 1 and/or type 2) [combo 018].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by PI-3 and BHV [combo 019]. According to a preferred embodiment, the combination vaccine comprises *M. bovis*, preferably the attenuated and avirulent *M. bovis* as described herein, and at least one antigen each of PI-3 and BHV [combo 020].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3 and BVDV (type 1 and/or type 2), preferably attenuated BVDV (type 1 and/or type 2) [combo 021]. According to a preferred embodiment, the combination vaccine comprises *M. bovis*, preferably the attenuated and avirulent *M. bovis* as described herein and at least one antigen each of IBR, PI-3 and BVDV (type 1 and/or type 2), preferably attenuated BVDV (type 1 and/or type 2) [combo 022]. Preferably, all viral antigens are modified live viruses [combo 023].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by BRSV and BVDV (type 1 and/or type 2), preferably attenuated BVDV (type 1 and/or type 2) [combo 024]. According to a preferred embodiment, the combination vaccine comprises *M. bovis*, preferably the attenuated and avirulent *M. bovis* as described herein, and at least one antigen of each BRSV and BVDV (type 1 and/or type 2), preferably attenuated BVDV (type 1 and/or type 2 [combo 025].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, BVDV (type 1 and/or type 2), preferably attenuated BVDV (type 1 and/or type 2 and BHV [combo 026]. According to a preferred embodiment, the combination vaccine comprises *M. bovis*, preferably the attenuated and avirulent *M. bovis* as described herein, and at least one antigen each of IBR BHV, and BVDV (type 1 and/or type 2), preferably attenuated BVDV (type 1 and/or type 2 [combo 027].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by PI-3, BVDV (type 1 and/or type 2), preferably attenuated BVDV (type 1 and/or type 2 and BHV [combo 028]. According to a preferred embodiment, the combination vaccine comprises *M. bovis*, preferably the attenuated and avirulent *M. bovis* as described herein, and at least one antigen each of PI-3 and BVDV (type 1 and/or type 2), preferably attenuated BVDV (type 1 and/or type 2 and BHV [combo 029].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3 and BHV [combo 030]. According to a preferred embodiment, the combination vaccine comprises *M. bovis*, preferably the attenuated and avirulent *M. bovis* as described herein, and at least one antigen each of IBR, BHV and PI-3 [combo 031].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active component effective for the treatment and/or prophylaxis of infections caused by IBR, PI-3, BVDV (type 1 and/or type 2), preferably attenuated BVDV (type 1 and/or type 2 and BHV [combo 032]. According to a more preferred embodiment, the combination vaccine comprises *M. bovis*, preferably the attenuated and avirulent *M. bovis* as described herein, and at least one antigen each of IBR BHV PI-3, and BVDV (type 1 and/or type 2), preferably attenuated BVDV (type 1 and/or type 2) [combo 033].

According to a further embodiment, the present invention relates to a combination vaccine for the treatment and/or prophylaxis of cattle against bacterial infections of the respiratory and reproductive systems in cattle, wherein the combination vaccine comprises *M. bovis*, preferably the attenuated and avirulent *M. bovis* as described herein, and at least one further immunologically active component effective for the treatment and/or prophylaxis of infections caused by *H. somnus* [combo 034]. According to a more preferred embodiment, the combination vaccine comprises *M. bovis*, preferably the attenuated and avirulent *M. bovis* as described herein, and at least one antigen of *H. somnus* [combo 035].

According to a further embodiment, the present invention relates to a combination vaccine for the treatment and/or prophylaxis of cattle against viral and bacterial infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR and *H. somnus* [combo 036]. According to a more preferred embodiment, the combination vaccine comprises *M. bovis*, preferably the attenuated and avirulent *M. bovis* as described herein, and at least one antigen each of *H. somnus* and IBR [combo 037].

According to a further embodiment, the present invention relates to a combination vaccine for the treatment and/or prophylaxis of cattle against viral and bacterial infections of the respiratory and reproductive systems in cattle, wherein the combination vaccine comprises *M. bovis*, preferably the attenuated and avirulent *M. bovis* as described herein, and at least one further immunologically active components effective for the treatment and/or prophylaxis of infections caused by IBR, PI-3, and *H. somnus* [combo 038]. According to a more preferred embodiment, the combination vaccine comprises *M. bovis*, preferably the attenuated and avirulent *M. bovis* as described herein, and at least one antigen each of IBR, PI-3, and *H. somnus* [combo 039].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2) and *H. somnus* [combo 040]. According to a more preferred embodiment, the combination vaccine comprises *M. bovis*, preferably the attenuated and avirulent *M. bovis* as described herein, and at least one antigen each of IBR, PI-3 and BVDV (type 1 and/or type 2), preferably attenuated BVDV (type 1 and/or type 2) and one antigen of *H. somnus* [combo 041]. According to a further embodiment of said combination vaccine, the IBR, PI-3 antigens are killed viruses [combo 042]. According to a further embodiment, any of said combination vaccines, preferably the combination vaccine that comprises killed IBR and killed PI-3 antigens, contains neomycin and thimerosal as preservatives [combo 043].

According to a further embodiment, the present invention relates to a combination vaccine for the treatment and/or prophylaxis of cattle against viral infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), BHV and *H. somnus* [combo 044]. According to a more preferred embodiment, the combination vaccine comprises *M. bovis*, preferably the attenuated and avirulent *M. bovis* as described herein, and at least one antigen each of IBR, BHV, PI-3, and BVDV (type 1 and/or type 2), preferably attenuated BVDV (type 1 and/or type 2) and one antigen of *H. somnus* [combo 045].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and at least one further immunologically active component effective for the treatment and/or prophylaxis of infections caused by one or more pathogenic species of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona*. [combo 046]. According to a more preferred embodiment, the combination vaccine comprises *M. bovis*, preferably the attenuated and avirulent *M. bovis* as described herein and one or more antigens of at least one or more pathogenic species of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona* [combo 047].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR and one or more pathogenic species of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona*. [combo 048]. According to a more preferred embodiment, the combination vaccine comprises *M. bovis*, preferably the attenuated and avirulent *M. bovis* as described herein and at least one antigen each of IBR and one or more pathogenic specie(s) of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona* [combo 049].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR and *Leptospira pomona* [combo 050]. According to a more preferred embodiment, the combination vaccine comprises *M. bovis*, preferably the attenuated and avirulent *M. bovis* as described herein, and at least one antigen of IBR, preferably a live modified virus, and at least one *Leptospira pomona* bacterin [combo 51].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, and one or more pathogenic species of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona* [combo 052]. According to a more preferred embodiment, the combination vaccine comprises *M. bovis*, preferably the attenuated and avirulent *M. bovis* as described herein, and at least one antigen each of IBR, and PI-3, and one or more antigens each of one or more pathogenic specie(s) of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona* [combo 053].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, *Leptospira canicola, Leptospira grippotyphosa, Leptospira hardjo* (*Leptospira hardjoprajitno* and/or *Leptospira hardjo-bovis*), *Leptospira icterohaemmorrhagiae*, and *Leptospira pomona* [combo 054]. According to a more preferred embodiment, the combination vaccine comprises *M. bovis*, preferably the attenuated and avirulent *M. bovis* as described herein, and at least one antigen each of IBR, PI-3, *Leptospira canicola, Leptospira grippotyphosa, Leptospira hardjo, Leptospira icterohaemorrhagiae* and *Leptospira pomona* [combo 055].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2) and one or more pathogenic species of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona* [combo 056]. According to a more preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2) and one or more antigens each of one or more pathogenic species of *Leptospira*, preferably selected from the group consisting of *Leptospira canicola, Leptospira grippotyphosa, Leptospira borgpetersenii, Leptospira pra-* jitno, *Leptospira icterohaemmorrhagiae, Leptospira bovis, Leptospira interrogans* and *Leptospira pomona* [combo 057].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), *Leptospira canicola, Leptospira grippotyphosa, Leptospira hardjo* (*Leptospira hardjoprajitno* and/or *Leptospira hardjo-bovis*), *Leptospira icterohaemorrhagiae*, and *Leptospira pomona* [combo 058]. According to a more preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), and one or more antigens each of *Leptospira canicola, Leptospira grippotyphosa, Leptospira hardjo* (*Leptospira hardjoprajitno* and/or *Leptospira hardjo-bovis*), *Leptospira icterohaemorrhagiae*, and *Leptospira pomona* [combo 059]. According to a preferred embodiment, the viral antigens are killed viruses and the bacterial antigens are bacterins [combo 060]. Preferably, said combination vaccines as described in this paragraph further contain neomycin and thimerosal as preservatives [combo 061].

According to a further embodiment, the combination vaccine comprises *M. bovis*, preferably the attenuated and avirulent *M. bovis* as described herein, live modified viruses of IBR, PI-3, BVDV (type 1 and/or type 2), preferably attenuated BVDV (type 1 and/or type 2), and bacterin of *Leptospira canicola, Leptospira grippotyphosa, Leptospira hardjo* (*Leptospira hardjoprajitno* and/or *Leptospira hardjo-bovis*), *Leptospira icterohaemorrhagiae* and *Leptospira pomona* [combo 062]. According to a further preferred embodiment, the combination vaccine described in this paragraph comprises neomycin as a preservative [combo 063].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), BHV and one or more pathogenic species of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona*. [combo 064]. According to a more preferred embodiment, the combination vaccine comprises *M. bovis*, preferably the attenuated and avirulent *M. bovis* as described herein, and at least one antigen each of IBR BHV, PI-3, and BVDV (type 1 and/or type 2), preferably attenuated BVDV (type 1 and/or type 2), and one or more antigens each of one or more pathogenic species of *Leptospira*, preferably selected from the group consisting of *Leptospira canicola, Leptospira grippotyphosa, Leptospira borgpetersenii, Leptospira hardjo* (*Leptospira hardjoprajitno* and *Leptospira hardjo-bovis*), *Leptospira prajitno, Leptospira icterohaemmorrhagiae, Leptospira bovis, Leptospira interrogans* and *Leptospira pomona* [combo 065].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by one or more pathogenic species of *Leptospira*, as mentioned above, and *H. somnus* [combo 066]. According to a more preferred embodiment, the combination vaccine comprises *M. bovis*, preferably the attenuated and avirulent *M. bovis* as described herein, and at least one antigen of one or more pathogenic species of *Leptospira*, as mentioned above, and at least one antigen of *H. somnus* [combo 067].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR and one or more pathogenic specie(s) of *Leptospira*, as mentioned above, and *H. somnus* [combo 068]. According to a more preferred embodiment, the combination vaccine comprises *M. bovis*, preferably the attenuated and avirulent *M. bovis* as described herein, and at least one antigen of IBR and at least one antigen each of one or more pathogenic species of *Leptospira*, as mentioned above, and at least one antigen of *H. somnus* [combo 069].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3 and one or more pathogenic specie(s) of *Leptospira*, as mentioned above, and *H. somnus* [combo 070]. According to a more preferred embodiment, the combination vaccine comprises *M. bovis*, preferably the attenuated and avirulent *M. bovis* as described herein, and at least one antigen each of IBR, PI-3, and at least one antigen each of one or more pathogenic species of *Leptospira*, as mentioned above, and at least one antigen of *H. somnus* [combo 071].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, *Leptospira canicola, Leptospira grippotyphosa, Leptospira hardjo* (*Leptospira hardjoprajitno* and/or *Leptospira hardjo-bovis*), *Leptospira icterohaemorrhagiae, Leptospira pomona* and *H. somnus* [combo 072]. According to a more preferred embodiment, the combination vaccine comprises *M. bovis*, preferably the attenuated and avirulent *M. bovis* as described herein, and at least one antigen each of IBR, PI-3, *Leptospira canicola, Leptospira grippotyphosa, Leptospira hardjo* (*Leptospira hardjoprajitno* and/or *Leptospira hardjo-bovis*), *Leptospira icterohaemorrhagiae, Leptospira pomona*, and *H. somnus* [combo 073].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), and one or more pathogenic specie(s) of *Leptospira*, as mentioned above, and *H. somnus* [combo 074]. According to a preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), and one or more antigens each of one or more pathogenic species of *Leptospira*, as mentioned above, and at least one antigen of *H. somnus* [combo 075].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), *Leptospira canicola, Leptospira grippotyphosa, Leptospira hardjo* (*Leptospira hardjoprajitno* and/or *Leptospira hardjo-bovis*), *Leptospira icterohaemorrhagiae, Leptospira pomona* and *H. somnus* [combo 076]. According to a more preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), *Leptospira canicola, Leptospira grippotyphosa, Leptospira hardjo, Leptospira icterohaemorrhagiae, Leptospira pomona* and *H. somnus* [combo 077].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), BHV and one or more pathogenic specie(s) of *Leptospira*, as mentioned above, and *H. somnus* [combo 078]. According to a more preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), BHV and one or more antigens each of one or more pathogenic species of *Leptospira*, as mentioned above, and at least one antigen of *H. somnus* [combo 079].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by one or more pathogenic specie(s) of *Leptospira*, as mentioned above, and *Campylobacter fetus* [combo 080]. According to a more preferred embodiment, the combination vaccine comprises *M. bovis*, preferably the attenuated and avirulent *M. bovis* as described herein, and at least one or more antigens each of one or more pathogenic species of *Leptospira*, as mentioned above, and at least one antigen of *Campylobacter fetus* [combo 081].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by *Leptospira canicola, Leptospira grippotyphosa, Leptospira hardjo* (*Leptospira hardjoprajitno* and/or *Leptospira hardjo-bovis*), *Leptospira icterohaemorrhagiae, Leptospira pomona* and *Campylobacter fetus* [combo 082]. According to a preferred embodiment, the combination vaccine comprises *M. bovis*, preferably the attenuated and avirulent *M. bovis* as described herein, and at least antigen each of *Leptospira canicola, Leptospira grippotyphosa, Leptospira hardjo* (*Leptospira hardjoprajitno* and *Leptospira hardjo-bovis*), *Leptospira icterohaemorrhagiae, Leptospira pomona* and *Campylobacter fetus* [combo 083]. According to a more preferred embodiment, the bacterial antigens are chemically inactivated, aluminum hydroxide adsorbed, whole cultures of said bacteria [combo 084]. According to a further preferred embodiment, said combination vaccine comprises gentamicin and Amphotericin B as preservatives [combo 085].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR and one or more pathogenic specie(s) of *Leptospira*, as mentioned above, and *Campylobacter fetus* [combo 086]. According to a more preferred embodiment, the combination vaccine comprises *M. bovis*, preferably the attenuated and avirulent *M. bovis* as described herein, and at least one antigen of IBR and one or more antigens each of one or more pathogenic species of *Leptospira*, as mentioned above, and at least one antigen of *Campylobacter fetus* [combo 087].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3 and one or more pathogenic specie(s) of *Leptospira*, as mentioned above, and *Campylobacter fetus* [combo 088]. According to a more preferred embodiment, the combination vaccine comprises *M. bovis*, preferably the attenuated and avirulent *M. bovis* as described herein, and at least one antigen each of IBR, PI-3, and one or more antigens each of one or more pathogenic species of *Leptospira*, as mentioned above, and at least one antigen of *Campylobacter fetus* [combo 089].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), and one or more pathogenic specie(s) of *Leptospira*, as mentioned above, and *Campylobacter fetus* [combo 090]. According to a more preferred embodiment, the combination vaccine comprises *M.*

*bovis*, preferably the attenuated and avirulent *M. bovis* as described herein, and at least one antigen each of IBR, PI-3, BVDV (type 1 and/or type 2), preferably attenuated BVDV (type 1 and/or type 2), and one or more antigens each of one or more pathogenic species of *Leptospira*, as mentioned above, and at least one antigen of *Campylobacter fetus* [combo 091].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), BHV, one or more pathogenic specie(s) of *Leptospira*, as mentioned above, and *Campylobacter fetus* [combo 092]. According to a more preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), BHV and one or more antigens each of one or more pathogenic species of *Leptospira*, as mentioned above, and at least one antigen of *Campylobacter fetus* [combo 093].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by one or more pathogenic specie(s) of *Leptospira*, as mentioned above, *H. somnus* and *Campylobacter fetus* [combo 094]. According to a more preferred embodiment, the combination vaccine comprises *M. bovis*, preferably the attenuated and avirulent *M. bovis* as described herein, and one or more antigens each of one or more pathogenic species of *Leptospira*, as mentioned above, and at least one antigen each of *H. somnus* and *Campylobacter fetus* [combo 095].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, one or more pathogenic specie(s) of *Leptospira*, as mentioned above, *H. somnus* and *Campylobacter fetus* [combo 096]. According to a more preferred embodiment, the combination vaccine comprises *M. bovis*, preferably the attenuated and avirulent *M. bovis* as described herein, and at least one antigen each of IBR, *H. somnus* and *Campylobacter fetus*, and one or more antigens each of one or more pathogenic species of *Leptospira*, as mentioned above, [combo 097].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, and one or more pathogenic specie(s) of *Leptospira*, as mentioned above, *H. somnus* and *Campylobacter fetus* [combo 098]. According to a preferred embodiment, the combination vaccine comprises *M. bovis*, preferably the attenuated and avirulent *M. bovis* as described herein, and at least one antigen each of IBR, PI-3, *H. somnus* and *Campylobacter fetus* and one or more antigens each of one or more pathogenic species of *Leptospira*, as mentioned above, [combo 099].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, *Leptospira canicola*, *Leptospira grippotyphosa*, *Leptospira hardjo*, *Leptospira icterohaemorrhagiae*, *Leptospira pomona*, *H. somnus* and *Campylobacter fetus* [combo 100]. According to a further embodiment, the combination vaccine comprises *M. bovis*, preferably the attenuated and avirulent *M. bovis* as described herein, and at least one antigen each of IBR, PI-3, *Leptospira canicola*, *Leptospira grippotyphosa*, *Leptospira hardjo* (*Leptospira hardjoprajitno* and/or *Leptospira hardjo-bovis*), *Leptospira icterohaemorrhagiae*, *Leptospira pomona*, *H. somnus* and *Campylobacter fetus* [combo 101].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), and one or more pathogenic specie(s) of *Leptospira*, as mentioned above, *H. somnus* and *Campylobacter fetus* [combo 102]. According to a more preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), *H. somnus* and *Campylobacter fetus* and one or more antigens each of one or more pathogenic species of *Leptospira*, as mentioned above [combo 100].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), *Leptospira canicola*, *Leptospira grippotyphosa*, *Leptospira hardjo* (*Leptospira hardjoprajitno* and/or *Leptospira hardjo-bovis*), *Leptospira icterohaemorrhagiae*, *Leptospira Pomona*, *H. somnus* and *Campylobacter fetus* [combo 103]. According to a further embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), *Leptospira canicola*, *Leptospira grippotyphosa*, *Leptospira hardjo* (*Leptospira hardjoprajitno* and/or *Leptospira hardjo-bovis*), *Leptospira icterohaemorrhagiae*, *Leptospira pomona*, *H. somnus* and *Campylobacter fetus* [combo 104].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), BHV and one or more pathogenic specie(s) of *Leptospira*, as mentioned above, *H. somnus* and *Campylobacter fetus* [combo 105]. According to a more preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), BHV, *H. somnus* and *Campylobacter fetus*, and one or more antigens each of one or more pathogenic species of *Leptospira*, as mentioned above, [combo 106].

According to a further embodiment, the present invention relates to a combination vaccine for the treatment and/or prophylaxis of cattle against infections of the respiratory and reproductive systems in cattle, wherein the combination vaccine comprises *M. bovis*, preferably the attenuated and avirulent *M. bovis* as described herein, and further immunologically active components effective for the treatment and/or prophylaxis of infections caused by BHV, BVDV (type 1 and/or type 2), preferably attenuated BVDV (type 1 and/or type 2), PI-3, IBR, *Leptospira canicola, Leptospira grippotyphosa, Leptospira borgpetersenii Leptospira hardjo (Leptospira hardjoprajitno* and/or *Leptospira hardjo-bovis), Leptospira prajitno, Leptospira icterohaemmorrhagiae, Leptospira bovis, Leptospira interrogans* and *Campylobacter fetus* [combo 107]. According to a more preferred embodiment, the combination vaccine comprises attenuated *M. bovis*, as described herein, and at least one antigen each of BHV, BVDV (type 1 and/or type 2), preferably attenuated BVDV (type 1 and/or type 2), IBR, PI-3, *Leptospira canicola, Leptospira grippotyphosa, Leptospira borgpetersenii Leptospira hardjo (Leptospira hardjoprajitno* and/or *Leptospira hardjo-bovis), Leptospira prajitno, Leptospira icterohaemmorrhagiae, Leptospira borgpetersenii, Leptospira bovis, Leptospira interrogans* and *Campylobacter fetus* [combo 108].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by *Pasteurella haemolytica* and *Pasteurella multocida* [combo 109]. According to a preferred embodiment, the combination vaccine comprises *M. bovis*, preferably the attenuated and avirulent *M. bovis* as described herein, and at least one antigen each of *Pasteurella haemolytica* bacterin and *Pasteurella multocida* bacterin. [combo 110] According to a further preferred embodiment, said combination vaccine comprises neomycin and thimerosal as preservatives [combo 111].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, *Pasteurella haemolytica* and *Pasteurella multocida* [combo 112]. According to a preferred embodiment, the combination vaccine comprises *M. bovis*, preferably the attenuated and avirulent *M. bovis* as described herein, and at least one antigen of each of IBR, preferably as live modified viruses, *Pasteurella haemolytica* bacterin and *Pasteurella multocida* bacterin [combo 113]. According to a further preferred embodiment, said combination vaccine comprises neomycin and thimerosal as preservatives [combo 114].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, *Pasteurella haemolytica* and *Pasteurella multocida* [combo 115]. According to a preferred embodiment, the combination vaccine comprises *M. bovis*, preferably the attenuated and avirulent *M. bovis* as described herein, and at least one antigen each of IBR, PI-3, preferably as live modified viruses, *Pasteurella haemolytica* bacterin and *Pasteurella multocida* bacterin [combo 116]. According to a further preferred embodiment, said combination vaccine comprises neomycin and thimerosal as preservatives [combo 117].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), *Pasteurella haemolytica* and *Pasteurella multocida* [combo 118]. According to a preferred embodiment, the combination vaccine comprises *M. bovis*, preferably the attenuated and avirulent *M. bovis* as described herein, and at least one antigen each of IBR, PI-3, preferably as live modified viruses, BVDV (type 1 and/or type 2), preferably attenuated BVDV (type 1 and/or type 2), *Pasteurella haemolytica* bacterin and *Pasteurella multocida* bacterin [combo 119]. According to a further preferred embodiment, said combination vaccine comprises neomycin and thimerosal as preservatives [combo 120].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active component effective for the treatment and/or prophylaxis of infections caused by IBR, PI-3, BVDV (type 1 and/or type 2), preferably attenuated BVDV (type 1 and/or type 2), BHV, *Pasteurella haemolytica* and *Pasteurella multocida* [combo 121]. According to a preferred embodiment, the combination vaccine comprises *M. bovis*, preferably the attenuated and avirulent *M. bovis*, as described herein, and at least one antigen each of IBR, PI-3, BVDV (type 1 and/or type 2), preferably attenuated BVDV (type 1 and/or type 2), BHV, preferably as live modified viruses, *Pasteurella haemolytica* bacterin and *Pasteurella multocida* bacterin [combo 122]. According to a further preferred embodiment, said combination vaccine comprises neomycin and thimerosal as preservatives [combo 123].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and at least one further immunologically active component effective for the treatment and/or prophylaxis of infections caused by BRSV [combo 124]. According to a preferred embodiment, the combination vaccine comprises *M. bovis*, preferably the attenuated and avirulent *M. bovis* as described herein, and at least antigen of BRSV [combo 125].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, and BRSV [combo 126]. According to a preferred embodiment, the combination vaccine comprises *M. bovis*, preferably the attenuated and avirulent *M. bovis* as described herein, and at least antigen of each IBR, preferably as live modified viruses, and BRSV [combo 127].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active component effective for the treatment and/or prophylaxis of infections caused by IBR, PI-3, and BRSV [combo 128]. According to a preferred embodiment, the combination vaccine comprises *M. bovis*, preferably the attenuated and avirulent *M. bovis* as described herein, and at least one antigen each of IBR, PI-3, preferably as live modified viruses, and BRSV [combo 129].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BRSV, and BVDV (type 1 and/or type 2), preferably attenuated BVDV (type 1 and/or type 2) [combo 130]. According to a preferred embodiment, the combination vaccine comprises *M. bovis*, preferably the attenuated and avirulent *M. bovis* as described herein, and at least one antigen each of IBR, PI-3, BRSV, preferably as live modified viruses, and BVDV (type 1 and/or type 2), preferably attenuated BVDV (type 1 and/or type 2) [combo 131].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BRSV, BHV, and BVDV (type 1 and/or type 2), preferably attenuated BVDV (type 1 and/or type 2) [combo 132]. According to a preferred embodiment, the combination vaccine comprises *M. bovis*, preferably the attenuated and avirulent *M. bovis* as described herein, and at least one antigen each of IBR, PI-3, BRSV, BHV, preferably as live modified viruses, and BVDV (type 1 and/or type 2), preferably attenuated BVDV (type 1 and/or type 2) [combo 133].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by *Pasteurella haemolytica, Pasteurella multocida* and BRSV [combo 134]. According to a preferred embodiment, the combination vaccine comprises *M. bovis*, preferably the attenuated and avirulent *M. bovis* as described herein, and at least one antigen each of *Pasteurella haemolytica, Pasteurella multocida* and BRSV [combo 135].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, *Pasteurella haemolytica, Pasteurella multocida* and BRSV [combo 136]. According to a preferred embodiment, the combination vaccine comprises *M. bovis*, preferably the attenuated and avirulent *M. bovis* as described herein, and at least one antigen each of IBR, preferably as live modified viruses, *Pasteurella haemolytica, Pasteurella multocida* and BRSV [combo 137].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, *Pasteurella haemolytica, Pasteurella multocida* and BRSV [combo 138]. According to a preferred embodiment, the combination vaccine comprises *M. bovis*, preferably the attenuated and avirulent *M. bovis* as described herein, and at least one antigen each of IBR, PI-3, preferably as live modified viruses, *Pasteurella haemolytica, Pasteurella multocida* and BRSV [combo 139].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), *Pasteurella haemolytica, Pasteurella multocida* and BRSV [combo 140]. According to a preferred embodiment, the combination vaccine comprises *M. bovis*, preferably the attenuated and avirulent *M. bovis* as described herein, and at least one antigen each of IBR, PI-3, BVDV (type 1 and/or type 2), preferably as live modified viruses, *Pasteurella haemolytica, Pasteurella multocida* and BRSV [combo 141].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), BHV, *Pasteurella haemolytica, Pasteurella multocida* and BRSV [combo 140]. According to a preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), BHV, preferably as live modified viruses, *Pasteurella haemolytica, Pasteurella multocida* and BRSV [combo 141].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by *Pasteurella haemolytica, Pasteurella multocida* and *H. somnus* [combo 142]. According to a preferred embodiment, the combination vaccine comprises *M. bovis*, preferably the attenuated and avirulent *M. bovis* as described herein, and at least one antigen each of *Pasteurella haemolytica, Pasteurella multocida* and *H. somnus* [combo 143].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, *Pasteurella haemolytica, Pasteurella multocida* and *H. somnus* [combo 144]. According to a preferred embodiment, the combination vaccine comprises *M. bovis*, preferably the attenuated and avirulent *M. bovis* as described herein, and at least one antigen each of IBR, preferably as live modified virus, *Pasteurella haemolytica, Pasteurella multocida* and *H. somnus* [combo 145].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, *Pasteurella haemolytica, Pasteurella multocida* and *H. somnus* [combo 146]. According to a preferred embodiment, the combination vaccine comprises *M. bovis*, preferably the attenuated and avirulent *M. bovis* as described herein, and at least one antigen each of IBR, PI-3, preferably as live modified viruses, *Pasteurella haemolytica, Pasteurella multocida* and *H. somnus* [combo 147].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), preferably attenuated BVDV (type 1 and/or type 2), *Pasteurella haemolytica, Pasteurella multocida* and *H. somnus* [combo 148]. According to a preferred embodiment, the combination vaccine comprises *M. bovis*, preferably the attenuated and avirulent *M. bovis* as described herein, and at least one antigen each of IBR, PI-3, BVDV (type 1 and/or type 2), preferably attenuated BVDV (type 1 and/or type 2), preferably as live modified viruses, and *Pasteurella haemolytica, Pasteurella multocida* and *H. somnus* [combo 149].

According to a further embodiment, the present invention relates to a combination vaccine for the treatment and/or prophylaxis of cattle against infections in cattle, wherein the combination vaccine comprises *M. bovis*, preferably the attenuated and avirulent *M. bovis* as described herein, and further immunologically active components effective for the treatment and/or prophylaxis of infections caused by IBR, PI-3, BVDV (type 1 and/or type 2), BHV, *Pasteurella haemolytica, Pasteurella multocida* and *H. somnus* [combo 150]. According to a preferred embodiment, the combination vaccine comprises *M. bovis*, preferably the attenuated and avirulent *M. bovis* as described herein, and at least one antigen each of IBR, PI-3, BVDV (type 1 and/or type 2), BHV, preferably as live modified viruses, *Pasteurella haemolytica, Pasteurella multocida* and *H. somnus* [combo 151].

According to a further embodiment, the present invention relates to a combination vaccine according to any one of [combo 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 and 151], that further comprises immunologically active components effective for the treatment and/or prophylaxis of infections caused by one or more pathogenic species of *Leptospira*, preferably selected from the group consisting of *Leptospira canicola, Leptospira grippotyphosa, Leptospira borgpetersenii, Leptospira hardjo, Leptospira prajitno, Leptospira icterohaemmorrhagiae, Leptospira bovis, Leptospira interrogans* and *Leptospira pomona* [combo 152]. According to a further embodiment, the present invention relates to a combination vaccine according to any one of [combo 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 and 151], that further comprises one or more antigens each of one or more specie(s) of *Leptospira*, preferably selected from the group consisting of *Leptospira canicola, Leptospira grippotyphosa, Leptospira borgpetersenii, Leptospira hardjo (Leptospira hardjoprajitno* and *Leptospira hardjo-bovis), Leptospira prajitno, Leptospira icterohaemmorrhagiae, Leptospira bovis, Leptospira interrogans* and *Leptospira pomona*. [combo 153].

According to a further embodiment, the present invention relates to a combination vaccine according to any one of [combo 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 and 151], that further comprises an immunologically active component effective for the treatment and/or prophylaxis of infections caused by *Campylobacter fetus* [combo 154]. According to a further embodiment, the present invention relates to a combination vaccine according to any one of [combo 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 and 151], that further comprises antigen of *Campylobacter fetus* [combo 155].

According to a further embodiment, the present invention relates to a combination vaccine according to any one of [combo 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 and 151], that further comprises an immunologically active component effective for the treatment and/or prophylaxis of infections caused by one or more pathogenic specie(s) of *Leptospira*, preferably selected from the group consisting of *Leptospira canicola, Leptospira grippotyphosa, Leptospira borgpetersenii, Leptospira hardjo (Leptospira hardjoprajitno* and *Leptospira hardjo-bovis), Leptospira prajitno, Leptospira icterohaemmorrhagiae, Leptospira bovis, Leptospira interrogans* and *Leptospira pomona*, and *Campylobacter fetus* [combo 156]. According to a further embodiment, the present invention relates to a combination vaccine according to any one of [combo 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 and 151], that further comprises one or more antigen each of *Campylobacter fetus* and of one or more specie(s) of *Leptospira*, preferably selected from the group consisting of *Leptospira canicola, Leptospira grippotyphosa, Leptospira borgpetersenii, Leptospira hardjo (Leptospira hardjoprajitno* and *Leptospira hardjo-bovis), Leptospira prajitno, Leptospira icterohaemmorrhagiae, Leptospira bovis, Leptospira interrogans* and *Leptospira pomona*, and. [combo 157].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and at least one further immunologically active component effective for the treatment and/or prophylaxis of infections caused by *Clostridium perfringens*, preferably Types A, C and/or D [combo 158]. According to a preferred embodiment, the combination vaccine comprises *M. bovis*, preferably the attenuated and avirulent *M. bovis* as described herein, and toxins of *Clostridium perfringens* Types C and D [combo 254]. According to a more preferred embodiment, said vaccine comprises antigens, preferably toxins, of *Clostridium perfringens*, preferably Types A, B, C, and/or D [combo 159].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises an immunologically active component effective for the treatment and/or prophylaxis of infections caused by infections caused by *Clostridium perfringens*, preferably Types A, C and/or D [combo 160]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises antigen of *Clostridium perfringens*, preferably, Types A, C, and/or D [combo 161]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises antigen of *Clostridium perfringens* Types, B, C, and/or D [combo 162].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Clostridium perfringens* Types A, C and/or D, and *Clostridium tetani* [combo 163]. According to a preferred embodiment, the combination vaccine comprises *M. bovis*, preferably the attenuated and avirulent *M. bovis* as described herein, and toxins of *Clostridium perfringens* Types A, C and/or D, and *Clostridium tetani* [combo 164]. According to a more preferred embodiment, said vaccine comprises antigens, preferably toxins, of *Clostridium perfringens* Types A, B, C, and/or D, and *Clostridium tetani* [combo 165].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises immunologically active components effective for the treatment and/or prophylaxis of infections caused by infections caused by *Clostridium perfringens* Types A, C and/or D, and *Clostridium tetani* [combo 166]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises antigen of *Clostridium perfringens* Types A, C, and/or D, and *Clostridium tetani* [combo 167]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises one or more antigens of *Clostridium perfringens* Types A, B, C, and/or D, and *Clostridium tetani* [combo 168].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Clostridium chauvoei, Clostridium septicum, Clostridium novyi, Clostridium sordellii*, and *Clostridium perfringens* Types A, C and/or D [combo 169]. According to a preferred embodiment, the combination vaccine comprises *M. bovis*, preferably the attenuated and avirulent *M. bovis* as described herein, and one or more antigens, preferably toxins, each of *Clostridium chauvoei, Clostridium septicum, Clostridium novyi, Clostridium sordellii*, and *Clostridium perfringens* Types A, C and/or D [combo 170].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises immunologically active components effective for the treatment and/or prophylaxis of infections caused by infections caused by *Clostridium chauvoei, Clostridium septicum, Clostridium novyi, Clostridium sordellii*, and *Clostridium perfringens* Types A, C and/or D [combo 171]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises one or more antigens each of *Clostridium chauvoei, Clostridium septicum, Clostridium novyi, Clostridium sordellii*, and *Clostridium perfringens* Types A, C and/or D [combo 172].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 and 157], that further comprises one or more antigens each of *Clostridium perfringens* Types, A, B, C, and/or D, *Clostridium chauvoei, Clostridium septicum, Clostridium novyi, Clostridium sordellii* and *Clostridium tetani* [combo 173].

According to more preferred embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Clostridium chauvoei, Clostridium septicum, Clostridium novyi, Clostridium sordellii, Clostridium perfringens* Types A, C and/or D and BRSV [combo 174]. According to a preferred embodiment, the combination vaccine comprises *M. bovis*, preferably the attenuated and avirulent *M. bovis* as described herein, and one or more antigens, preferably toxins, each of *Clostridium chauvoei, Clostridium septicum, Clostridium novyi, Clostridium sordellii*, and *Clostridium perfringens* Types A, C and/or D and *Mycoplasma bovis* [combo 175].

According to more preferred embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Clostridium chauvoei, Clostridium septicum, Clostridium novyi, Clostridium sordellii, Clostridium perfringens* Types A, C and/or D, and *H. somnus*. [combo 176]. According to a preferred embodiment, the combination vaccine comprises *M. bovis*, preferably the attenuated and avirulent *M. bovis* as described herein, and one or more antigens, preferably toxins, each of *Clostridium chauvoei, Clostridium septicum, Clostridium novyi, Clostridium sordellii*, and *Clostridium perfringens* Types C and D and *H. somnus*. [combo 177].

According to more preferred embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Clostridium chauvoei, Clostridium septicum, Clostridium novyi, Clostridium sordellii, Clostridium perfringens* Types A, C and/or D, BRSV, and *H. somnus* [combo 178]. According to a preferred embodiment, the combination vaccine comprises *M. bovis*, preferably the attenuated and avirulent *M. bovis* as described herein, and one or more antigens, preferably toxins, each of *Clostridium chauvoei, Clostridium septicum, Clostridium novyi, Clostridium sordellii*, and *Clostridium perfringens* Types A, C and/or D, *Mycoplasma bovis*, and *H. somnus* [combo 179].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Salmonella*, preferably *Salmonella dublin, Salmonella newport* and *Salmonella typhimurium* [combo 180]. According to a preferred embodiment, the combination vaccine comprises *M. bovis*, preferably the attenuated and avirulent *M. bovis* as described herein, and one or more toxins of *Salmonella*, preferably each of *Salmonella dublin, Salmonella newport*, and/or *Salmonella typhimurium* [combo 181].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178 and 179], that further comprises immunologically active components effective for the treatment and/or prophylaxis of infections caused by infections caused by *Salmonella*, preferably *Salmonella dublin, Salmonella newport* and *Salmonella typhimurium* [combo 182]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178 and 179], that further comprises one or more antigens, preferably toxins, of *Salmonella*, preferably each of *Salmonella dublin, salmonella newport* and/or *Salmonella typhimurium* [combo 183].

According to a preferred embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Pasteurella haemolytica, Pasteurella multocida, Salmonella*, preferably *Salmonella dublin, Salmonella newport* and *Salmonella typhimurium* [combo 184]. According to a preferred embodiment, the combination vaccine comprises *M. bovis*, preferably the attenuated and avirulent *M. bovis* as described herein, and *Pasteurella haemolytica, Pasteurella multocida, Salmonella*, preferably *Salmonella dublin, Salmonella newport*, and *Salmonella typhimurium* Bacterin-Toxoid [combo 185]. According to more preferred embodiment, said combination vaccine comprises multiple isolates of *Pasteurella haemolytica* Type A1 and an associated toxoid fraction, and single isolates of *P. multocida, S. dublin*, and *S. typhimurium* [combo 186].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Moraxella bovis* and/or *Klebsiella* spp., preferably *Klebsiella pneumoniae* [combo 187]. According to a preferred embodiment, the combination vaccine comprises *M. bovis*, preferably the attenuated and avirulent *M. bovis* as described herein, and one or more toxins each of *Moraxella bovis* and/or *Klebsiella* spp. preferably *Klebsiella pneumoniae* [combo 188].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, and 186], that further comprises immunologically active components effective for the treatment and/or prophylaxis of infections caused by infections caused by *Moraxella bovis* and/or *Klebsiella* spp., preferably *Klebsiella pneumoniae* [combo 189]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 163, 164, 165, 169, 170, 174, 175, 176, 177, 178, 179, 180, 181, 184, 185 and 186], that further comprises one or more antigens, preferably toxins, each of *Moraxella bovis* and/or *Klebsiella* spp., preferably, *Klebsiella pneumoniae* [combo 190].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Escherichia coli* [combo 191]. According to a preferred embodiment, the combination vaccine comprises *M. bovis*, preferably the attenuated and avirulent *M. bovis* as described herein, and one or more toxins of *Escherichia coli* [combo 192].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189 and 190], that further comprises an immunologically active component effective for the treatment and/or prophylaxis of infections caused by infections caused by *Escherichia coli* [combo 193]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189 and 190], that further comprises antigen, preferably a toxin, of *Escherichia coli* [combo 194].

According to a preferred embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Pasteurella haemolytica, Pasteurella multocida, Salmonella dublin, Salmonella typhimurium* and *Escherichia coli* [combo 195]. According to a preferred embodiment, the combination vaccine comprises *M. bovis*, preferably the attenuated and avirulent *M. bovis* as described herein, and one or more antigens each of *Pasteurella haemolytica, Pasteurella multocida, Salmonella dublin, Salmonella typhimurium* and *Escherichia coli* Bacterin-Toxoid [combo 196]. According to more preferred embodiment, said combination vaccine comprises multiple isolates of *Pasteurella haemolytica* Type A1 and an associated toxoid fraction, and single isolates of *P. multocida, S. dublin*, and *S. typhimurium* [combo 197].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by bovine Rotavirus [combo 198]. According to a preferred embodiment, the combination vaccine comprises *M. bovis*, preferably the attenuated and avirulent *M. bovis* as described herein and antigen of bovine Rotavirus [combo 199].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 195, 196, and 197], that further comprises an immunologically active component effective for the treatment and/or prophylaxis of infections caused by infections caused by bovine Rotavirus [200]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196 and 197], that further comprises antigen of bovine Rotavirus [combo 201].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and at least one further immunologically active component effective for the treatment and/or prophylaxis of infections caused by bovine Coronavirus [combo 202]. According to a preferred embodiment, the combination vaccine comprises *M. bovis*, preferably the attenuated and avirulent *M. bovis* as described herein, and antigen of bovine Coronavirus [combo 203].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196 and 197], that further comprises an immunologically active component effective for the treatment and/or prophylaxis of infections caused by infections caused by bovine Coronavirus [combo 204]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, and 197], that further comprises antigen of bovine Coronavirus [combo 205].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein and further immunologically active components effective for the treatment and/or prophylaxis of infections caused by bovine Coronavirus and bovine Rotavirus [combo 206]. According to a preferred embodiment, the combination vaccine comprises *M. bovis*, preferably the attenuated and avirulent *M. bovis* as described herein and one or more antigens each of bovine Coronavirus and bovine Rotavirus [combo 207].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196 and 197], that further comprises immunologically active components effective for the treatment and/or prophylaxis of infections caused by infections caused by bovine Coronavirus and bovine Rotavirus [combo 208]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, and 197], that further comprises one or more antigens each of bovine Coronavirus and bovine Rotavirus [combo 209].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and at least one further immunologically active component effective for the treatment and/or prophylaxis of infections caused by *Cryptosporidium parvum* [combo 210]. According to a preferred embodiment, the combination vaccine comprises *M. bovis*, preferably the attenuated and avirulent *M. bovis* as described herein, and antigen of *Cryptosporidium parvum* [combo 211].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184 184, 185, 186, 187, 188, 189, 190, 191, 192, 193, 194, 195, 196, 197, 198, 199, 200, 201, 202, 203, 204, 205, 206, 207, 208 and 209], that further comprises an immunologically active component effective for the treatment and/or prophylaxis of infections caused by infections caused by *Cryptosporidium parvum* [combo 212]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208 and 209], that further comprises antigen of *Cryptosporidium parvum* [combo 213].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and at least one further immunologically active component effective for the treatment and/or prophylaxis of infections caused by *Cryptosporidium hominis* [combo 214]. According to a preferred embodiment, the combination vaccine comprises *M. bovis*, preferably the attenuated and avirulent *M. bovis* as described herein, and antigen of *Cryptosporidium hominis* [combo 215].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184 184, 185, 186, 187, 188, 189, 190, 191, 192, 193, 194, 195, 196, 197, 198, 199, 200, 201, 202, 203, 204, 205, 206, 207, 208 and 209], that further comprises an immunologically active component effective for the treatment and/or prophylaxis of infections caused by infections caused by *Cryptosporidium hominis* [combo 216]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208 and 209], that further comprises antigen of *Cryptosporidium hominis* [combo 217].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Cryptosporidium parvum* and *Cryptosporidium hominis* [combo 218]. According to a preferred embodiment, the combination vaccine comprises *M. bovis*, preferably the attenuated and avirulent *M. bovis* as described herein, and one or more antigens each of *Cryptosporidium parvum* and *Cryptosporidium hominis* [combo 219].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184 184, 185, 186, 187, 188, 189, 190, 191, 192, 193, 194, 195, 196, 197, 198, 199, 200, 201, 202, 203, 204, 205, 206, 207, 208 and 209], that further comprises immunologically active components effective for the treatment and/or prophylaxis of infections caused by infections caused by *Cryptosporidium parvum* and *Cryptosporidium hominis* [combo 220]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208 and 209], that further comprises one or more antigens each of *Cryptosporidium parvum* and *Cryptosporidium hominis* [combo 221].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and at least one further immunologically active component effective for the treatment and/or prophylaxis of infections caused by *Mycobacterium avium* paratuberculosis [combo 222]. According to a preferred embodiment, the combination vaccine comprises *M. bovis*, preferably the attenuated and avirulent *M. bovis* as described herein, and antigen of *Mycobacterium avium paratuberculosis* [combo 223].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220 and 221], that further comprises an immunologically active component effective for the treatment and/or prophylaxis of infections caused by infections caused by *Mycobacterium avium* paratuberculosis [combo 224]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208, 209, 210, 211, 212, 213, 214, 215, 216, 217, 218, 219, 220 and 221], that further comprises antigen of *Mycobacterium avium* paratuberculosis [combo 225].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and at least one further immunologically active component effective for the treatment and/or prophylaxis of infections caused by Adenovirus [combo 226]. According to a preferred embodiment, the combination vaccine comprises *M. bovis*, preferably the attenuated and avirulent *M. bovis* as described herein, and antigen of Adenovirus [combo 227].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224 and 225], that further comprises an immunologically active component effective for the treatment and/or prophylaxis of infections caused by infections caused by Adenovirus [combo 228]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208, 209, 210, 211, 212, 213, 214, 215, 216, 217, 218, 219, 220, 221, 222, 223, 224, and 225], that further comprises antigen of Adenovirus [combo 229].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and at least one further immunologically active component effective for the treatment and/or prophylaxis of infections caused by Astrovirus [combo 230]. According to a preferred embodiment, the combination vaccine comprises *M. bovis*, preferably the attenuated and avirulent *M. bovis* as described herein, and antigen of Astrovirus [combo 231].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228 and 229], that further comprises an immunologically active component effective for the treatment and/or prophylaxis of infections caused by infections caused by Astrovirus [combo 232]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208, 209, 210, 211, 212, 213, 214, 215, 216, 217, 218, 219, 220, 221, 222, 223, 224, 225, 226, 227, 228 and 229], that further comprises antigen of Astrovirus [combo 233].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and at least one further immunologically active component effective for the treatment and/or prophylaxis of infections caused by bovine Parvovirus [combo 234]. According to a preferred embodiment, the combination vaccine comprises *M. bovis*, preferably the attenuated and avirulent *M. bovis* as described herein, and antigen of bovine Parvovirus [combo 235].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232 and 233], that further comprises an immunologically active component effective for the treatment and/or prophylaxis of infections caused by infections caused by bovine Parvovirus [combo 236]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208, 209, 210, 211, 212, 213, 214, 215, 216, 217, 218, 219, 220, 221, 222, 223, 224, 225, 226, 227, 228, 229, 230, 231, 232, and 233], that further comprises antigen of bovine Parvovirus [combo 237].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Cryptosporidium parvum*, Adenovirus, Astrovirus, bovine Parvovirus and *Mycobacterium avium paratuberculosis* [combo 238]. According to a preferred embodiment, the combination vaccine comprises *M. bovis*, preferably the attenuated and avirulent *M. bovis* as described herein, and one or more antigens each of *Cryptosporidium parvum*, Adenovirus, Astrovirus, bovine Parvovirus and *Mycobacterium avium paratuberculosis* [combo 239].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Escherichia coli, Salmonella* spp., preferably *Sal-* monella dublin, Salmonella typhimurium* and *Salmonella newport*, bovine Rotavirus and bovine Coronavirus, *Cryptosporidium parvum*, Adenovirus, Astrovirus, bovine Parvovirus and *Mycobacterium avium paratuberculosis* [combo 240]. According to a preferred embodiment, the combination vaccine comprises *M. bovis*, preferably the attenuated and avirulent *M. bovis* as described herein, and one or more antigens each of *Escherichia coli, Salmonella* spp., preferably *Salmonella dublin, Salmonella typhimurium* and *Salmonella newport*, bovine rotavirus and bovine Coronavirus, *Cryptosporidium parvum*, Adenovirus, Astrovirus, bovine Parvovirus and *Mycobacterium avium paratuberculosis* [combo 241].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Streptococcus* spp., preferably *Streptococcus uberis* and/or *Streptococcus dysgalactiae* [combo 242]. According to a preferred embodiment, the combination vaccine comprises *M. bovis*, preferably the attenuated and avirulent *M. bovis* as described herein, and antigen of *Streptococcus* spp., preferably each of *Streptococcus uberis* and/or *Streptococcus dysgalactiae*, [combo 243]. According to a more preferred embodiment, the combination vaccine comprises *M. bovis*, preferably the attenuated and avirulent *M. bovis* as described herein, and one or more antigens of *Streptococcus* spp., preferably each of *Streptococcus uberis* and/or *Streptococcus dysgalactiae* [combo 244].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Streptococcus* spp., preferably *Streptococcus uberis* and/or *Streptococcus dysgalactiae* and/or *Staphylococcus aureus* [combo 245]. According to a more preferred embodiment, the combination vaccine comprises *M. bovis*, preferably the attenuated and avirulent *M. bovis* as described herein, and one or more antigens of *Streptococcus* spp., preferably each of *Streptococcus uberis* and/or *Streptococcus dysgalactiae*, and/or *Staphylococcus aureus* [combo 246].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, and 241], that further comprises immunologically active components effective for the treatment and/or prophylaxis of infections caused by infections caused by *Streptococcus* spp., preferably *Streptococcus uberis* and/or *Streptococcus dysgalactiae*, and/or *Staphylococcus aureus* [combo 247]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240 and 241], that further comprises one or more antigens each of *Streptococcus* spp., preferably *Streptococcus uberis* and/or *Streptococcus dysgalactiae*, and/or *Staphylococcus aureus* [combo 248]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240 and 241], that further comprises one or more antigens of several serotypes of *Streptococcus* spp., preferably of several serotypes each of *Streptococcus uberis* and/or *Streptococcus dysgalactiae*, and/or *Staphylococcus aureus* [combo 249].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Streptococcus* spp., preferably *Streptococcus*

*uberis, Streptococcus dysgalactiae* and/or *Staphylococcus aureus, Klebsiella* spp. and *Mycoplasma* spp. [combo 250]. According to a preferred embodiment, the combination vaccine comprises *M. bovis*, preferably the attenuated and avirulent *M. bovis* as described herein, and one or more antigens of *Streptococcus* spp., preferably each of *Streptococcus uberis, Streptococcus dysgalactiae*, and/or *Streptococcus aureus, Klebsiella* spp. and *Mycoplasma* spp. [combo 251]. According to a more preferred embodiment, the combination vaccine comprises *M. bovis*, preferably the attenuated and avirulent *M. bovis* as described herein, and one or more antigens of *Streptococcus* spp., preferably each of *Streptococcus uberis* and/or *Streptococcus dysgalactiae, Staphylococcus aureus, Klebsiella* spp., *Mycoplasma* spp. and endotoxin [combo 252].

According to a further embodiment, the present invention relates to a combination vaccine for the treatment and/or prophylaxis of cattle against microbiological infections in cattle, wherein the combination vaccine comprises *M. bovis*, preferably the attenuated and avirulent *M. bovis* as described herein, and further immunologically active components effective for the treatment and/or prophylaxis of infections caused by *Trichophyton* and *Microsporum*, preferably selected from the group consisting of *Trichophyton verrucosum, Trichophyton mentagrophytes, Trichophyton equinum, Trichophyton sarkisovii, Microsporum canis, Microsporum canis* var. *obesum, Microsporum canis* var. *distortum*, and *Microsporum gypseum* [combo 253]. According to a preferred embodiment, the combination vaccine comprises *M. bovis*, preferably the attenuated and avirulent *M. bovis* as described herein, and one or more antigens each of *Trichophyton*, and *Microsporum*, preferably selected from the group consisting of *Trichophyton verrucosum, Trichophyton mentagrophytes, Trichophyton equinum, Trichophyton sarkisovii, Microsporum canis, Microsporum canis* var. *obesum, Microsporum canis* var. *distortum*, and *Microsporum gypseum* [combo 254].

According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, and 251], that further comprises immunologically active components effective for the treatment and/or prophylaxis of infections caused by infections caused by *Trichophyton* and *Microsporum*, preferably selected from the group consisting of *Trichophyton verrucosum, Trichophyton mentagrophytes, Trichophyton equinum, Trichophyton sarkisovii, Microsporum canis, Microsporum canis* var. *obesum, Microsporum canis* var. *distortum*, and *Microsporum gypseum* [combo 255]. According to a further embodiment, the present invention relates to a combination vaccine according to any one of [combo 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037, 038, 039, 040, 041, 042, 043, 044, 045, 046, 047, 048, 049, 050, 051, 052, 053, 054, 055, 056, 057, 058, 059, 060, 061, 062, 063, 064, 065, 066, 067, 068, 069, 070, 071, 072, 073, 074, 075, 076, 077, 078, 079, 080, 081, 082, 083, 084, 085, 086, 087, 088, 089, 090, 091, 092, 093, 094, 095, 096, 097, 098, 099, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 254, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, and 252], that further comprises one or more antigens each of *Trichophyton* and *Microsporum*, preferably selected from the group consisting of *Trichophyton verrucosum, Trichophyton mentagrophytes, Trichophyton equinum, Trichophyton sarkisovii, Microsporum canis, Microsporum canis* var. *obesum, Microsporum canis* var. *distortum*, and *Microsporum gypseum* [combo 256].

According to a further aspect, the present invention also relates to the combined use or co-administration of any of the antigens provided in the combination vaccines [combo 1 to combo 256]. Preferably, the *M. bovis* antigen is provided in a first immunogenic composition, and any other antigen/antigens are provided in one or more further immunogenic compositions to be administered.

According to further embodiment, the immunologically active component(s) effective for the treatment and/or prophylaxis of infections caused by one or more cattle relevant pathogen(s) as source of the combination vaccine provided herewith is any one included in the vaccines selected from the group consisting of: Alpha 7™, ALPHA-7/MB™, ALPHA-CD™, BAR-VAC® 7, BAR-VAC® 7/SOMNUS, BAR-VAC® 8, BAR-VAC® CD, BAR-VAC® C/DT, BREED-BACK™ FP 10, BREED-BACK™ FP 10 HS, BREED-BACK™ FP 5, BREED-BACK™ FP 5 HS, BREED-BACK-10™, CALIBER® 3, CALIBER® 7, ELITE 4™, ELITE 9™, ELITE 9-HS™, EXPRESS® 10, EXPRESS® 10-HS, EXPRESS® 3, EXPRESS® 3/Lp, EXPRESS 4®, EXPRESS® 5, EXPRESS® 5-HS, EXPRESS® 5-PHM, EXPRESS® I, EXPRESS® I/LP, OCU-GUARD® MB, PULMO-GUARD™ MpB, PULMO-GUARD™ PH-M, PULMO-GUARD™ PH-M/SDT, PULMO-GUARD™ PHM-1, TETGUARD™, VIBRIO-LEPTO-5™ (all of Boehringer Ingelheim, St. Joseph, Mo.); Cobalt™ 7, I-Site™, Lepto 5, Master Guard® Preg 5, Master Guard® 10, Master Guard® 10+Vibrio, Master Guard® J5, P.H.M. Bac® 1, Prevent 6™, Respromune® 4, Respromune® 4+Somnumune® (IM, SC), Respromune® 5 I-B-P+BRSV, Respromune® 5+L5, Respromune® 5+L5 Somnus, Respromune® 5+Somnumune, Respromune® 5+VL5, Respromune® 8, Respromune® 9, Respromune® 10, Scour Vac™ 4, Scour Vac™ 9, Scour Vac™ *E. coli*+C, Somnumune®, Titanium™ 3, Titanium™ 4, Titanium™ 4 L5, Titanium™ 5, Titanium™ 5 L5, Titanium® 5+P.H.M. Bac®-1, Titanium™ BRSV 3, Titanium™ IBR, Titanium™ IBR-LP (all of Agri Laboratories Inc., St. Joseph, Mo.); Herd-Vac® 3, Herd-Vac® 3S, Herd-Vac® 8, Herd-Vac® 9, Surround™ 4, Surround™ 4+HS, Surround™ 8, Surround™ 9, Surround™ 9+HS, Surround™ HS, Surround™ L5, Surround™ V-L5 (all of BioCor, Omaha, Nebr. (Pfizer)); Mycomune® (Biomune Co., Lenexa, Kans.); Bluetongue vaccine, Bovine Virus Diarrhea Vaccine, *Campylobacter fetus* bacterin-bovine, Essential 1, Essential 2, Essential 2+P, Essential 3, Essential 3+T, Essential 4, Lepto-5, *Mannheimia haemolytica-Pasteurella multocida* bacterin, Pre-breed 6, Pre-breed 8, Respira-1, Respira-3, Wart Vaccine (all of Colorado Serum Company, Denver, Colo.); Pyramid® 3, Pyramid® 4, Pyramid® 4+Presponse® SQ, Pyramid® 5, Pyramid® 8, Pyramid® 9, Pyramid® IBR, Pyramid® IBR+Lepto, Triangle® 1+Type II BVD, Triangle® 3+VL5, Triangle® 4+HS, Triangle® 4+PH/HS, Triangle® 4+PH-K, Triangle® 4+Type II BVD, Triangle® 9+HS, Triangle® 9+PH-K, Triangle®+Type II BVD, Trichguard®, Trichguard®+V5L, TriVib 5L® (all of Fort Dodge Animal Health, Overland Park, Kans. (Wyeth)); J-5 *Escherichia coli* Bacterin, Serpens Species Bacterin; *Staphylococcus aureus* bacterin-toxoid (all of Hygieia Biological Laboratories, Woodland, Calif.); Endovac-Bovi® with Immuneplus® (Immvac, Inc., Columbia, Mo.); 20/20 Vision® with Spur®, L5 SQ, Neoguard™, MasterGuard® Preg 5, Once PMH®, Once PMH® SQ, Vibralone™-L5, Vision® 7 Somnus with Spur®, Vision® 7 with Spur®, Vision® 8 Somnus with Spur®, Vision® 8 with Spur®, Vision® CD-T with Spur®, Vision® CD with Spur®, Vista™ IBR SQ, Vista™ 3 SQ, Vista™ 5 SQ, Vista™ 5 L5 SQ, Vista™ Once SQ, VL5 SQ, Volar®, (all of Intervet Inc., Millsboro, Del.); Vac®, Reliant® 3, Reliant® 4, Reliant® IBR, Reliant® IBR/BVD, Reliant® IBR/Lepto, Reliant® Plus BVD-K (Dual IBR™), Reliant® Plus (Dual IBR™), Respishield™ 4, Respishield™ 4 L5, Respishield™ HM (all of Merial LTD, Duluth, Ga.); Arsenal® 4.1, Arsenal® IBR, Arsenal® IBR BVD, Bovine Pili Shield™, Bovine Pili Shield™+C, Clostri Shield® 7, Clostri Shield® BCD, Fusogard®, Lepto Shield™ 5, Pinkeye Shield™ XT4, Salmo Shield® T, Salmo Shield® TD, Scour Bos™ 4, Scour Bos™ 9, Somnu Shield™, Trep Shield™ HW, Vib Shield® L5, Vib Shield® Plus, Vib Shield® Plus L5, Vira Shield® 2, Vira Shield® 2+BRSV, Vira Shield® 3, Vira Shield® 3+VL5, Vira Shield® 4, Vira Shield® 4+L5, Vira Shield® 5, Vira Shield® 5+L5, Vira Shield® 5+L5 Somnus, Vira Shield® 5+Somnus, Vira Shield® 5+VL5, Vira Shield® 5+VL5 Somnus, Vira Shield® 6, Vira Shield® 6+Somnus, Wart Shield™ (all of Novartis Animal Health, Basel, Switzerland); Bovi-K® 4, Bovi-Shield™ 3, Bovi-Shield™ 4, Bovi-Shield™ BRSV, Bovi-Shield® FP™ 4+L5, Bovi-Shield® GOLD 3, Bovi-Shield® GOLD 5, Bovi-Shield® GOLD FP™ 5 L5, Bovi-Shield® GOLD FP™ 5 VL5, Bovi-Shield® Gold IBR-BVD, Bovi-Shield® Gold IBR-BVD-BRSV-LP, Bovi-Shield™ IBR, Bovi-Shield™ IBR-BRSV-LP, Bovi-Shield™ IBR-BVD, Bovi-Shield™ IBR-BVD-BRSV-LP, Bovi-Shield™ IBR-PI3-BRSV, Calf-Guard®, CattleMaster® 4, CattleMaster® 4+L5, CattleMaster® 4+VL5, CattleMaster® BVD-K, CattleMaster® Gold FP™ 5, CattleMaster® Gold FP™ 5 L5, Defensor® 3, Fortress® 7, Fortress® 8, Fortress® CD, Leptoferm®-5, One Shot®, One Shot Ultra™ 7, One Shot Ultra™ 8, PregGuard™ FP 9, PregGuard® Gold FP™ 10, Resvac® BRSV/Somubac®, Resvac® 4/Somubac®, Scour-Guard 3® (K), ScourGuard 3® (K)/C, Somubac®, Spirovac®, Spirovac® L5, Spirovac® VL5, StayBred™ VL5, TSV-2™, Ultrabac® 7, Ultrabac® 7/Somubac®, Ultrabac® 8, Ultrabac® CD, UltraChoice™ 7, UltraChoice™ 8, UltraChoice™ CD, Upjohn J-5 Bacterin™, Vibrin® (all of Pfizer Inc., New York, N.Y.); Covexin® 8 Vaccine, Electroid® 7 Vaccine, Electroid® D, Guardian™, Jencine® 2, Jencine® 3, Jencine® 4, Nasalgen® IP Vaccine, Piliguard® Pinkeye-1 Trivalent, Piliguard® Pinkeye+7, Piliguard® Pinkeye Triview®, Siteguard® G, Siteguard® MLG Vaccine (all of Schering-Plough Animal Health Corporation, Kenilworth, N.J.); Myco-Bac™ B, Poly-Bac B® 3, Poly-Bac B® Somnus, Super Poly-Bac B® Somnus (all of Texas Vet Lab, Inc., San Angelo, Tex.), Virabos™-3 with Immunostim®, Virabos™-4+*H. somnus* with Immunostim®, and Virabos™-4 with Immunostim® (all of Bioniche Animal Health, Athens, Ga.), wherein the *M. bovis* antigen, preferably the attenuated, avirulent *M. bovis* as described herein, is added. Alternatively, when *M. bovis* antigen is present in any of those vaccines, attenuated avirulent *M. bovis*, as described herein, is added, or the *M. bovis* antigen present any of those vaccines is substituted by the attenuated, avirulent *M. bovis* as described herein.

Formulations

A further aspect of the present invention is the preparation of the combination vaccine(s). One of skill in the art can determine additional components which are present in the composition of the invention. (see also Remington's Pharmaceutical Sciences, (1990) 18th ed. Mack Publ., Easton). Known injectable, physiologically acceptable sterile solutions may be used. For preparing a ready-to-use solution for parenteral injection or infusion, aqueous isotonic solutions, such as e.g. saline or corresponding plasma protein solutions, are readily available. The pharmaceutical compositions of the present invention may be present as lyophylisates or dry preparations, which can be reconstituted with a known injectable solution directly before use under sterile conditions, e.g. as a kit of parts.

In addition, the immunogenic and vaccine compositions of the present invention can include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like.

Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

Adjuvants include, but are not limited to, the RIBI adjuvant system (Ribi Inc.), alum, aluminum hydroxide gel, Cholesterol, oil-in water emulsions, water-in-oil emulsions such as, e.g., Freund's complete and incomplete adjuvants, Block copolymer (CytRx, Atlanta Ga.), SAF-M (Chiron, Emeryville Calif.), CARBOPOL®, AMPHIGENO adjuvant, saponin, Quil A, QS-21 (Cambridge Biotech Inc., Cambridge Mass.), GPI-0100 (Galenica Pharmaceuticals, Inc., Birmingham, Ala.) or other saponin fractions, monophosphoryl lipid A, Avridine lipid-amine adjuvant, heat-labile enterotoxin from *E. coli* (recombinant or otherwise), cholera toxin, or muramyl dipeptide, among many others.

The immunogenic compositions can further include one or more other immunomodulatory agents such as, e.g., interleukins, interferons, or other cytokines. The immunogenic compositions can also include Gentamicin and Merthiolate. While the amounts and concentrations of adjuvants and additives useful in the context of the present invention can readily be determined by the skilled artisan, preferably the composition comprises from about 50 ug to about 2000 ug of adjuvant and preferably about 250 ug/ml dose of the vaccine composition. In another preferred embodiment, the present invention an antibiotic is present in an amount of from about 1 ug/ml to about 60 ug/ml of and preferably less than about 30 ug/ml.

According to a further embodiment the combination vaccine (or immunogenic composition) is first dehydrated. If the composition is first lyophilized or dehydrated by other methods, then, prior to vaccination, said composition is rehydrated in aqueous (e.g. saline, PBS (phosphate buffered saline)) or non-aqueous solutions (e.g. oil emulsion (mineral oil, or vegetable/metabolizable oil based/single or double emulsion based), aluminum-based, carbomer based adjuvant).

According to a further embodiment, the immunogenic composition or combination vaccine as provided herewith, which comprises at least one *M. bovis* antigen and one or more further immunologically active component(s) effective for the treatment and/or prophylaxis of infections caused by a further cattle relevant pathogen other than *M. bovis* are formulated as fix-dose combination vaccine. Preferably, the immunogenic composition or combination vaccine provided herewith, in particular the fix-dose combination vaccine is formulated for use as a single-dose or multi-dose vaccine, whereas the formulation for use as a single-dose vaccine is most preferred. In other words the immunogenic compositions or vaccine, preferably the fix-dose combination vaccine provided herewith is formulated for the administration as a multi-dose or single-dose, whereas the formulation for the administration as single-dose is most preferred. As shown in the example section, such a single dose administration of the *M. bovis* antigen is effective in lessening or reducing the signs of an *M. bovis* infection. Thus, according to a further embodiment, the immunogenic compositions provided herewith, in particular the fix-dose combination vaccine is formulated for use as a single-dose vaccine, wherein the administration of such single-dose is effective in lessening or reducing the signs of an *M. bovis* infection.

Dose and Administration

According to the present invention, an effective amount of a combination vaccine administered to cattle provides effective immunity against microbiological infections caused by *M. bovis* and at least one further pathogen as listed above. Preferred combinations of antigens for the treatment and prophylaxis of microbiological diseases in cattle are listed above.

In preferred forms, the dose volume of the combination vaccine as well as of each immunogenic composition when separately co-administered is no more than 5 ml, more preferably no more than 3 ml, and more preferably no more than 2 ml. In a most preferred embodiment, the dose is 2 ml, preferably administered intranasally, with 1 ml being administered in each nostril, more preferably administered intramuscularly, even more preferably administered subcutaneously, and most preferably administered both intranasally and subcutaneously on one occasion as a single dose. In some preferred forms, a second or subsequent administration of the immunogenic composition would be administered after the first administration. Such a subsequent administration would preferably occur at least 10 days after the initial administration, more preferably between at least 10-32 days, more preferably between at least 12-30 days, still more preferably at least 14 days, and most preferably between at least 14-28 days. In most preferred forms, the vaccine would be administered either as a single dose, preferably on Day 0 or, in alternative forms, 14-28 days thereafter, preferably on Day 0 and 14-28 days thereafter with exposure to pathogenic forms of *M. bovis* not occurring until after the completion of the immunizing regimen. In a most preferred form, no booster is necessary and the vaccine is administered only one time. The vaccine is administered to animals from 1 day of age through adulthood, preferably to calves from 1 day of age through young adult cattle 2 years of age, more preferably to calves from 1 day of age through 16 weeks of age, and most preferably to calves from 6 weeks to 12 weeks of age. Such administration lessened or reduced signs of *M. bovis* infection as described below. Preferably, signs of *M. bovis* infection in the group vaccinated as described above are reduced by at least 50%, more preferably at least 60%, even more preferably at least 70%, and even more preferably at least 75% in comparison to the non-vaccinated group. Lung pathology assessment, specifically the percentage of lung consolidation attributed to lesions due to *M. bovis*, as customarily scored for various species, was made post-necropsy. Preferably lung lesions are reduced by at least 33%, more preferably at least 50%, even more preferably at least 70%, even more preferably at least 80%, even more preferably at least 90%, and most preferably by at least 95% in comparison to a non-vaccinated group.

The amount of combination vaccine that is effective depends on the ingredients of the vaccine and the schedule of administration. Typically, when bacterial antigen is used in the combination vaccine or in a combined use, the vaccine or immunogenic composition contains an amount of about $10^3$ to about $10^{10}$ colony forming units (CFU) of the bacterial antigen per dose, preferably, about $10^4$ to about $10^9$ CFU of the bacterial antigen per dose, more preferably about $10^5$ to about $10^6$ CFU of the bacterial antigen per dose. For instance, the attenuated, avirulent *M. bovis* is preferably used in amounts of about $10^2$ to about $10^{10}$ CFU per dose, preferably about $10^3$ to about $10^9$ CFU per dose, even more preferably in an amount of about $10^8$ to about $10^{10}$ CFU per dose, most preferably in an amount of about $2.1 \times 10^9$ CFU per dose.

Typically, when an inactivated virus or a modified live virus preparation is used in the combination vaccine or in a combined use, the vaccine or immunogenic composition containing about $10^2$ to about $10^9$ $TCID_{50}$ viral antigen per dose, preferably about $10^3$ to about $10^8$ $TCID_{50}$ viral antigen per dose, more preferably, about $10^4$ to about $10^8$ $TCID_{50}$ viral antigen per dose. For example, about $10^5$ to about $10^8$ $TCID_{50}$ per dose of attenuated BVDV (types 1 and 2) is effective when administered twice to the animal during a period of about 3 to 4 weeks. In general, inactivated antigen is normally used in higher amounts than live modified viruses.

In the event the combination vaccine comprises live modified IBR, the amount of IBR antigen is preferably in a range of about $10^5$ to $10^{7.5}$ $TCID_{50}$ per dose. In the event the combination vaccine comprises live modified PI3, the amount of PI3 antigen is preferably in a range of about $10^7$ to $10^9$ $TCID_{50}$ per dose. In the event the combination vaccine comprises live modified BRSV, the amount of BRSV antigen is preferably in a range of about $10^{4.5}$ to $10^{6.5}$ $TCID_{50}$ per dose. In the event the combination vaccine comprises killed antigens the $TCID_{50}$ or CFU indicates the amount of antigen per dose in the live culture before inactivation, and for IBR, the amount of IBR antigen is preferably in a range of about $10^{7.0}$ to $10^{9.0}$ $TCID_{50}$ per dose. In the event the combination vaccine comprises killed PI3, the amount of PI3 antigen is preferably in a range of about $10^{7.2}$ to $10^{9.2}$ $TCID_{50}$ per dose. In the event the combination vaccine comprises killed BRSV, the amount of BRSV antigen is preferably in a range of about $10^{5.0}$ to $10^{7.5}$ $TCID_{50}$ per dose. In the event the combination vaccine comprises killed *Leptospira* spp. the amount of each *Leptospira* spp. antigen is preferably in a range of about $10^{7.0}$ to $10^{10}$ (CFU) per dose. In the event the combination vaccine comprises killed *H. somnus*, and/or killed *Pasteurella multocida*, and/or killed *Mannheimia haemolytica* the amount of *H. somnus* antigen and/or *Pasteurella multocida* antigen, and/or

*Mannheimia haemolytica* antigen is preferably in a range of about $10^{6.0}$ to $10^{10}$ colony forming unit (CFU) per dose.

Combined Use/Method of Treatment

A further aspect of the present invention relates to the combined use of immunogenic compositions for the treatment and/or prophylaxis of cattle against microbiological infections, wherein the infections are caused by *M. bovis* and at least one further cattle relevant pathogen.

Yet another important embodiment of the invention is a method for the prophylaxis or treatment of diseases caused by *M. bovis*, and further cattle pathogenic microorganism(s), wherein a *M. bovis* antigen, preferably the attenuated, avirulent *M. bovis* as described herein, and further immunologically active components effective for the treatment and/or prophylaxis of the infection caused by said further cattle pathogenic microorganism, preferably as described herein, are administered to an animal in need thereof at a suitable dose, as known to the skilled person.

The combined use or the method of co-administration of two or more antigens of pathogens affecting cattle comprises administering a first immunogenic composition comprising a *M. bovis* antigen, preferably the attenuated, avirulent *M. bovis* as provided herewith, and at least one further immunogenic composition comprising an immunologically active component effective for the treatment and/or prophylaxis of infections caused by a further pathogen of cattle. Preferably, the further pathogen is one of the pathogens as listed herein. Preferably, the first and the further immunogenic compositions are administered separately. Preferably, the further immunogenic composition comprises one or more immunologically active component(s) effective for the treatment and/or prophylaxis of infections caused by a pathogen of cattle other than *M. bovis*. More preferably, the first and the further immunogenic compositions are administered together by means such as mixing before administration and/or by formulating the first and the further immunogenic compositions in a single container.

The co-administration of each of the immunogenic compositions occurs simultaneously, which means at least within 48 hours, preferably within 24 hours, even more preferably within 12 hours, even more preferably within 6 hours, even more preferably within 3 hours, even more preferably within 2, hours, even more preferably within 1 hour. The route of administration of each of the immunogenic compositions depends on the mode-of-action and may be the same, but also could be different.

According to a further embodiment the *M. bovis* antigen as provided herewith and one or more further immunologically active component(s) effective for the treatment and/or prophylaxis of infections caused by a further cattle relevant pathogen other than *M. bovis* can be used a medicament. Preferably, that medicament is a vaccine and can be used for lessening or reducing the signs of a *M. bovis* infection. Most preferably, that medicament or vaccine can be used for lessening or reducing the signs of a *M. bovis* infection and associated with or caused by an infection of the further cattle relevant antigen.

FURTHER DEFINITIONS

An "antigen" or an "immunologically active component" as used herein refer to but is not limited to components which elicit an immunological response in a host of a cellular and/or antibody-mediated immune response to a composition or vaccine of interest comprising said antigen or immunologically active component. The antigen or immunologically active component may be a microorganism that is whole (in inactivated or attenuated or modified live form), or any fragment or fraction thereof, which, if administered to a host, can elicit an immunological response in the host.

An "immunogenic or immunological composition" refers to a composition of matter that comprises at least one antigen, which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of clinical signs normally displayed by an infected host, a quicker recovery time and/or a lowered duration or lowered pathogen titer in the tissues or body fluids or excretions of the infected host. In such case, where the host will display either a therapeutic or protective immunological response such that resistance to new infection will be enhanced and/or the clinical severity of the disease reduced, the immunogenic composition is described as a vaccine.

"Signs of *M. bovis* infection" refers to the manifestations of infection or disease caused by *M. bovis* including both the clinical symptom(s) and pathology typically experienced by cattle infected with wild type *M. bovis*. These manifestations of infection or disease may take many forms including, but not limited to, fever, depression, anorexia, labored breathing, nasal and ocular discharge, coughing, sneezing, gasping, grunting, lameness and swollen joints, middle ear infections, discharge from inflammation of the inner ear, abortions and other reproductive disorders, recumbence, respiratory infection, head tilt, ataxia, arthritis, mastitis, otitis, keratoconjunctivitis, synovitis, pleuritis, lung lesions, lung consolidation and nodular formation in the lungs, increased synovial fluid, thickened joint capsules, joint surface erosions, and even death.

"High Passage strain" for purposes of this disclosure, refers to an *M. bovis* strain that has been passaged more than 10, preferably at least 20, still more preferably at least 30, even more preferably at least 40, still more preferably, at least 50, even more preferably at least 55, still more preferably at least 60, even more preferably at least 70, still more preferably, at least 80, even more preferably at least 90, still more preferably at least 95, even more preferably at least 100, still more preferably at least 102 times, and most preferably at least 106 times in vitro.

"Lung Pathology Assessment" refers to observation of the lungs during necropsy, including, but not limited to, assessment of consolidation, lesions, and nodular formations as well as assessment of the thoracic cavity including pleuritis and fluid accumulation.

"Attenuation" means reducing the virulence of a pathogen. In the present invention "attenuation" is synonymous with "avirulent". In the present invention, an attenuated *M. bovis* bacterium is one in which the virulence has been reduced so that it does not cause clinical signs of a *M. bovis* infection but is capable of inducing an immune response in the target mammal, but may also mean that the clinical signs are reduced in incidence or severity in animals vaccinated with the attenuated *M. bovis* in comparison with a "control group" of animals infected with non-attenuated *M. bovis* and not receiving a vaccination of the attenuated bacterium. In this context, the term "reduce/reduced" means a reduction of at least 10%, preferably 25%, even more preferably 50%, most preferably of more than 100% as compared to the control group as defined above. Thus, an attenuated, avirulent *M. bovis* strain is one that is suitable for incorporation into an immunogenic composition, comprising a modified live *M. bovis* bacterium.

An "effective amount of *M. bovis*" for purposes of the present invention, means an amount of an immunogenic composition capable of inducing an immune response that reduces the incidence of or lessens the severity of *M. bovis* infection in an animal. Particularly, an effective amount refers to 10E3 to 10E10, preferably to 10E6 to 10E10 colony forming units (CFU) per dose.

"Improved efficacy such that clinical signs associated with *M. bovis* infection and/or the *M. bovis* infection itself were reduced in comparison to currently available vaccines when vaccinates are exposed to *M. bovis* or suffer infection by wild-type *M. bovis* strains" refers to a reduction in either the incidence of or severity of clinical signs of *M. bovis* infection when comparing vaccines made from strains passaged as taught by the present invention with *M. bovis* vaccines that were available prior to this invention. In this context, animals not vaccinated, or vaccinated with *M. bovis* vaccines available prior to the present invention will have clinical signs of *M. bovis* infection that are at least 30%, and possibly up to more preferably at least 40%, still more preferably at least 50%, even more preferably at least 60%, still more preferably at least 70%, even more preferably at least 75%, still more preferably at least 80%, even more preferably at least 85%, still more preferably at least 90%, and most preferably at least 95% more severe or prevalent than in animals receiving an administration of an *M. bovis* immunogenic composition in accordance with the present invention.

"Long-lasting protection" shall refer to "improved efficacy" that persists for at least 3 weeks, but more preferably at least 6 months, still more preferably at least 1 year, even more preferably at least 2 years for beef animals, and at least 6 months, more preferably at least 1 year, still more preferably at least 2 years, still more preferably at least 3 years, and even more preferably at least 4 years for dairy animals. For both dairy animals and beef animals, it is most preferred that the long lasting protection shall persist until the average age at which beef animals are marketed for meat and the age at which dairy animals conclude their productive life of milking.

The term "in need of such administration" or "in need of such administration treatment", as used herein, means that the administration/treatment is associated with the boosting or improvement in health or any other positive medicinal effect on health of the animals which receive the immunogenic composition in accordance with the present invention.

"DNA fingerprinting", as used herein, refers to the rapid identification of bacterial strains accomplished by amplifying the DNA between insertion sequences (IS) and measuring the pattern of amplified products as described in WO 2008-030619, hereby incorporated by reference in its entirety. Using PCR and a combination of outwardly facing primers designed against bacterial insertion sequences (transposable elements), patterns are produced that are unique to an isolate of a bacterial species. These patterns can then be compared for such things as epidemiology or phylogeny. One preferred method of DNA fingerprinting utilizes PCR and a combination of outwardly facing primers designed against single or multiple bacterial insertion sequences. Such a method produces amplification products from adjacent IS. Once the PCR amplification is complete, the products are separated (agar gel) and banding patterns are produced, according to the molecular weight of the amplification products, which are unique to an isolate of a bacterial species. The preferred method is to carry out multiplex PCR using outwardly facing primers. Multiplex PCR is a variant of PCR which enables simultaneous amplification of many targets of interest in one reaction by using multiple primer sets. Of course, other molecular-based fingerprinting methods known in the art may also be used.

An "insertion sequence" (IS) is a short DNA sequence that acts as a transposable element. IS are generally around 700 to 2500 bp in length, which is relatively small compared to other types of transposable elements. They code for proteins implicated in transposition activity, wherein the proteins catalyze the enzymatic reaction allowing the IS to move. IS elements are unique to a particular species or can be shared between taxonomic groups. There are usually multiple copies of these insertion sequences, but they are located in unique locations for a specific transposable element.

EXAMPLES

The following examples are representative of preferred embodiments of the present invention. It is understood that nothing herein should be taken as a limitation upon the overall scope of the invention.

Example 1

This Example assessed the efficacy of an experimental live *M. bovis* vaccine using two different challenge models in a target species.

Materials and Methods

Thirty-five colostrum deprived (CD) Holstein calves ranging in age from 4-8 weeks of age were used. All animals met the inclusion criteria, namely that they tested negative for *M. bovis* and were in good health at the time of the challenge. The calves were first randomly assigned to 1 of 4 groups. Groups 1-3 each contained 9 calves, and Group 4 contained 8 calves. Group 1 and 2 calves were vaccinated with Live Vac 1, which is a culture of *M. bovis* isolate 052823 passaged 106 times (05-2823-1A-3A P106+) (ATCC Designation No. PTA-8694) while Group 3 and 4 calves were vaccinated with media only. The vaccine isolate for Groups 1 and 2 was obtained from naturally occurring disease outbreak and then serially passaged 106 times in *M. bovis* appropriate media. The culture was grown 24±2 hours at 37° C. after inoculation with an appropriate volume of seed culture determined before the study. The isolate was used without dilution. The average pre and post vaccination concentration was found to be 2.1E9 CFU/ml. The vaccine was administered in 2 ml doses subcutaneously and in 2 ml doses intranasally (1 ml in each nostril). All study calves were challenged with virulent *M. bovis* to induce the naturally occurring infection and disease with Groups 1 and 3 receiving a higher challenge dose and Groups 3 and 4 receiving a lower challenge dose The doses and administrations of the test substance are summarized in Table 1.

TABLE 1

Group Treatments

| Groups | Animals/group | Test Substance | | | Challenge | | |
|---|---|---|---|---|---|---|---|
| | | Article | Dose/Route | Admin Schedule | Material | Dose | Admin Schedule |
| Group 1 | 9 | M. bovis Live I Testing For microbiological testing, swabs were placed in the transport media and tissue samples were shipped for *M. bovis* isolation. Briefly, swabs were swirled in 5 ml *Mycoplasma* selective broth. A small sample (approximately 5 mm) was cut from lung tissue and homogenized in 2 ml of *Mycoplasma* media. 100 µl of homogenate was added to the *Mycoplasma* selective broth. Cultures were incubated at 37 C/5% CO2. After 4-14 days, the broth was examined for growth and subcultured to plates for isolation. All positive subculture samples were stored at −70 C.

For PCR, swabs from each calf not placed in transport media and tissue samples were shipped for DNA extraction and testing by PCR using primers and probes specific for the uvrC gene of *M. bovis*. Results of PCR testing were expressed as positive or negative for *M. bovis* DNA detection.

For serology testing, serum samples were tested using a commercially available ELISA (Biovet, Canada) using the protocol provided with the test kit. ELISA results were expressed as Optical Density (OD) readings. Sample OD's were compared to the Positivity level (Mean ODp×0.3) established by the positive control included in the test kit. Positive results were then interpreted by the following scale:

| Interval | Interpretation |
|---|---|
| OD sample < Positivity Level | Negative (0) |
| Positivity Level < OD Sample < 1.75 * Positivity Level | +1 |
| 1.75 * Positivity Level < OD Sample < 2.3 * Positivity Level | +2 |
| 2.3 * Positivity Level < OD Sample < 3 * Positivity Level | +3 |
| OD Sample < 3 * Positivity Level | +4 |

For histopathology/IHC testing, formalin-fixed tissues were tested by hematoxylin/eosin stained slide and immunohistochemistry using monoclonal antibodies specific for *M. bovis*. For clinical testing, daily general observations were carried out from Day 0 to Day 28, and then daily clinical observations were made from Day 28 to euthanasia and necropsy. Clinical and general observations that deviated from the norm were noted and documented. At necropsy, the thoracic cavity and trachea were examined for each calf and gross observations recorded. The lungs and about 6 inches of trachea from each calf were removed intact for further examination and sample collection. For each set of lungs, the dorsal and ventral lung surfaces were photographed with an appropriate ear tag alongside each view. For lung pathology, each lung lobe was examined by visualization and by palpation in order to determine how much pathology was present (as a percent) per each lung lobe due to *M. bovis*. Each lung lobe percent was then weighted and summed to determine the percentage of total lung with pathology. Joint pathology was tested by examining affected joints and recording gross observations. For data analysis purposes, data was summarized. Percent reduction of clinical symptoms and gross pathology were calculated using the following formula: % Reduction=[1−(Treatment/Non-treatment)]*100. Additionally, 1 animal from each of groups 2 and 3, and 2 animals from group 4 were removed for humane reasons at Day 37.

Results

Pre-challenge clinical assessments were made from Day 1-Day 26. Loose/watery stool, depression, ear droop, and lethargy were observed during this phase of the study. Appropriate veterinary care was administered. No adverse site reactions or *Mycoplasma* specific clinical symptoms were noted from any groups on any day of observation. Post-challenge clinical assessments were made from Day 27-43. Coughing, labored respiration, depression, anorexia, swollen joints, lameness, and droopy ear were all clinical observations noted during this phase of the study. The incidence of clinical scores during the post-challenge period is summarized below in Table 3. Group 1 had two out of nine calves affected with at least one clinical sign of infection, two that were affected with respiratory signs and one that was affected with signs of joint infection. Group 3 had all calves affected with at least one clinical sign, seven calves affected with respiratory signs and three calves affected with signs of infection in their joints. Group 2 had four out of nine calves affected by at least one clinical sign, no calves affected with just respiratory signs, and four calves with signs of infection in their joints. Group 4 had seven calves with at least one clinical sign, one with respiratory signs, and seven with signs of infection in their joints.

TABLE 3

| | All (Respiratory + Joint + Other) | | | Respiratory | | | Joint | | |
|---|---|---|---|---|---|---|---|---|---|
| Group | Affected | Frequency | % Reduction | Affected | Frequency | % Reduction | Affected | Frequency | % Reduction |
| 1 Vac/Hi | 2/9 | 22% | 78% | 2/9 | 22% | 72% | 1/9 | 11% | 67% |
| 3 NoVac/Hi | 9/9 | 100% | | 7/9 | 78% | | 3/9 | 33% | |
| 2 Vac/Lo | 4/9 | 44% | 50% | 0/9 | 0% | 100% | 4/9 | 44% | 50% |
| 4 NoVac/Lo | 7/8 | 88% | | 1/8 | 13% | | 7/8 | 88% | |

Group 1 = Vaccine/High Respiratory Challenge
Group 2 = Vaccine/Low Respiratory Challenge
Group 3 = No Vaccine/High Respiratory Challenge
Group 4 = No Vaccine/Low Respiratory Challenge Lungs were collected at necropsy and observed for lesions associated with *M. bovis* infection. Animals exhibited variability in pathological features such as consolidation and nodular formation. Results of lung involvement were expressed as a percent using a scoring system reflecting the percentage of the total lung with gross pathology associated with *M. bovis* infection. In some cases, the determination of lung percent was hampered by adhesions or the atypical nature of lesions. Table 4 displays the ratios of individuals displaying any amount of lung lesions and percent range/ average percent lung involvement. For lung pathology scores, group 3 had the most calves affected (9/9) and group 2 had the least number of calves affected (2/9).

and/or surface swabs were tested by culture for the presence of *M. bovis*. The presence of gross pathological features in the joint is summarized in Table 5 below.

TABLE 5

Presence of Gross Pathologic Features in the Joint (0 = Normal; 1 = Abnormal)

| Group | Animals | Joint | Gross Swelling | Synovial Fluid Volume | Synovial Fluid appearance | Fibrin Present | Joint Capsule | Articular Surface | Detection of *M. bovis* |
|---|---|---|---|---|---|---|---|---|---|
| 1 | 5982 | Right Stifle | 1 | 1 | 1 | 1 | 1 | 1 | Yes |
| 1 | 5887 | Left Stifle | NR | 1 | 0 | 0 | 0 | 0 | No |
| 1 | 5007 | Right Stifle | NR | 1 | 0 | 0 | 0 | 0 | No |
| 1 | 0007 | Right rear fetlock | 0 | 0 | 0 | 0 | 0 | 0 | No |
| 2 | 5987 | Right Elbow | 0 | 0 | 0 | 0 | 0 | 0 | Yes |
| 2 | 5989 | Right Hock | NR | 1 | NR | 1 | 1 | 0 | Yes |
| 3 | 5995 | Right Hock | 1 | 1 | 1 | 1 | 1 | 0 | Yes |
| 3 | 5990 | Left Stifle | 0 | 1 | 1 | 0 | 0 | 0 | Yes |
| 4 | 5985 | Left rear fetlock | 1 | 1 | 1 | 0 | 1 | 0 | Yes |
| 4 | 5991 | Left rear fetlock | 1 | 0 | 1 | 0 | 1 | 0 | No |
| 4 | 0004 | Left Stifle | 1 | 1 | NR | 1 | 1 | 0 | Yes |
| 4 | 0000 | Left Carpus | 1 | 1 | 0 | 0 | 0 | 0 | Yes |
| 4 | 0011 | Right Elbow | 1 | 1 | 1 | 0 | 0 | 0 | Yes |
| 4 | 0011 | Right Stifle | 1 | 1 | 1 | 0 | 1 | 0 | Yes |
| 4 | 0013 | Left Stifle | 0 | 0 | 1 | 0 | 0 | 0 | No |
| 4 | 6015 | Right Hock | 0 | 1 | 1 | 1 | 0 | 0 | Yes |

Group 1 = Vaccine/High Respiratory Challenge;
2 = Vaccine/Low Respiratory Challenge;
3 = No Vaccine/High Respiratory Challenge;
4 = No Vaccine/Low Challenge
(NR = Not Recorded)

TABLE 4

Summary of Lung Pathology Scores

| | | Lung Pathology | | |
|---|---|---|---|---|
| Group | Affected | % Range | % AVG ± STD | % Reduction |
| 1 Vac/Hi | 6/9 | 0.8-26.7 | 4.0 ± 8.6 | 33% |
| 3 No Vac/Hi | 9/9 | 0.4-23.9 | 6.0 ± 7.4 | |
| 2 Vac/Lo | 2/9 | 0.4-2.0 | 0.3 ± 0.7 | 96% |
| 4 No Vac/Lo | 6/8 | 0.4-36.3 | 7.2 ± 12.3 | |

Figure 2:
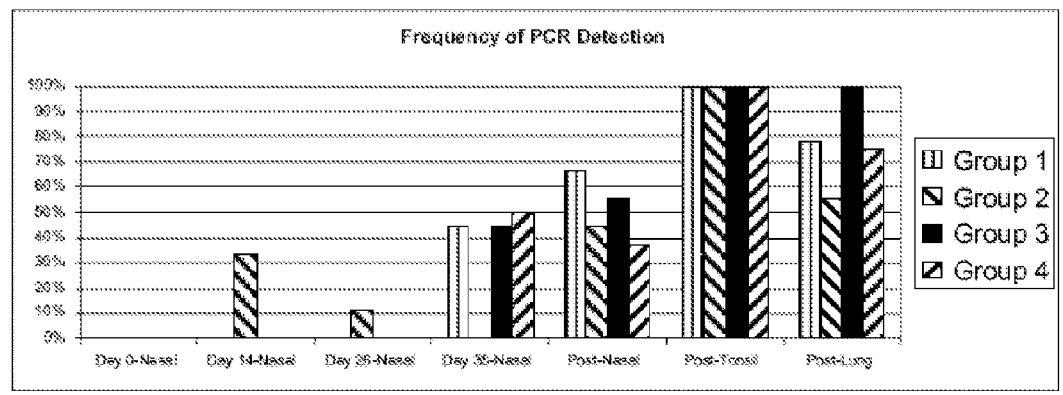
FIG. 2: Frequency of PCR Detection from Nasal, Tonsil and Lung Samples (Days 0, 14, 28, 35 and Post)

At necropsy, joints from animals that previously exhibited clinical symptoms (swelling or lameness) were examined for gross pathology. Areas affected varied by animal and may have involved the carpus, hock, stifle, fetlock and/or elbow. Animals presented with gross swelling, increased synovial fluid, abnormal fluid appearance and thickening of the joint capsule. In more severely affected calves, fibrin was present as was erosion of the articular surface. Samples of joint fluid The nasal passages were sampled by swab on Day 0, 14, 28, and 35 and then sampled at necropsy (Day 43). In addition, during the post-mortem, samples of tonsils were taken by swab and representative lung tissue was recovered. FIGS. 1 and 2 show the frequency of recovery by *Mycoplasma* selective culture or the frequency of detection by *M. bovis* specific PCR. As shown in FIG. 1, there was 100% recovery from all groups when the tonsils were sampled post necropsy. There was 100% recovery in groups 1 and 3 in the lungs post necropsy. Group 2 recovered the least amount from the lungs (about 60%) and group 4 recovered about 90%. No group showed recovery of bacteria *M. bovis* until samples taken nasally on day 35 of the study, and the only group to show recovery on day 35 was group 4 (25%). All groups except group 2 showed recovery in nasal samples post necropsy.

TABLE 6

Summary of PCR and Serology:

| | | Day 0 | | | Day 14 | | | Day 28 | | | Day 35 | | |
|---|---|---|---|---|---|---|---|---|---|---|---|---|---|
| | | Sample | | | | | | | | | | | |
| Group | Cosby ID | Nasal Culture | Nasal PCR-uvrC | Serum ELISA | Nasal Culture | Nasal PCR-uvrC | Serum ELISA | Nasal Culture | Nasal PCR-uvrC | Serum ELISA | Nasal Culture | Nasal PCR-uvrC | Serum ELISA |
| 1 | 5981 | 0 | 0 | 0 | 0 | 0 | 2 | 0 | 0 | 3 | 0 | 1 | 4 |
| 1 | 5986 | 0 | 0 | 0 | 0 | 0 | 2 | 0 | 0 | 3 | 0 | 0 | 4 |
| 1 | 5998 | 0 | 0 | 0 | 0 | 0 | 1 | 0 | 0 | 2 | 0 | 1 | 4 |
| 1 | 5999 | 0 | 0 | 0 | 0 | 0 | 3 | 0 | 0 | 3 | 0 | 0 | 4 |
| 1 | 6003 | 0 | 0 | 0 | 0 | 0 | 1 | 0 | 0 | 2 | 0 | 0 | 4 |
| 1 | 6007 | 0 | 0 | 0 | 0 | 0 | 1 | 0 | 0 | 2 | 0 | 0 | 4 |
| 1 | 6008 | 0 | 0 | 0 | 0 | 0 | 1 | 0 | 0 | 2 | 0 | 0 | 4 |
| 1 | 6009 | 0 | 0 | 0 | 0 | 0 | 2 | 0 | 0 | 3 | 0 | 1 | 4 |
| 1 | 6012 | 0 | 0 | 0 | 0 | 0 | 1 | 0 | 0 | 2 | 0 | 1 | 4 |
| 2 | 5982 | 0 | 0 | 0 | 0 | 0 | 1 | 0 | 0 | 1 | 0 | 0 | 3 |
| 2 | 5983 | 0 | 0 | 0 | 0 | 0 | 2 | 0 | 0 | 2 | 0 | 0 | 4 |
| 2 | 5984 | 0 | 0 | 0 | 0 | 0 | 1 | 0 | 0 | 2 | 0 | 0 | 4 |
| 2 | 5987 | 0 | 0 | 0 | 0 | 0 | 1 | 0 | 0 | 1 | 0 | 0 | 3 |
| 2 | 5988 | 0 | 0 | 0 | 0 | 1 | 1 | 0 | 1 | 1 | 0 | 0 | 3 |
| 2 | 5989 | 0 | 0 | 0 | 0 | 1 | 1 | 0 | 0 | 2 | 0 | 0 | 4 |
| 2 | 5990 | 0 | 0 | 0 | 0 | 1 | 2 | 0 | 0 | 2 | 0 | 0 | 4 |
| 2 | 5992 | 0 | 0 | 0 | 0 | 0 | 2 | 0 | 0 | 3 | 0 | 0 | 4 |
| 2 | 5994 | 0 | 0 | 0 | 0 | 0 | 3 | 0 | 0 | 2 | 0 | 0 | 4 |
| 3 | 5993 | 0 | 0 | 0 | 0 | 0 | 0 | 0 | 0 | 0 | 0 | 0 | 1 |
| 3 | 5995 | 0 | 0 | 0 | 0 | 0 | 0 | 0 | 0 | 1 | 0 | 1 | 1 |
| 3 | 5996 | 0 | 0 | 0 | 0 | 0 | 1 | 0 | 0 | 1 | 0 | 1 | 2 |
| 3 | 5997 | 0 | 0 | 0 | 0 | 0 | 0 | 0 | 0 | 0 | 0 | 0 | 0 |
| 3 | 6000 | 0 | 0 | 0 | 0 | 0 | 0 | 0 | 0 | 0 | 0 | 0 | 1 |
| 3 | 6001 | 0 | 0 | 0 | 0 | 0 | 1 | 0 | 0 | 1 | 0 | 0 | 1 |
| 3 | 6002 | 0 | 0 | 0 | 0 | 0 | 0 | 0 | 0 | 0 | 0 | 1 | 0 |
| 3 | 6010 | 0 | 0 | 0 | 0 | 0 | 0 | 0 | 0 | 0 | 0 | 0 | 1 |
| 3 | 6014 | 0 | 0 | 0 | 0 | 0 | 0 | 0 | 0 | 0 | 0 | 1 | 0 |
| 4 | 5985 | 0 | 0 | 0 | 0 | 0 | 0 | 0 | 0 | 0 | 0 | 1 | 0 |
| 4 | 5991 | 0 | 0 | 0 | 0 | 0 | 0 | 0 | 0 | 0 | 1 | 1 | 0 |
| 4 | 6004 | 0 | 0 | 0 | 0 | 0 | 0 | 0 | 0 | 0 | 0 | 0 | 0 |
| 4 | 6005 | 0 | 0 | 0 | 0 | 0 | 0 | 0 | 0 | 0 | 0 | 0 | 1 |
| 4 | 6006 | 0 | 0 | 0 | 0 | 0 | 1 | 0 | 0 | 1 | 1 | 1 | 1 |
| 4 | 6011 | 0 | 0 | 0 | 0 | 0 | 0 | 0 | 0 | 0 | 0 | 0 | 0 |
| 4 | 6013 | 0 | 0 | 0 | 0 | 0 | 0 | 0 | 0 | 0 | 0 | 0 | 1 |
| 4 | 6015 | 0 | 0 | 0 | 0 | 0 | 0 | 0 | 0 | 0 | 0 | 1 | 1 |

| | | Day 42 (or Post) Sample | | | | | | | | | | |
|---|---|---|---|---|---|---|---|---|---|---|---|---|
| Group | Cosby ID | Nasal Culture | Nasal PCR-uvrC | Serum ELISA | Tonsil Culture | Tonsil PCR-uvrC | Tonsil PCR-Vac specific | Lung Culture | Lung PCR-uvrC | Lung PCR-Vac specific | Joint Culture | Joint PCR-uvrC |
| 1 | 5981 | 1 | 0 | 4 | 1 | 1 | 1 | 1 | 1 | 0 | | |
| 1 | 5986 | 0 | 1 | 4 | 1 | 1 | 1 | 1 | 1 | 0 | | |
| 1 | 5998 | 0 | 1 | 3 | 1 | 1 | 1 | 1 | 1 | 0 | | |
| 1 | 5999 | 0 | 1 | 4 | 1 | 1 | 0 | 1 | 0 | 0 | | |
| 1 | 6003 | 0 | 1 | 4 | 1 | 1 | 0 | 1 | 1 | 0 | | |
| 1 | 6007 | 0 | 0 | 4 | 1 | 1 | 1 | 1 | 1 | 0 | 0 | 0 |
| 1 | 6008 | 0 | 1 | 4 | 1 | 1 | 0 | 1 | 0 | 0 | | |
| 1 | 6009 | 0 | 1 | 4 | 1 | 1 | 0 | 1 | 1 | 0 | | |
| 1 | 6012 | 0 | 0 | 4 | 1 | 1 | 0 | 1 | 1 | 0 | | |
| 2 | 5982 | 0 | 0 | 4 | 1 | 1 | 1 | 1 | 1 | 0 | 1 | 1 |
| 2 | 5983 | 0 | 0 | 4 | 1 | 1 | 1 | 1 | 1 | 0 | | |
| 2 | 5984 | 0 | 0 | 4 | 1 | 1 | 1 | 0 | 0 | 0 | | |
| 2 | 5987 | 0 | 0 | 4 | 1 | 1 | 1 | 1 | 1 | 0 | 1 | 1 |
| 2 | 5988 | 0 | 1 | 3 | 1 | 1 | 0 | 1 | 1 | 0 | | |
| 2 | 5989 | 0 | 0 | 4 | 1 | 1 | 1 | 0 | 0 | 0 | 1 | 1 |
| 2 | 5990 | 0 | 1 | 3 | 1 | 1 | 1 | 0 | 0 | 0 | | |
| 2 | 5992 | 0 | 1 | 4 | 1 | 1 | 1 | 0 | 0 | 0 | | |
| 2 | 5994 | 0 | 1 | 4 | 1 | 1 | 1 | 1 | 1 | 0 | | |
| 3 | 5993 | 0 | 0 | 1 | 1 | 1 | 0 | 1 | 1 | 0 | | |
| 3 | 5995 | 0 | 1 | 2 | 1 | 1 | 0 | 1 | 1 | 0 | 1 | NT |
| 3 | 5996 | 0 | 1 | 3 | 1 | 1 | 0 | 1 | 1 | 0 | 1 | 1 |
| 3 | 5997 | 1 | 1 | 1 | 1 | 1 | 0 | 1 | 1 | 0 | | |
| 3 | 6000 | 1 | 1 | 3 | 1 | 1 | 0 | 1 | 1 | 0 | | |
| 3 | 6001 | 0 | 0 | 3 | 1 | 1 | 0 | 1 | 1 | 0 | | |
| 3 | 6002 | 0 | 0 | 2 | 1 | 1 | 0 | 1 | 1 | 0 | | |

TABLE 6-continued

Summary of PCR and Serology:

| | | | | | | | | | | | | |
|---|---|---|---|---|---|---|---|---|---|---|---|---|
| 3 | 6010 | 0 | 1 | 3 | 1 | 1 | 0 | 1 | 1 | 0 | | |
| 3 | 6014 | 0 | 0 | 2 | 1 | 1 | 0 | 1 | 1 | 0 | | |
| 4 | 5985 | 1 | 1 | 4 | 1 | 1 | 0 | 1 | 1 | 0 | 1 | NT |
| 4 | 5991 | 1 | 1 | 2 | 1 | 1 | 0 | 1 | 1 | 0 | 0 | NT |
| 4 | 6004 | 0 | 0 | 2 | 1 | 1 | 0 | 1 | 1 | 0 | 1 | NT |
| 4 | 6005 | 0 | 0 | 3 | 1 | 1 | 0 | 1 | 0 | 0 | | |
| 4 | 6006 | 0 | 1 | 1 | 1 | 1 | 0 | 1 | 1 | 0 | 1 | 1 |
| 4 | 6011 | 0 | 0 | 1 | 1 | 1 | 0 | 0 | 0 | 0 | 1 | NT |
| 4 | 6013 | 1 | 0 | 3 | 1 | 1 | 0 | 1 | 1 | 0 | 0 | 0 |
| 4 | 6015 | 0 | 0 | 3 | 1 | 1 | 0 | 1 | 1 | 0 | 1 | 1 |

Culture
0 = No *M. bovis* growth
1 = Growth of *M. bovis*
M = Mixed/or other
PCR
0 = Negative for *M. bovis*
1 = Positive for *M. bovis*
ELISA
0 = Negative
1 = Positivity to 1.75x
2 = 1.75x to 2.3x
3 = 2.3x to 3.0x
4 = 3.0x or greater
NS = No Sample
NT = Not Tested All samples were tested in the Biovet *M. bovis* ELISA to monitor the serological response to *M. bovis*. Seroconversion was scored according to grouped multipliers of positivity ODs. The following table shows the average serological scores detected from each group on Day 0, 14, 28, 35 and 42. FIG. 3 shows the average group score for *M. bovis* specific antibodies from serum samples. Seroconversion indicating effective humoral immune response was detected at no more than 14 days following one dose of vaccine, and good duration of this immune response was evident by measurable serological response to *M. bovis* for at least 42 days after one vaccination and 28 days after two doses of vaccine. The score for group 1 was consistently higher than all other groups beginning on day 28. Groups 1 and 2 were equal on day 14 (1.5 ELISA score). Group 4 was the lowest from days 14-35, and came in third (about 2.2) on day 42.

Conclusions

This study assessed the efficacy of a live *M. bovis* vaccine in calves given as two doses, given both subcutaneously and intranasally, and challenge models in the target species. The challenge model included a high respiratory administration and a low respiratory administration. The study also evaluated efficacy, onset of immunity, and duration of immunity by an indirect assessment, seroconversion or humoral immune response following a single and two doses of vaccine. The onset of immunity and duration of immunity following vaccination was so proven.

Both the challenge and vaccine *M. bovis* isolates originated from different, naturally infected animals. The isolate used as the challenge was previously shown to cause both lung and joint disease during experimental challenge and predominated in mixed isolate challenge studies. The vaccine isolate is a high passage isolate (passage 106) originally derived from a diagnostic sample. Furthermore, the genotypes of the challenge and vaccine isolates were shown to be dissimilar when using the fingerprinting method described in WO 2008-030619.

Within the high volume respiratory challenged groups (1 and 3), a reduction in respiratory clinical symptoms (72%) and lung pathology (33%) was observed in the vaccinated group. Most of the respiratory clinical symptoms in the non-vaccinated group occurred between day 2 and 3 post challenge. As shown in Table 3, the vaccine also reduced the occurrence of joint disease due to *M. bovis*.

Within the low volume respiratory challenged groups (2 and 4), a reduction (96%) in lung pathology was observed in the vaccinated group. In addition, the vaccinated group showed an appreciable reduction (50%) of joint clinical symptoms.

Laboratory testing of lung samples (IHC, PCR and culture) and joint samples (PCR and culture) agreed with gross pathology in most instances. Discrepancies may be attributed to bacterial distribution at the sampling site or between samples submitted for testing. The vaccine isolate was not detected from any lung samples tested by an experimental PCR assay designed to detect the vaccine candidate and not the challenge isolate.

The novel, high passage attenuated Live *M. bovis* vaccine candidate (05-2823 P106) given via both intranasal and subcutaneous route administered 2 times with a 2 week interval between vaccinations was shown to be safe and effective by providing a reduction in signs of *M. bovis* infection including both clinical symptoms and pathology (respiratory and joint) associated with *Mycoplasma bovis* infection in colostrum deprived calves using various challenge conditions. The *M. bovis* vaccine and immunological composition was also effective in stimulating an onset of immunity no more than 14 days following a single dose and with a duration of at least 42 days following the single dose.

Example 2

The purpose of this investigation was to determine the safety and efficacy of three live vaccine candidates.
Materials and Methods The calves used for the study were 6±2 weeks of age and were divided into 6 groups. As shown in Table 7, group 1 was comprised of 10 animals, which were vaccinated with *M. bovis* Live Vaccine I on day 0 (D0) and D14 of the study. Group 1 was vaccinated with 2 ml subcutaneously and 2 ml intranasally on D0 and D14. Group 2 was comprised of 10 animals and was vaccinated with 2 ml of *M. bovis* Live Vaccine I subcutaneously on D0 and D14 of the study. Group 3 was comprised of 9 calves vaccinated with *M. bovis* Live Vaccine I on D0 and D14. Group 3 was vaccinated with 2 ml intranasally. Group 4 was a control and was not administered any vaccine. Group 5 was comprised of 2 calves that were vaccinated with *M. bovis* Live II vaccine. Group 5 was vaccinated with 2 ml subcutaneously and 2 ml intranasally on D0 and D14. Group 6 was comprised of two calves that were administered *M. bovis* Live Vaccine III. The calves in Group 6 were administered 2 ml subcutaneously and 2 ml intranasally on D0 and D14. All groups were subsequently challenged with 120 ml of challenge material. All animals were challenged on D28.

As noted in Table 8, nasal swabs were collected from all calves on Days 0, 14, 27, 35 and 41. At necropsy, tonsil swabs were collected from all calves. Joint swabs were taken from animals with clinical abnormalities. In addition, samples were taken from other locations in certain animals showing area involvement. Blood was collected from all calves on Days 0, 14, 27, 35 and 41. Blood was collected aseptically from a jugular vein from each calf. After necropsy, lungs were scored for lung lesions.

TABLE 7

Group Treatments

| | Animals/group | Test Substance | | | Challenge | | |
|---|---|---|---|---|---|---|---|
| | | Article | Dose/Route | Admin Schedule | Material | Dose | Admin Schedule |
| Group 1 | 10 | *M. bovis* Live I (05-2823 P106) | 2 ml SQ and 2 mL IN | Day 0 and 14 | *M. bovis* | challenge material with a 5 ml wash of PBS | Day 28 (approx 4 weeks after vaccination) |
| Group 2 | 10 | *M. bovis* Live I (05-2823 P106) | 2 ml SQ | Day 0 and 14 | *M. bovis* | challenge material with a 5 ml wash of PBS | Day 28 (approx 4 weeks after vaccination) |
| Group 3 | 9 | *M. bovis* Live I (05-2823 P106) | 2 mL IN | Day 0 and 14 | *M. bovis* | challenge material with a 5 ml wash of PBS | Day 28 (approx 4 weeks after vaccination) |
| Group 4 | 9 | Media Only | 2 ml SQ and 2 mL IN | Day 0 and 14 | *M. bovis* | challenge material with a 5 ml wash of PBS | Day 28 (approx 4 weeks after vaccination) |
| Group 5 | 2 | M. bovis Live II (05-249 P102) | 2 ml SQ and 2 mL IN | Day 0 and 14 | *M. bovis* | challenge material with a 5 ml wash of PBS | Day 28 (approx 4 weeks after vaccination) |
| Group 6 | 2 | *M. bovis* Live III (05-1902-1 P106) | 2 ml SQ and 2 mL IN | Day 0 and 14 | *M. bovis* | challenge material with a 5 ml wash of PBS | Day 28 (approx 4 weeks after vaccination) |

TABLE 8

Sample Schedule

| Day | Event | Samples | Testing |
|---|---|---|---|
| −42 to 0 | General Observations (Daily) | — | — |
| Approx −35 | Collect samples | Nasal swab (Wet/Dry) Blood (SST) Ear-notch | *M. bovis* (Culture/PCR) *M. bovis* (ELISA) BVDV (IHC) |
| 0 to 28 | Clinical assessment | — | — |
| 0 | Collect samples | Nasal swab (Wet/Dry) Blood (SST) | *M. bovis* (Culture/PCR) *M. bovis* (ELISA) |
| | 1st Vaccination | — | — |
| 14 | Injection site evaluation. Collect samples | Nasal swab (Wet/Dry) Blood (SST) | *M. bovis* (Culture/PCR) *M. bovis* (ELISA) |
| | 2nd Vaccination | — | — |
| 27 | Collect samples | Nasal swab (Wet/Dry) Blood (SST) | *M. bovis* (Culture/PCR) *M. bovis* (ELISA) |
| 28 | Challenge | — | — |
| 29 to 42 | Clinical observation (Daily) | — | — |
| 35 | Collect samples | Nasal swab (Wet/Dry) Blood (SST) | *M. bovis* (Culture/PCR) *M. bovis* (ELISA) |
| 41 | Collect samples | Nasal swab (Wet/Dry) Blood (SST) | *M. bovis* (Culture/PCR) *M. bovis* (ELISA) |
| 42 | Necropsy and Gross Pathology Collect samples (Post) | Tonsil swab (Wet/Dry) Lung Tissue | *M. bovis* (Culture/PCR) *M. bovis* (IHC) |

TABLE 8-continued

Sample Schedule

| Day | Event | Samples | Testing |
|---|---|---|---|
| | | (Preserved) | |
| | | Lung Tissue (Fresh) | *M. bovis* (Culture/PCR) |
| | | Joint swabs (Wet/Dry) | *M. bovis* (Culture/PCR) |

Results and Discussion

Pre-Challenge Clinical Signs

Clinical assessments were made from Day −1 through Day 28. Loose/watery stool, ocular discharge, depression and lethargy were clinical observations noted during this phase of the study, and none were attributed to an effect of vaccination. Observation of injection sites recorded no adverse site reactions except for calf 6134 (group 6) that showed acceptable transient swelling at the 1st injection site on Day 14.

Post-Challenge Clinical Signs

Clinical observations were made from Day 28 through Day 42. Coughing, labored respiration, depression, swollen joints, lameness and droopy ear were clinical observations noted during this phase of the study. Clinical signs were divided into three types (respiratory, joint and other) typical of *Mycoplasma bovis* infection. Respiratory signs included coughing, rapid/labored respiration and nasal discharge. Joint signs included swollen joints and lameness. Other signs included ear droop, head tilt, depression and anorexia. Table 9 displaying individual results can be found below:

TABLE 9

| | DPC | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| Group | ID | 28 | 29 | 30 | 31 | 32 | 33 | 34 | 35 | 36 | 37 | 38 | 39 | 40 | 41 | 42 |
| 1 | 6116 | | | | | | 5 | 4, 5 | 4, 5 | 4, 5 | 4, 5 | | | | | |
| 1 | 6123 | | | | | | | | 4, 7 | 4 | 4, 5 | 4, 5, 8 | | | | |
| 1 | 6124 | | | | | | | | | | 4, 5 | 1, 4, 5 | 4, 5, 8 | 4, 5 | 4, 5 | 4, 5 |
| 1 | 6139 | | | | | | | | | 4, 5 | 1, 4, 5 | 4, 5 | 4, 5 | 4, 5 | 1, 4, 5 8 | 4, 5 |
| 1 | 6140 | | | | | | | | 4, 5 | 4, 5 | 4, 5 | 4, 5 | 4, 5 | 4, 5 | 4, 5 | 4, 5 |
| 1 | 6145 | | | | | | 5 | 4, 5 | 4, 5 | 4, 5 | 4, 5 | | | | | |
| 1 | 6151 | | | | | 5 | 4, 5 | 4, 5 | 4, 5 | 4, 5 | 4, 5 | 4, 5, 8 | | | | |
| 1 | 6152 | | | | | | | 4 | 4, 5 | 4, 5 | 4, 5 | 4, 5 | 4, 5 | 4, 5 | 4, 5 | 4, 5 |
| 1 | 6153 | | | | | | | | | | | | | | | |
| 1 | 6156 | | | | | | 1 | | | 4 | | 4, 5 | 4, 5 | 4, 5 | | |
| 2 | 6117 | | | | | | | 4 | 4, 5 | 4, 5, 8 | 4, 5 | | | | | |
| 2 | 6118 | | 2 | | | | | | | | | | | | | |
| 2 | 6119 | | | | | | | | | | 4 | | | 4, 5 | 4, 5 | |
| 2 | 6125 | | | | | 5 | 5, 8 | 4, 5, 6, 8 | 4, 5 | 4, 5 | 4, 5 | 4, 5, 8 | | | | |
| 2 | 6127 | | | | | 5 | 5 | 4, 5 | 4, 5 | 4, 5 | 4, 5 | | | | | |
| 2 | 6128 | | | | | | 5 | 4, 5 | 4, 5 | 4, 5 | 4, 5 | | | | | |
| 2 | 6130 | | | | | | | | | | | 4, 5 | 4, 5 | 4, 5 | 4, 5 | 4, 5 |
| 2 | 6133 | | | | | | | 4, 5 | 4, 5 | 4, 5 | 4, 5 | 4, 5 | 4, 5 | 4, 5 | 4, 5, 8 | 4, 5 |
| 2 | 6136 | | | | | | 4 | 4, 5 | 4, 5 | 4, 5 | 4, 5 | 4, 5 | 4, 5 | 4, 5 | 4, 5 | 4, 5 |

TABLE 9-continued

| Group | Animal | | | | | | | | | | | | |
|---|---|---|---|---|---|---|---|---|---|---|---|---|---|
| 3 | 6129 | | | | 5 | 5 | 4, 5 | 4, 5 | 4, 5 | 4, 5 | 4, 5 | ■ | ■ |
| 3 | 6132 | | | | | 5 | 4, 5 | 4, 5 | 4, 5 | 4, 5 | ■ | ■ | ■ |
| 3 | 6135 | | | | | 5 | 4, 5 | 4, 5 | 4, 5 | 4, 5 | ■ | ■ | ■ |
| 3 | 6138 | | | | | | | | | | | | |
| 3 | 6141 | | | | | | 4, 5 | 4, 5 | | 4, 5 | 4, 5 | 4, 5 | 4, 5 | 4, 5 |
| 3 | 6142 | | | | | | | 4, 5 | 4 | 4, 5 | 4, 5 | 4, 5 | 4, 5, 8 | 4, 5, 8 |
| 3 | 6154 | | | | | | | 4, 5 | 4, 5 | 4, 5 | 4, 5 | 4, 5 | 4, 5 | 4, 5 |
| 3 | 6158 | | | | | | | | | | | 4, 5 | 4, 5 | 4, 5 |
| 3 | 6159 | | | | | | 4, 5 | 4, 5, 8 | 4, 5 | ■ | ■ | ■ | ■ |
| 4 | 6120 | | | | 5 | | 4, 5 | 4, 5 | 4, 5, 8 | 4, 5, 8 | ■ | ■ | ■ |
| 4 | 6126 | | | | 5 | 5 | 4, 5 | 4, 5 | 4, 5, 8 | 4, 5, 8 | ■ | ■ | ■ |
| 4 | 6131 | | | | | | 8 | 4 | 4, 5, 8 | 4, 5, 8 | ■ | ■ | ■ |
| 4 | 6143 | | | | 5 | 1, 5 | 4, 5 | 4, 5 | 4, 5, 8 | 4, 5, 8 | ■ | ■ | ■ |
| 4 | 6146 | | | | 2, 5, 8 | 2, 4, 5, 8 | ■ | ■ | ■ | ■ | ■ | ■ | ■ |
| 4 | 6147 | | | | | | 4, 5 | 4, 5 | 4, 5, 8 | 4, 5, 8 | ■ | ■ | ■ |
| 4 | 6150 | | | | 1 | 1 | 4, 5 | 4, 5 | 1, 4, 5 | 4, 5, 8 | ■ | ■ | ■ |
| 4 | 6155 | | | 5 | 5 | 4, 5, 8 | ■ | ■ | ■ | ■ | ■ | ■ | ■ |
| 4 | 6157 | 1, 2 | 2 | 2 | 2, 8 | 1, 2, 8 | ■ | ■ | ■ | ■ | ■ | ■ | ■ |
| 5 | 6122 | | | | | | | | | | | | |
| 4 | 6137 | | | | | | | | | | | ■ | ■ | |
| 5 | 6121 | | | | | | | | | | | | |
| 5 | 6134 | | | | | | | | | | | | |

Key to Clinical Sign:
1 Coughing
2 Rapid (labored) respiration
3 Nasal discharge
4 Swollen Joint
5 Lame
6 Ear Droop
7 Head Tilt
8 Depression
9 Anorexia
A Diarrhea
B Ocular Discharge
C Leg Laceration
Black Box = Animal removed from study

TABLE 10

Incidence of Clinical Scores during the Post-Challenge period

| | | Respiratory | | | Joint | | | Early Removal | | |
|---|---|---|---|---|---|---|---|---|---|---|
| | Group | Affected | Frequency | % Reduction | Affected | Frequency | % Reduction | Affected | Frequency | % Reduction |
| 1 | Live Vac I (SQ + IN) | 3/9 | 33% | 0% | 6/9 | 67% | 33% | 4/9 | 44% | 56% |
| 2 | Live Vac I (SQ) | 0/9 | 0% | 100% | 7/9 | 78% | 22% | 4/9 | 44% | 56% |
| 3 | Live Vac I (IN) | 0/9 | 0% | 100% | 5/8 | 63% | 38% | 3/8 | 38% | 63% |

TABLE 10-continued

Incidence of Clinical Scores during the Post-Challenge period

| | | Respiratory | | | Joint | | | Early Removal | |
|---|---|---|---|---|---|---|---|---|---|
| Group | Affected | Frequency | % Reduction | Affected | Frequency | % Reduction | Affected | Frequency | % Reduction |
| 5 Live Vac II (SQ + IN) | 0/2 | 0% | 100% | 0/2 | 0% | 100% | 0/2 | 0% | 100% |
| 6 Live Vac III (SQ + IN) | 0/2 | 0% | 100% | 0/2 | 0% | 100% | 0/2 | 0% | 100% |
| 4 No Vac | 2/6 | 33% | | 6/6 | 100% | | 6/6 | 100% | |

The table 10 is subdivided into respiratory and confirmed (culture and/or PCR) joint clinicals typical of *Mycoplasma bovis* infection. In addition, early removal rates due to severe joint involvement are reported.

Lung Pathology

At necropsy, lungs were collected and observed for lesions associated with *M. bovis*. Animals exhibited variability in pathological features such as consolidation and nodular formation. Results of lung involvement were expressed as a percent using a scoring system that reflects the percentage of the total lung with gross pathology associated with *Mycoplasma bovis* infection. In some cases, determination of lung percent was hampered by adhesions or the atypical nature of lesions. Below is a table with the ratios of individuals displaying any amount of lung lesions and percent range/mean percent lung involvement.

TABLE 11

Summary of Lung Pathology Scores

| | | | Lung Pathology | | |
|---|---|---|---|---|---|
| | Group | Affected | % Range | Mean % Lesion + STD | % Lesion Reduction |
| 1 | Live Vac I (SQ + IN) | 7/9 | 0.2-2.0 | 1.0 ± 0.9 | 86% |
| 2 | Live Vac I (SQ) | 9/9 | 0.4-12.5 | 2.8 ± 3.8 | 61% |
| 3 | Live Vac I (IN) | 5/8 | 0.2-39.2 | 6.3 ± 13.5 | 13% |
| 5 | Live Vac II (SQ + IN) | 1/2 | N/A | 0.2 ± 0.3 | 98% |
| 6 | Live Vac III (SQ + IN) | 0/2 | N/A | 0.0 | 100% |
| 4 | No Vac | 6/6 | 2.0-19.5 | 7.2 ± 6.9 | |

Joint Pathology

At necropsy, joints from animals that previously exhibited clinical symptoms (swelling and/or lameness) were examined for gross pathology. Areas affected varied by animal and may involve the carpus, hock, stifle, fetlock and/or elbow. Animals presented with gross swelling, increased synovial fluid, abnormal fluid appearance or thickening of the joint capsule. In more severely affected calves, fibrin was present and erosion of the articular surface. Samples of joint fluid and/or surface swabs were tested by culture and PCR for the presence of *Mycoplasma bovis*. Vaccination using any of the attenuated live vaccines successfully reduced the total numbers of calves affected.

TABLE 12

Incidence of Laboratory Confirmed Clinical Joints

| | Total | Right Front | | | | Left Front | | | | Right Rear | | | | Left Rear | | | |
|---|---|---|---|---|---|---|---|---|---|---|---|---|---|---|---|---|---|
| Group | Animals Affected | Fetlock | Knee | Elbow | Shoulder | Fetlock | Knee | Elbow | Shoulder | Fetlock | Hock | Stifle | Hip | Fetlock | Hock | Stifle | Hip |
| 1 | 6/9 | 0% | 44% | 11% | 0% | 11% | 22% | 0% | 0% | 11% | 11% | 11% | 0% | 33% | 11% | 22% | 0% |
| 2 | 7/9 | 29% | 29% | 0% | 0% | 29% | 86% | 0% | 0% | 29% | 29% | 14% | 14% | 57% | 14% | 14% | 0% |
| 3 | 5/8 | 0% | 38% | 0% | 0% | 0% | 13% | 0% | 0% | 13% | 0% | 13% | 0% | 13% | 13% | 25% | 0% |
| 4 | 6/6 | 50% | 83% | 33% | 0% | 50% | 100% | 0% | 0% | 67% | 17% | 0% | 0% | 83% | 0% | 0% | 0% |
| 5 | 0/2 | 0% | 0% | 0% | 0% | 0% | 0% | 0% | 0% | 0% | 0% | 0% | 0% | 0% | 0% | 0% | 0% |
| 6 | 0/2 | 0% | 0% | 0% | 0% | 0% | 0% | 0% | 0% | 0% | 0% | 0% | 0% | 0% | 0% | 0% | 0% |

Group 1 = Vac I (SQ + IN);
2 = Vac I (SQ only);
3 = Vac I (IN only);
4 = No Vac;
5 = Vac II (SQ + IN);
6 = Vac III (SQ + IN)

Note:
A sample was reported as laboratory confirmed if PCR and/or Culture was positive for *M. bovis*.

PCR Detection of *M. bovis* from Nasal, Tonsil and Lung Samples

The nasal passages were sampled from each animal by swab on Day 0, 14, 27, 35 and 41 or Day of Necropsy. In addition, during the post-mortem, samples of tonsils were taken by swab and representative lung tissue was recovered. The following tables show the frequency of detection using real-time PCR targeting a general *M. bovis* marker (uvrC). In addition, tonsil and lung tissue were analyzed using a recently developed end-point PCR assay targeting markers not found in the *M. bovis* challenge isolate but found in all vaccine candidates. As expected, PCR detected the *M. bovis* vaccine and/or the challenge microorganism in various nasal swab samples.

TABLE 13

PCR Detection Frequency of *M. bovis* from Nasal Swab Samples

| | | | Day of Test | | | |
|---|---|---|---|---|---|---|
| Group | n = | D0 | D14 | D27 | D35 | Post |
| 1 Live Vac I (SQ + IN) | 9 | 0% | 33% | 0% | 11% | 22% |
| 2 Live Vac I (SQ) | 9 | 0% | 0% | 0% | 22% | 0% |
| 3 Live Vac I (IN) | 8 | 0% | 0% | 13% | 0% | 25% |
| 4 No Vac | 6 | 0% | 0% | 0% | 50% | 33% |
| 5 Live Vac II (SQ + IN) | 2 | 0% | 0% | 0% | 50% | 50% |
| 6 Live Vac III (SQ + IN) | 2 | 0% | 0% | 0% | 0% | 100% |

Group 1 = Vac I (SQ + IN);
2 = Vac I (SQ only);
3 = Vac I (IN only);
4 = No Vac;
5 = Vac II (SQ + IN);
6 = Vac III (SQ + IN)
Note:
PCR detection by real-time PCR targeting a general *M. bovis* marker (uvrC).

TABLE 14

PCR Detection Frequency (General *M. bovis* and Non-Challenge assay) from Tonsil and Lung Tissue Samples

| | | Tonsil | | Lung | |
|---|---|---|---|---|---|
| Group | n = | General | Non-Challenge | General | Non-Challenge |
| 1 Live Vac I (SQ + IN) | 9 | 100% | 100% | 67% | 11% |
| 2 Live Vac I (SQ) | 9 | 100% | 0% | 100% | 0% |
| 3 Live Vac I (IN) | 8 | 100% | 100% | 13% | 0% |
| 4 No Vac | 5 | 100% | 0% | 100% | 0% |
| 5 Live Vac II (SQ + IN) | 2 | 100% | 100% | 50% | 0% |
| 6 Live Vac III (SQ + IN) | 2 | 100% | 100% | 50% | 0% |

Group 1 = Vac I (SQ + IN);
2 = Vac I (SQ only);
3 = Vac I (IN only);
4 = No Vac;
5 = Vac II (SQ + IN);
6 = Vac III (SQ + IN)
Note:
General = PCR detection by real-time PCR targeting a general *M. bovis* marker (uvrC);
Non-challenge = PCR detection by end-point PCR targeting markers not found in the *M. bovis* challenge isolate but found in all vaccine candidates.

Again, as expected PCR successfully detected the attenuated live vaccine in tonsil following intranasal vaccination, whereas the challenge microorganism was detected in a high percentage of both lung and tonsil samples.

*M. bovis* Serology

All samples were tested in the Biovet *M. bovis* ELISA to monitor the serological response to *M. bovis*. Seroconversion was scored according to grouped multipliers of positivity ODs. The following tables show the mean serological scores detected from each group on Day 0, 14, 27, 35 and Post (post represents a range of study days from 37 to 41 due to early removal of certain animals). The seroconversion seen following vaccination reinforces the conclusion that these new vaccines do provoke a suitable immune response in vaccinated animals such as calves with rapid onset and long duration (see FIG. 4).

Discussion

The objective of this study was to assess the efficacy of three novel and experimental live *Mycoplasma bovis* vaccines including vaccine (05-2823 P106) (PTA-8694) using various 2 mL administration routes (SQ, IN, SQ+IN) fourteen days apart and a dual challenge model in the target species. The challenge model used administration via the respiratory tract with the addition of a parenteral administration. In addition, two other live vaccine candidates (05-249 P102 (PTA-8696) and 05-1902-1 P106 (PTA-8695)) were evaluated for efficacy using only the SQ+IN route.

The challenge and vaccine candidate *Mycoplasma bovis* isolates originated from different naturally infected farms. The procedure using a total volume of 120 mL of the challenge isolate was previously shown when administered to cause both lung pathology and joint disease during experimental challenge and predominated in mixed isolate challenge studies. The live vaccine candidates are high passage isolates originally derived from diagnostic samples. High passage of the vaccine candidates was performed by serial limiting dilution involvement in *Mycoplasma* appropriate media. It is noted that high passage vaccine candidate 05 2823 P106 has demonstrated restricted growth on some *Mycoplasma* selective agar formulations, while the low passage parent isolate has not shown the same characteristic. Additionally, the genotypes of the challenge and vaccine isolates were (as determined by the fingerprinting method) shown to be different.

Multiple parameters were investigated during this study to assess vaccine benefits. Of those parameters, animal removal rates and joint clinical symptoms were used as primary indicators of joint protection. Lung pathology (percent gross lung lesions) was used as the primary indicator of lung protection. Other data such as detection of organism from tissue, joint distribution, and serology provided additional data for confirmation, as did seroconversion to *M. bovis* following vaccination.

Figure 5:
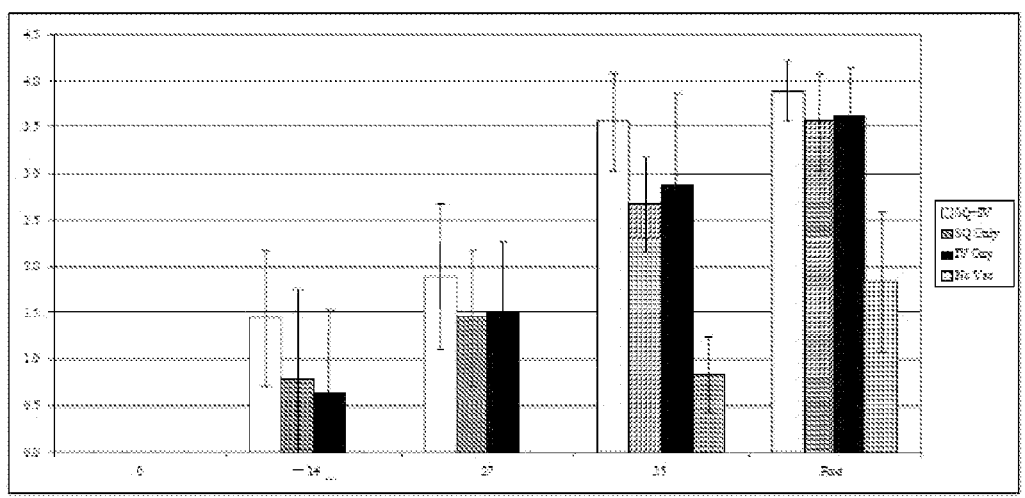
FIG. 5: Comparison of Serology for Live Vac I using Various Routes of Administration

All groups showed disease reducing lung and joint protective benefits after receiving the vaccine candidate *Mycoplasma bovis* Live Vaccine I (05-2823 P106) regardless of route or route combination as demonstrated by a reduction in lung lesions, joint clinical symptoms and animal removal rates. The combined SQ and IN route (Group 1) resulted in the greatest reduction of lung lesions (86%) compared to the groups using only a single route. Additionally, results of lung lesions, joint clinical symptoms and removal rate reductions confirm benefit from receiving the two other vaccine candidates Live Vaccine II (05-249 P102) and Live Vaccine III (05-1902-1 P106) by a combined SQ and IN route. ELISA results demonstrated a strong humoral response to vaccination with all vaccine candidates confirming that the onset of immunity following a single vaccination is as soon as 14 days and that the duration of immunity is at least 41 days (see FIG. 5).

All vaccine candidates demonstrated safety. No animals from any group receiving a vaccine presented with clinical symptoms during the vaccination period and only one animal that had received Live Vaccine III (05-1902-1 P106) showed reactivity at an injection site and that reactivity was insignificant. Additionally, results of PCR showed non-challenge *M. bovis* detection from the tonsil tissue of only groups receiving a vaccine candidate via the IN route and detection of non-challenge from lung tissue in only a single animal that had received Live Vaccine I (05-2823 P106) by both IN and SQ routes.

The data support the conclusion that, in general, novel, attenuated live *M. bovis* vaccines made in accordance with the present invention and given by various routes of administration are safe and effective, rapid in onset and long lasting in protection as immunological compositions for vaccination of calves to prevent and reduce various disease manifestations caused by infection with virulent wild type *M. bovis*.

Example 3

This example describes the DNA fingerprinting process used to differentiate *M. bovis* strains by isolating, amplifying and detecting DNA.

Materials and Methods

*Mycoplasma* sp. isolates were used in the studies. Isolates were obtained from in-house sources or field isolates obtained from infected animals. Isolates were grown using a combination of *Mycoplasma*-selective agar and broth for 1-7 days. To isolate DNA, broth cultures were spun and pelleted. DNA from the pellet was then extracted (using the Qiagen DNeasy Tissue Kit and resuspended in molecular grade water). Genomic DNA was quantitated using Picogreen (Invitrogen). Primers were designed based on the known insertion sequences (transposable elements) present in the bacterial genome (*Mycoplasma bovis*). Outwardly facing primers were manually selected from the element ends (excluding the terminal repeat regions) at a Tm of 55-58 C. PCR reactions were then carried out using a multiplex PCR master mix (Qiagen Multiplex PCR Kit). The reactions contained 1× Master mix, 300 nM of each primer and 1 ng of template DNA. Thermal cycling conditions were 95 C for 15 minutes, 35 cycles of 94 C for 30 seconds, 56.1 C for 90 seconds, 72 C for 2 minutes, with a final extension of 72 C for 4 minutes and a 4 C hold. The amplified products were separated on a 4% agarose gel with ethidium bromide (Invitrogen E-gel), run for 50 minutes at room temperature and imaged under UV light.

Results and Discussion

The results showed that each of the isolates used in this application had a unique fingerprint. However, as shown in Example 2, each isolate was also an effective attenuated live culture vaccine that was effective at providing cross protection against a challenge isolate having a different fingerprint than any of the vaccine candidates. Three field isolates, 05-2823 P106 (PTA-8694), 05-249 P102 (PTA-8696), and 05-1902-1-P106 (PTA-8695), were grown and DNA isolated according to the above protocol. 2-5 ng of DNA from each isolate was amplified according to the above protocol using a multiplex of 4 sets of IS primers identified as SEQ ID Nos 1-8 in WO 2008-030619. The amplified products were separated on a Invitrogen E-gel 4% agarose gel containing ethidium bromide (according to manufacturer) for 50 minutes and visualized under UV light. All isolates produced unique patterns. The patterns were reproducible using independent aliquots under the sample PCR reaction conditions.

Example 4

This examples describes the preparation of combination vaccines according to the invention in an exemplarily manner.

Vaccine A

*M. bovis*, IBR, and BVDV Types 1 and 2

Attenuated live BVDV type 1 and 2 strains, having at least one mutation in the coding sequence for glycoprotein $E^{rns}$ and/or at least another mutation in the coding sequence for $N^{pro}$, wherein said mutation in the coding sequence for glycoprotein $E^{rns}$ leads to inactivation of RNase activity residing in $E^{rns}$ and/or said mutation in the coding sequence for $N^{pro}$ leads to inactivation of said $N^{pro}$ (as described in WO2005/111201), are grown in MDBK-cells until a $TCID_{50}$ of about $10^{5.0}$ to $10^{8.1}$ per ml cell culture fluid. A live attenuated strain of IBR is grown in MDBK cells until a $TCID_{50}$ of about $10^{5.0}$ to $10^{8.6}$ per ml cell culture fluid. A live attenuated strain of *M. bovis* as provided herewith, preferably as deposited with the ATCC under accession numbers PTA-8694, PTA-8695, or PTA-8696 is grown in MDBK cells until a CFU of about $10^{10}$ per ml cell culture fluid. Each culture fluids are collected. Equal amounts of the antigens are mixed and lyophilized by standard techniques. For reconstitution, an aqueous solution is used. One dose of the combination vaccine contains 2 ml of the reconstituted antigens. A final dose includes IBR ($10^{5.0}$ to $10^{8.6}$ $TCID_{50}$), BVDV-1 ($10^{5.0}$ to $10^{8.1}$ $TCID_{50}$), BVDV-2 ($10^{5.0}$ to $10^{8.1}$ $TCID_{50}$), and *M. bovis* ($2.1 \times 10^9$ CFU).

Vaccine B

*M. bovis*, IBR, BVDV Types 1 and 2, and PI3

The preparation of the IBR, BVDV 1 and 2 and *M. bovis* antigens is performed as described for vaccine A. In addition, a live attenuated strain of PI3 is grown in MDBK cells until a $TCID_{50}$ of about $10^{4.2}$ to $10^{6.5}$ per ml cell culture fluid. Afterwards, the PI3 containing culture fluid is harvested. An amount of $10^{4.2}$ to $10^{6.5}$ ($TCID_{50}$) of the PI3 antigen is mixed with the IBR, and BVDV types 1 and 2. The mixture is then lyophilized by standard techniques, so that one dose of the reconstituted combination vaccine contains 2 ml as described for Vaccine A. A final dose includes IBR ($10^{5.0}$ to $10^{8.6}$ $TCID_{50}$), BVDV-1 ($10^{5.0}$ to $10^{8.1}$ $TCID_{50}$), BVDV-2 ($10^{5.0}$ to $10^{8.1}$ $TCID_{50}$), *M. bovis* ($2.1 \times 10^9$ CFU), and PI3 ($10^{4.2}$ to $10^{6.5}$ $TCID_{50}$).

Vaccine C

*M. bovis*, BVDV Types 1 and 2, PI3, *Mannheimia* (*Pasteurella*) *haemolytica*

BVDV 1 and 2, *M. bovis* bacterium, and PI3 viruses are grown as described for vaccines A and B. After the culture fluids are harvested, the antigens are lyophilized. Mannheimia (Pasteurella) haemolytica is grown until the titer reaches $10^{8.0}$ to $10^{11}$ cells per ml of culture. The bacteria are inactivated and the culture fluid is lyophilized or freeze dried, or formulated as a liquid that will not inactivate attenuated cultures of BVD, *M. bovis*, and PI3. An amount of $10^{8.0}$ to $10^{11.0}$ lyophilized or freeze dried or formulated liquid bacteria cells are mixed with the lyophilized BVDV types 1 and 2 antigen (each in an amount of $10^{5.0}$ to $10^{8.1}$ $TCID_{50}$), PI3 antigen ($10^{7.3}$ to $10^{8.3}$ $TCID_{50}$) and *M. bovis* antigen ($2.1 \times 10^9$ CFU). Final antigen amounts per dose are BVDV-1 ($10^{5.0}$ to $10^{8.1}$ TCID$_{50}$), BVDV-2 ($10^{5.0}$ to $10^{8.1}$ TCID$_{50}$), PI3 ($10^{7.3}$ to $10^{8.3}$ TCID$_{50}$) *M. bovis* (2.1×$10^9$ CFU), and Mannheimia (Pasteurella) haemolytica ($10^{8.0}$ to $10^{11.0}$ cells).

Vaccine D

*M. bovis* BVDV Types 1 and 2, IBR, PI3, *Leptospira canicola, Leptospira grippotyphosa, Leptospira hardjo, Leptospira pomoma, Leptospira borgpetersenii hardjo-bovis*

BVDV 1 and 2, *M. bovis*, IBR, and PI3 are grown as described for vaccines A and B. After the culture fluids are harvested, the viruses and *M. bovis* are lyophilized. *Leptospira canicola, Leptospira grippotyphosa, Leptospira hardjo, Leptospira pomoma, Leptospira borgpetersenii hardjo-bovis* are separately cultivated until reaching $10^{8.0}$ to $10^{11.0}$ cells per ml of culture. The *Leptospira* cultures are inactivated and the culture fluids are lyophilized or freeze dried, or formulated as a liquid that is non-virucidal for the live antigens of the vaccine. Each of the $10^{8.0}$ to $10^{11.0}$ of the lyophilised or freeze dried bacteria cells are reconstituted with the lyophilized modified BVDV types 1 and 2 (each in an amount of $10^{5.0}$ to $10^{7.0}$ TCID$_{50}$), modified live PI3 ($10^{7.3}$ to $10^{8.3}$ TCID$_{50}$), modified live *M. bovis* (2.1×$10^9$ CFU) and modified live IBR ($10^{6.1}$ to $10^{7.7}$ TCID$_{50}$) using sterile water for injection, or the lyophilized components are reconstituted using the liquid non-virucidal formulation of the *Leptospira* cultures. The reconstituted suspension (2 ml per dose) contains traces of neomycin as preservative. Final antigen amounts per dose are BVDV-1 ($10^{5.0}$ to $10^{7.0}$ TCID$_{50}$), BVDV-2 ($10^{5.0}$ to $10^{7.0}$ TCID$_{50}$), PI3 ($10^{7.3}$ to $10^{8.3}$ TCID$_{50}$) *M. bovis* (2.1×$10^9$ CFU), PI3 ($10^{7.3}$ to $10^{8.3}$ TCID$_{50}$), and *Leptospira canicola, Leptospira grippotyphosa, Leptospira hardjo, Leptospira pomoma*, and *Leptospira borgpetersenii hardjo-bovis* (each $10^{8.0}$ to $10^{11.0}$ cells).

Vaccine E

*M. bovis*, BVDV Types 1 and 2, IBR, PI3, and *H. somnus*

BVDV 1 and 2, *M. bovis*, IBR, and PI3 are grown as described for vaccines A and B. After the culture fluids are harvested, the viruses and *M. bovis* are lyophilized. *H. somnus* is cultivated until achieving $10^{7.1}$ to $10^{9.2}$ cells per ml culture. The bacteria culture is inactivated and the culture fluid is lyophilized or freeze dried, or formulated as a liquid that is non-virucidal for the live antigens of the vaccine. $10^{7.1}$ to $10^{9.2}$ of the lyophilized or freeze dried bacteria are reconstituted with the lyophilized modified BVDV types 1 and 2 (each in an amount of $10^{5.0}$ to $10^{7.0}$ TCID$_{50}$), modified live PI3 ($10^{7.3}$ to $10^{8.3}$ TCID$_{50}$), modified live *M. bovis* (2.1×$10^9$ CFU), and modified live IBR ($10^{6.1}$ to $10^{7.7}$ TCID$_{50}$) using sterile water for injection, or the lyophilized components are reconstituted using the liquid non-virucidal formulation of the bacterial *H. somnus* culture. The reconstituted suspension (2 ml per dose) contains traces of neomycin as preservative. Final antigen amounts per dose are BVDV-1 ($10^{5.0}$ to $10^{7.0}$ TCID$_{50}$), BVDV-2 ($10^{5.0}$ to $10^{7.0}$ TCID$_{50}$), PI3 ($10^{7.3}$ to $10^{8.3}$ TCID$_{50}$) *M. bovis* (2.1×$10^9$ CFU), PI3 ($10^{7.3}$ to $10^{8.3}$ TCID$_{50}$), and *H. somnus* ($10^{7.1}$ to $10^{9.2}$ cells).

Vaccine F

*M. bovis*, IBR, BVDV Types 1 and 2, PI3 and BRSV

The preparation of the IBR, PI3, BVDV 1 and 2 and *M. bovis* antigens is performed as described for vaccine A and B. In addition, a live attenuated strain of BRSV is grown in MDBK cells until a TCID$_{50}$ of about $10^{5.0}$ to $10^{7.2}$ per ml cell culture fluid. Afterwards, the BRSV containing culture fluid is harvested. After the culture fluids are harvested, the antigens are mixed and lyophilized as described for vaccine A and B. An amount of $10^{5.0}$ to $10^{7.2}$ of the BRSV antigen is mixed with the IBR, BVDV types 1 and 2, and *M. bovis* antigens. The mixture is then reconstituted in 2 ml dose volume as described for Vaccine A. For reconstitution, an aqueous solution is used. One dose of the combination vaccine contains 2 ml of the reconstituted antigens. A final dose includes IBR ($10^{5.0}$ to $10^{8.6}$ TCID$_{50}$), BVDV-1 ($10^{5.0}$ to $10^{8.1}$ TCID$_{50}$), BVDV-2 ($10^{5.0}$ to $10^{8.1}$ TCID$_{50}$), *M. bovis* (2.1×$10^9$ CFU), PI3 ($10^{4.2}$ to $10^{6.5}$ TCID$_{50}$) and BRSV ($10^{5.0}$ to $10^{7.2}$ TCID$_{50}$).

The invention claimed is:

1. An immunogenic composition for the treatment of cattle against microbiological infections, wherein said immunogenic composition comprises:
   a) one or more attenuated avirulent *Mycoplasma bovis* (*M. bovis*) antigens, wherein *M. bovis* bacterium is passaged more than 100 times, wherein the *M. bovis* bacterium is selected from the group consisting of: the attenuated *M. bovis* bacteria strains deposited with the ATCC under accession numbers PTA-8694, PTA-8695, or PTA-8696; and b) one or more further immunologically active component(s) effective for the treatment of microbiological infection in cattle caused by a cattle pathogen other than *M. bovis*.

2. The immunogenic composition according to claim 1, wherein said microbiological infection in cattle caused by a cattle pathogen other than *M. bovis* is caused by one or more pathogens selected from the group consisting of:

Bovine viral diarrhea virus (BVDV), Parainfluenza-3 Virus (PI-3), Infectious Bovine Rhinotracheitis virus (IBR), Bovine Respiratory Syncytial Virus (BRSV), Bovine Herpesvirus (BHV), Bovine Rotavirus (BRV), Bovine Enterovirus (BEV), Bovine Coronovirus (BCV), Bovine Rabies (BR), Bovine Parvovirus (BPV), Adenovirus Astrovirus, *Mannheimia haemolytica* (formerly *Pasteurella haemolytica*), *Pasteurella multocida, Haemophilus somnus* (*Histophilus ovis* and *Haemophilus agni*), *Actinomyces* (Corynebacterium), *Actinomyces pyogenes, Chlamydia psittaci, Campylobacter fetus venerealis* and *Campylobacter fetus fetus* (formerly *C fetus* intestinalis), *Leptospira interrogans, Leptospira hardjo, Leptospira pomona*, and *Leptospira grippotyphosa, Leptospira canicola, Leptospira grippotyphosa, Leptospira hardjo* (*Leptospira hardjoprajitno* and *Leptospira hardjo-bovis*), *Brucella abortus, Brucella suis* and *Brucella melitensis, Listeria monocytogenes, Chlamydia psittaci, Clostridium chauvoei, Clostridium* septicum, Clostridium haemolyticum, Clostridium novyi, Clostridium sordellii, Clostridium perfringens, Clostridium tetani, Moraxella bovis, Klebsiella spp, Klebsiella pneumoniae, Salmonella typhimurium; Salmonella newport, Mycobacterium avium paratuberculosis, Cryptsporidium parvum, Cryptsporidium hominis, Staphylococcus aureus, Streptococcus dysgalactiae, Streptococcus uberis, Streptococcus agalactiae, Escherichia coli, Mycoplasma spp, Mycoplasma dispar, and Ureaplasma spp., Tritrichomonas foetus, Trichophyton verrucosum, Trichophyton mentagrophytes, Trichophyton sarkisovii, Neospora caninum (formerly Toxoplasma gondii), Babesia bigemina and Babesia bovis, Dictyocaulus viviparous (Lungworm disease), and combinations thereof.

3. The immunogenic composition according to claim 1, wherein the immunogenic composition is a combination vaccine.

4. The immunogenic composition according to claim 1, wherein said immunogenic composition is formulated for a single-dose administration.

5. A method of co-administration of two or more antigens to a cattle comprising, administering to said cattle one or more attenuated avirulent M. bovis antigen, wherein the M. bovis bacterium is passaged more than 100 times, wherein the M. bovis bacterium is selected from the group consisting of: the attenuated M. bovis bacteria strains deposited with the ATCC under accession numbers PTA-8694, PTA-8695, or PTA-8696; and one or more further immunologically active component(s) effective for the treatment of infections caused by a further cattle relevant pathogen other than M. bovis.

6. The method according to claim 5, wherein said infection caused by a further cattle relevant pathogen other than M. bovis is caused by at least one pathogen selected from the group consisting of:
Bovine viral diarrhea virus (BVDV), Parainfluenza-3 Virus (PI-3), Infectious Bovine Rhinotracheitis virus (IBR), Bovine Respiratory Syncytial Virus (BRSV), Bovine Herpesvirus (BHV), Bovine Rotavirus (BRV), Bovine Enterovirus (BEV), Bovine Coronovirus (BCV), Bovine Rabies (BR), Bovine Parvovirus (PPV), Adenovirus Astrovirus, Mannheimia haemolytica (formerly Pasteurella haemolytica), Pasteurella multocida, Haemophilus somnus (Histophilus ovis and Haemophilus agni), Actinomyces (Corynebacterium), Actinomyces pyogenes, Chlamydia psittaci, Campylobacter fetus venerealis and Campylobacter fetus fetus (formerly C fetus intestinalis), Leptospira interrogans, Leptospira hardjo, Leptospira pomona, and Leptospira grippotyphosa, Leptospira canicola, Leptospira grippotyphosa, Leptospira hardjo (Leptospira hardjoprajitno and Leptospira hardjo-bovis), Brucella abortus, Brucella suis and Brucella melitensis, Listeria monocytogenes, Chlamydia psittaci, Clostridium chauvoei, Clostridium septicum, Clostridium haemolyticum, Clostridium novyi, Clostridium sordellii, Clostridium perfringens, Clostridium tetani, Moraxella bovis, Klebsiella spp, Klebsiella pneumoniae, Salmonella typhimurium; Salmonella newport, Mycobacterium avium paratuberculosis, Cryptsporidium parvum, Cryptsporidium hominis, Staphylococcus aureus, Streptococcus dysgalactiae, Streptococcus uberis, Streptococcus agalactiae, Escherichia coli, Mycoplasma spp, Mycoplasma dispar, and Ureaplasma spp., Tritrichomonas foetus, Trichophyton verrucosum, Trichophyton mentagrophytes, Trichophyton sarkisovii, Neospora caninum (formerly Toxoplasma gondii), Babesia bigemina and Babesia bovis, Dictyocaulus viviparous (Lungworm disease), and combinations thereof.

7. The method according to claim 5, wherein the M. bovis antigen and the further immunologically active component(s) are administered separately.

8. The method according to claim 7, wherein the separate co-administration of the M. bovis antigen and the further immunologically active component(s) occurs within 2 days.

9. The method according to claim 5, wherein the two or more antigens which comprise M. bovis antigen and one or more further immunologically active component(s) effective for the treatment of infections caused by a further cattle relevant pathogen other than M. bovis are formulated as fix-dose combination vaccine.

10. The method according to claim 5, wherein the two or more antigens which comprise M. bovis antigen and one or more further immunologically active component(s) effective for the treatment of infections caused by a further cattle relevant pathogen other than M. bovis are administered to said cattle in one only dose.

11. The method according to claim 5, wherein said administration is effective in lessening or reducing the signs of a M. bovis infection.

12. An immunogenic composition for the prophylaxis of cattle against microbiological infections, wherein said immunogenic composition comprises:
a) one or more attenuated avirulent Mycoplasma bovis (M. bovis) antigens, wherein the M. bovis bacterium is passaged more than 100 times, wherein the M. bovis bacterium is selected from the group consisting of: the attenuated M. bovis bacteria strains deposited with the ATCC under accession numbers PTA-8694, PTA-8695, or PTA-8696; and
b) one or more further immunologically active component(s) effective for the prophylaxis of microbiological infection in cattle caused by a cattle pathogen other than M. bovis.

13. The immunogenic composition according to claim 12, wherein said microbiological infection in cattle caused by a cattle pathogen other than M. bovis is caused by one or more pathogens selected from the group consisting of:
Bovine viral diarrhea virus (BVDV), Parainfluenza-3 Virus (PI-3), Infectious Bovine Rhinotracheitis virus (IBR), Bovine Respiratory Syncytial Virus (BRSV), Bovine Herpesvirus (BHV), Bovine Rotavirus (BRV), Bovine Enterovirus (BEV), Bovine Coronovirus (BCV), Bovine Rabies (BR), Bovine Parvovirus (BPV), Adenovirus Astrovirus, Mannheimia haemolytica (formerly Pasteurella haemolytica), Pasteurella multocida, Haemophilus somnus (Histophilus ovis and Haemophilus agni), Actinomyces (Corynebacterium), Actinomyces pyogenes, Chlamydia psittaci, Campylobacter fetus venerealis and Campylobacter fetus fetus (formerly C fetus intestinalis), Leptospira interrogans, Leptospira hardjo, Leptospira pomona, and Leptospira grippotyphosa, Leptospira canicola, Leptospira grippotyphosa, Leptospira hardjo (Leptospira hardjoprajitno and Leptospira hardjo-bovis), Brucella abortus, Brucella suis and Brucella melitensis, Listeria monocytogenes, Chlamydia psittaci, Clostridium chauvoei, Clostridium septicum, Clostridium haemolyticum, Clostridium novyi, Clostridium sordellii, Clostridium perfringens, Clostridium tetani, Moraxella bovis, Klebsiella spp, Klebsiella pneumoniae, Salmonella typhimurium; Salmonella newport, Mycobacterium avium paratuberculosis, Cryptsporidium parvum, Cryptsporidium hominis, Staphylococcus aureus, Streptococcus

*dysgalactiae*, *Streptococcus uberis*, *Streptococcus agalactiae*, *Escherichia coli*, *Mycoplasma* spp, *Mycoplasma dispar*, and *Ureaplasma* spp., *Tritrichomonas foetus*, *Trichophyton verrucosum*, *Trichophyton mentagrophytes*, *Trichophyton sarkisovii*, *Neospora caninum* (formerly *Toxoplasma gondii*), *Babesia bigemina* and *Babesia bovis*, *Dictyocaulus viviparous* (Lungworm disease), and combinations thereof.

14. A method of co-administration of two or more antigens to a cattle comprising, administering to said cattle one or more attenuated avirulent *M. bovis* antigen, wherein the *M. bovis* bacterium is passaged more than 100 times, wherein the *M. bovis* bacterium is selected from the group consisting of: the attenuated *M. bovis* bacteria strains deposited with the ATCC under accession numbers PTA-8694, PTA-8695, or PTA-8696; and one or more further immunologically active component(s) effective for the prophylaxis of infections caused by a further cattle relevant pathogen other than *M. bovis*.

15. The method according to claim 14, wherein said infection caused by a further cattle relevant pathogen other than *M. bovis* is caused by at least one pathogen selected from the group consisting of:

Bovine viral diarrhea virus (BVDV), Parainfluenza-3 Virus (PI-3), Infectious Bovine Rhinotracheitis virus (IBR), Bovine Respiratory Syncytial Virus (BRSV), Bovine Herpesvirus (BHV), Bovine Rotavirus (BRV), Bovine Enterovirus (BEV), Bovine Coronovirus (BCV), Bovine Rabies (BR), Bovine Parvovirus (PPV), Adenovirus Astrovirus, *Mannheimia haemolytica* (formerly *Pasteurella haemolytica*), *Pasteurella multocida*, *Haemophilus somnus* (*Histophilus ovis* and *Haemophilus agni*), *Actinomyces* (Corynebacterium), *Actinomyces pyogenes*, *Chlamydia psittaci*, *Campylobacter fetus venerealis* and *Campylobacter fetus fetus* (formerly *C fetus* intestinalis), *Leptospira interrogans*, *Leptospira hardjo*, *Leptospira pomona*, and *Leptospira grippotyphosa*, *Leptospira canicola*, *Leptospira grippotyphosa*, *Leptospira hardjo* (*Leptospira hardjoprajitno* and *Leptospira hardjo-bovis*), *Brucella abortus*, *Brucella suis* and *Brucella melitensis*, *Listeria monocytogenes*, *Chlamydia psittaci*, *Clostridium chauvoei*, *Clostridium septicum*, *Clostridium haemolyticum*, *Clostridium novyi*, *Clostridium sordellii*, *Clostridium perfringens*, *Clostridium tetani*, *Moraxella bovis*, *Klebsiella* spp, *Klebsiella pneumoniae*, *Salmonella typhimurium; Salmonella newport*, *Mycobacterium avium* paratuberculosis, *Cryptosporidium parvum*, *Cryptosporidium hominis*, *Staphylococcus aureus*, *Streptococcus dysgalactiae*, *Streptococcus uberis*, *Streptococcus agalactiae*, *Escherichia coli*, *Mycoplasma* spp, *Mycoplasma dispar*, and *Ureaplasma* spp., *Tritrichomonas foetus*, *Trichophyton verrucosum*, *Trichophyton mentagrophytes*, *Trichophyton sarkisovii*, *Neospora caninum* (formerly *Toxoplasma gondii*), *Babesia bigemina* and *Babesia bovis*, *Dictyocaulus viviparous* (Lungworm disease), and combinations thereof.

* * * * *